US006861508B2

(12) United States Patent
Chambon et al.

(10) Patent No.: US 6,861,508 B2
(45) Date of Patent: Mar. 1, 2005

(54) TRANSCRIPTIONAL INTERMEDIARY FACTOR-2

(75) Inventors: Pierre Chambon, Blaesheim (FR); Hinrich Gronemeyer, Oberkirch (DE); Johannes Voegel, Strasbourg (FR); Yves Lutz, Strasbourg (FR)

(73) Assignees: Institut National de la Sante et de la Recherche Medicale, Paris (FR); Centre National de la Recherche Scientifique, Paris (FR); Universite Louis Pasteur, Strasbourg (FR); Bristol-Myers Squibb Company, Princeton, NJ (US)

( * ) Notice: Subject to any disclaimer, the term of this patent is extended or adjusted under 35 U.S.C. 154(b) by 273 days.

(21) Appl. No.: 09/842,256

(22) Filed: Apr. 26, 2001

(65) Prior Publication Data

US 2002/0106727 A1 Aug. 8, 2002

Related U.S. Application Data

(62) Division of application No. 08/891,640, filed on Jul. 11, 1997, now Pat. No. 6,268,173.
(60) Provisional application No. 60/021,247, filed on Jul. 12, 1996.

(51) Int. Cl.[7] .............................................. C07K 14/00
(52) U.S. Cl. ...................................... 530/350; 530/300
(58) Field of Search .......................... 536/350; 435/69.1

(56) References Cited

U.S. PATENT DOCUMENTS

| 5,508,164 A | 4/1996 | Kausch et al. |
| 6,268,173 B1 | 7/2001 | Chambon et al. |

FOREIGN PATENT DOCUMENTS

| WO | WO 96/12823 | 5/1996 |
| WO | WO 98/02455 | 1/1998 |

OTHER PUBLICATIONS

Berry, M., et al., "Role of the two activating domains of the oestrogen receptor in the cell–type and promoter–context dependent agonistic activity of the anti–oestrogen 4–hydroxytamoxifen," *EMBO J.* 9:2811–2818, Oxford University Press (1990).

Bocquel, M.T., et al., "The contribution of the N– and C–terminal regions of steroid receptors to activation of transcription is both receptor and cell–specific," *Nucl. Acids Res.* 17:2581–2595, Oxford University Press (1989).

Bourguet, W., et al., "Crystal structure of the ligand–binding domain of the human nuclear receptor RXR–α," *Nature* 375:377–382, Nature Publishing Group (Jun. 1995).

Cavailles, V., et al., "Interaction of proteins with transcriptionally active estrogen receptors," *Proc. Natl. Acad. Sci. USA* 91:10009–10013, National Academy of Sciences (1994).

Cavailles, V., et al., "Nuclear factor RIP140 modulates transcriptional activation by the estrogen receptor," *EMBO J.* 14:3741–3751, Oxford University Press (Aug. 1995).

Danielian, P.S., et al., "Identification of a conserved region required for hormone dependent transcriptional activation by steroid hormone receptors," *EMBO J.* 11:1025–1033, Oxford University Press (1992).

Durand, B., et al., "Activation function 2 (AF–2) of retinoic acid receptor and 9–cis retinoic acid receptor: presence of a conserved autonomous constitutive activating domain and influence of the nature of the response element of AF–2 activity," *EMBO J.* 13:5370–5382, Oxford University Press (1994).

George, D.G., et al., in: *Macromolecular Sequencing and Synthesis. Selected Methods and Applications*, Schlesinger, D.H., ed., Alan R. Liss, Inc., New York, pp. 127–149 (1988).

Glass, C.K., et al., "Nuclear receptor coactivators," *Curr. Opin. Cell Biol.* 9:222–232, Current Biology Ltd. (Apr. 1997).

Halachmi, S., et al., "Estrogen Receptor–Associated Proteins: Possible Mediators of Hormone–Induced Transcription," *Science* 264:1455–1458, American Association for the Advancement of Science (1994).

Hanstein, B., et al., "p300 is a component of an estrogen receptor coactivator complex," *Proc. Natl. Acad. Sci. USA* 93:11540–11545, National Academy of Sciences (Oct. 1996).

Heery, D.M. et al., "A signature motif in transcriptional co–activators mediates binding to nuclear receptors," *Nature* 387:733–736, Nature Publishing Group (Jun. 1997).

Hong, H., et al., "GRIP1, a novel mouse protein that serves as a transcriptional coactivator in yeast for the hormone binding domains of steroid receptors," *Proc. Natl. Acad. Sci. USA* 93:4948–4952, National Academy of Sciences (May 1996).

Hong, H., et al., "GRIP1, a Transcriptional Coactivator for the AF–2 Transactivation Domain of Steroid, Thyroid, Retinoid, and Vitamin D Receptors," *Mol. Cell. Biol.* 17:2735–2744, American Society for Microbiology (May 1997).

Jacq, X., et al., "Human TAF$_{II}$30 Is Present in a Distinct TFIID Complex and Is Required for Transcriptional Activation by the Estrogen Receptor," *Cell* 79:107–117, Cell Press (1994).

(List continued on next page.)

Primary Examiner—Michael Pak
(74) Attorney, Agent, or Firm—Sterne, Kessler, Goldstein & Fox P.L.L.C.

(57) ABSTRACT

The present invention concerns a nuclear receptor (NR) transcriptional mediator. More specifically, isolated nucleic acid molecules are provided encoding transcriptional intermediary factor-2 (TIF2). Recombinant methods for making TIF2 polypeptides are also provided as are TIF2 antibodies. Screening methods are also provided for identifying agonists and antagonists of the activation function AF-2 of nuclear receptors, for identifying agonists and antagonists of the AD1 activation domain activity of TIF2, and for identifying agonists and antagonists of the AD2 activation domain activity of TIF2.

22 Claims, 46 Drawing Sheets

OTHER PUBLICATIONS

Kamei, Y., et al., "CBP Integrator Complex Mediates Transcriptional Activation and AP–1 Inhibition by Nuclear Receptors," *Cell 85*:403–414, Cell Press (May 1996).

Kastner, P., et al., "Structure, localization and transcriptional properties of two classes of retinoic acid receptor α fusion proteins in acute promyelocytic leukemia (APL): structural similarities with a new family of oncoproteins," *EMBO J. 11*:629–642, Oxford University Press (1992).

Kurokawa, R., et al., "Polarity–specific activities of retinoic acid receptors determined by a co–repressor," *Nature 377*:451–454, Nature Publishing Group (Oct. 1995).

Le Douarin, B., et al., "The N–terminal part of TIF1, a putative mediator of the ligand–dependent activation function (AF–2) of nuclear receptors, is fused to B–raf in the oncogenic protein T18," *EMBO J. 14*:2020–2033, Oxford University Press (May 1995).

Le Douarin, B., et al., "A possible involvement of TIF1α and TIFβ in the epigenetic control of transcription by nuclear receptors," *EMBO J. 15*:6701–6715, Oxford University Press (Dec. 1996).

Lee, J.W., et al., "Two Classes of Proteins Dependent on Either the Presence or Absence of Thyroid Hormone for Interaction with the Thyroid Hormone Receptor," *Mol. Endocrinol. 9*:243–254, The Endocrine Society (Feb. 1995).

Lee, J.W., et al., "Interaction of thyroid–hormone receptor with a conserved transcriptional mediator," *Nature 374*:91–94, Nature Publishing Group (Mar. 1995).

Mengus, G., et al., "Cloning and characterization of hTAF$_{II}$18, hTAF$_{II}$20 and hTAF$_{II}$28: three subunits of the human transcription factor TFIID," *EMBO J. 14*:1520–1531 (Apr. 1995).

Metzger, D., et al., "Promoter specificity of the two transcriptional activation functions of the human oestrogen receptor in yeast," *Nucl. Acids Res. 20*:2813–2817, Oxford University Press (1992).

Meyer, M.–E., et al., "Steroid Hormone Receptors Compete for Factors That Mediate Their Enhancer Function," *Cell 57*:433–422, Cell Press (1989).

Meyer, M.–E., et al., "Agonistic and antagonistic activities of RU486 on the functions of the human progesterone receptor," *EMBO J. 9*:3923–3932, Oxford University Press (1990).

Onate, S.A., et al., "Sequence and Characterization of a Coactivator for the Steroid Hormone Receptor Superfamily," *Science 270*:1354–1357, American Association for the Advancement of Science (Nov. 1995).

Pierrat, B., et al., "Functional analysis of the human estrogen receptor using a phenotypic transctivation assay in yeast," *Gene 119*:237–245, Elsevier Science B.V. (1992).

Pierrat, B., et al., "A highly conserved region in the hormone–binding domain of the human estrogen receptor functions as an efficient transactivation domain in yeast," *Gene 143*:193–200, Elsevier Science B.V. (1994).

Renaud, J.–P., et al., "Crystal structure of the RAR–γ ligand–binding domain bound to all–trans retinoic acid," *Nature 378*681–689, Nature Publishing Group (Dec. 1995).

Tasset, D., et al., "Distinct Classes of Transcriptional Activating Domains Function by Different Mechanisms," *Cell 62*:1177–1187, Cell Press (1990).

Torchia, J., et al., "The transcriptional co–activator p/CIP binds CBP and mediates nuclear–receptor function," *Nature 387*:677–684, Nature Publishing Group (Jun. 1997).

Voegel, J.J., et al., "TIF2, a 16 kDa transcriptional mediator for the ligand–dependent activation function AF–2 of nuclear receptors," *EMBO J. 15*:3667–3675, Oxford University Press (Jul. 1996).

vom Baur, E., et al., "Differential ligand–dependent interactions between the AF–2 activating domain of nuclear receptors and the putative transcriptional intermediary factors mSUG1 and TIF1," *EMBO J. 15*:110–124, Oxford University Press (Jan. 1996).

Wagner, R.L., et al., "A structural role for hormone in the thyroid hormone receptor," *Nature 378*:690–697, Nature Publishing Group (Dec. 1995).

Wurtz, J.–M., et al., "A canonical structure for the ligand–binding domain of nuclear receptors," *Nature Struct. Biol. 3*:87–94, Nature Publishing Company (Jan. 1996).

Yao, T.–P., et al., "The nuclear hormone receptor coactivator SRC–1 is a specific target of p300," *Proc. Natl. Acad. Sci. USA 93*:10626–10631, National Academy of Sciences (Oct. 1996).

Zhu, Y., et al., "Cloning and Identification of Mouse Steroid Receptor Coactivator–1 (mSRF–1), as a Coactivator of Peroxisome Proliferator–Activated Receptor γ," *Gene Expression 6*:185–195, Chicago Medical School Press (1996).

```
GGCGGCCGCA GCCTCGGCTA CAGCTTCGGC GGGGAAGGTC AGCGCCGACG GCAGCCGGCA    60

CCTGACGGCG TGACCGACCC GAGCCGATTT CTCTTGGATT TGGCTACACA CTTATAGATC   120

TTCTGCACTG TTTACAGGCA CAGTTGCTGA TATGTGTTCA AG ATG AGT GGG ATG     174
                                               Met Ser Gly Met
                                                1

GGA GAA AAT ACC TCT GAC CCC TCC AGG GCA GAG ACA AGA AAG CGC AAG    222
Gly Glu Asn Thr Ser Asp Pro Ser Arg Ala Glu Thr Arg Lys Arg Lys
            10                      15                      20

GAA TGT CCT GAC CAA CTT GGA CCC AGC CCC AAA AGG AAC ACT GAA AAA    270
Glu Cys Pro Asp Gln Leu Gly Pro Ser Pro Lys Arg Asn Thr Glu Lys
                25                      30                      35

CGT AAT CGT GAA CAG GAA AAT CAG GAA AAT TAT ATA GAA GAA CTT GCA GAG TTG    318
Arg Asn Arg Glu Gln Glu Asn Lys Tyr Ile Glu Glu Leu Ala Glu Leu
        40                      45                      50

ATT TTT GCA ATC TTA AAA GAA ACT GTG AAG CAA ATT CGT CAG ATC AAA    366
Ile Phe Ala Ile Leu Lys Glu Thr Val Lys Gln Ile Arg Gln Ile Lys
                55                      60                      65

AAA TGT GCA GCA GCA GCT GCC AAC ATA GAT GAA GTG CAG AAG TCA        414
Lys Cys Ala Ala Ala Ala Ala Asn Ile Asp Glu Val Gln Lys Ser
        70                      75                      80

GAA CAA GAG AAA GCA GCT GCC AAC ATA GAT GAA GTG CAG AAG TCA        462
Glu Gln Glu Lys Ala Ala Ala Asn Ile Asp Glu Val Gln Lys Ser
        85                      90                      95                      100
```

FIG.1A

```
GAT GTA TCC TCT ACA GGG CAG GGT GTC ATC GAC AAG GAT GCG CTG GGG    510
Asp Val Ser Ser Thr Gly Gln Gly Val Ile Asp Lys Asp Ala Leu Gly
        105                     110                     115

CCT ATG ATG CTT GAG GCC CTT GAT GGG TTC TTT GTA GTG TTC AAC CTG    558
Pro Met Met Leu Glu Ala Leu Asp Gly Phe Phe Val Val Phe Asn Leu
        120                     125                     130

GAA GGC AAC GTT GTG TTT GTG TCA GAG AAT GTG ACA CAG TAT CTA AGG    606
Glu Gly Asn Val Val Phe Val Ser Glu Asn Val Thr Gln Tyr Leu Arg
        135                     140                     145

TAT AAC CAA GAA CTG CTG ATG AAC AAA AGT GTA TAT AGC ATC TTG CAT    654
Tyr Asn Gln Glu Leu Leu Met Asn Lys Ser Val Tyr Ser Ile Leu His
        150                     155                     160

GTT GGG GAC CAC ACG GAA TTT GTC AAA AAC CTG CCA AAG TCT ATA        702
Val Gly Asp His Thr Glu Phe Val Lys Asn Leu Pro Lys Ser Ile
        165                     170                     175         Ile
                                                                    180

GTA AAT GGG GGA TCT GGA TGG TCT TGG GAA GGT CCT CCG AGG CGG AAC AGC CAT    750
Val Asn Gly Gly Ser Gly Trp Ser Trp Glu Gly Pro Pro Arg Arg Asn Ser His
        185                     190                     195

ACC TTC AAT TGT CGG ATG CTG GTA AAA CCT TTA CCT GAT TCA GAA GAG    798
Thr Phe Asn Cys Arg Met Leu Val Lys Pro Leu Pro Asp Ser Glu Glu
        200                     205                     210

GAG GGT CAT GAT AAC CAG GAA GCT CAT CAG AAA TAT GAA ACT ATG CAG    846
Glu Gly His Asp Asn Gln Glu Ala His Gln Lys Tyr Glu Thr Met Gln
        215                     220                     225
```

FIG.1B

| | | | | | | | | |
|---|---|---|---|---|---|---|---|---|
| TGC Cys | TTC Phe | GCT Ala | GTC Val | TCT Ser | CAA Gln | CCA Pro | AAG Lys | TCC Ser | ATC Ile | AAA Lys | GAA Glu | GAA Glu | GGA Gly | GAA Glu | GAT Asp | 894 |

Cys Phe Ala Val Ser Gln Pro Lys Ser Ile Lys Glu Glu Gly Glu Asp
230                             235                             240

TTG CAG TCC TGC TTG ATT TGC GTG GCA AGA AGA GTT CCC ATG AAG GAA    942
Leu Gln Ser Cys Leu Ile Cys Val Ala Arg Arg Val Pro Met Lys Glu
245                             250                             255                             260

AGA CCA GTT CTT CCC TCA GAA AGT TTT ACT CGC CAG GAT CTC    990
Arg Pro Val Leu Pro Ser Glu Ser Phe Thr Thr Arg Gln Asp Leu
265                             270                             275

CAA GGC AAG ATC ACG TCT CTG GAT ACC AGC ATG ACC AGA GCA GCC ATG    1038
Gln Gly Lys Ile Thr Ser Leu Asp Thr Ser Met Thr Arg Ala Ala Met
280                             285                             290

AAA CCA TGG GAG GAC CTG GTA AGA AGG TGT ATT CAG AAG TTC CAT    1086
Lys Pro Trp Glu Asp Leu Val Arg Arg Cys Ile Gln Lys Phe His
295                             300                             305

GCG CAG CAT GAA GGA GAA TCT GTG TCC TAT GCT AAG ATC TAT CGT CAT CAT    1134
Ala Gln His Glu Gly Glu Ser Val Ser Tyr Ala Lys Ile Tyr Arg His His
310                             315                             320

GAA GTA CTG AGA CAA GGA TTG GCA TTC AGT CAA TTC CGT TTT TCC    1182
Glu Val Leu Arg Gln Gly Leu Ala Phe Ser Gln Phe Arg Phe Ser
325                             330                             335                             340

TTG TCT GAT GGC ACT CTT GTT GCT GCA CAA ACG AAG AGC AAA CTC ATC    1230
Leu Ser Asp Gly Thr Leu Val Ala Ala Gln Thr Lys Ser Lys Leu Ile
345                             350                             355

FIG.1C

```
CGT TCT CAG ACT AAT GAA CCT CAA CTT GTA ATA TCT TTA CAT ATG        1278
Arg Ser Gln Thr Asn Glu Pro Gln Leu Val Ile Ser Leu His Met
            360                 365                 370

CTT CAC AGA GAG CAG AAT GTG TGT ATG GTG AAT CCG GAT CTG GGA        1326
Leu His Arg Glu Gln Asn Val Cys Met Val Asn Pro Asp Leu Thr Gly
        375                 380                 385

CAA ACG ATG GGG AAG CCA CTG AAT CCA ATT AGC TCT AAC AGC CCT GCC    1374
Gln Thr Met Gly Lys Pro Leu Asn Pro Ile Ser Ser Asn Ser Pro Ala
        390                 395                 400

CAT CAG GCC CTG TGC AGT GGG AAC CCA GGT CAG GAC ATG ACC CTC AGT    1422
His Gln Ala Leu Cys Ser Gly Asn Pro Gly Gln Asp Met Thr Leu Ser
        405                 410                 415                 420

AGC AAT ATA AAT TTT CCC ATA AAT GGC CCA AAG CAA ATG AAC CAT GTG    1470
Ser Asn Ile Asn Phe Pro Ile Asn Gly Pro Lys Gln Met Asn His Val
        425                 430                 435

CCC ATG GGC AGG ACC ACT CCT CAG GGT TCT GGT GGG ATG GGC TCA GGC    1518
Pro Met Gly Arg Thr Thr Pro Gln Gly Ser Gly Gly Met Gly Ser Gly
        440                 445                 450

ATG CAA GCA ACC CCT CAG GGT AGT AAC TAT GCA CTC AAA ATG AAC        1566
Met Gln Ala Thr Pro Gln Gly Ser Asn Tyr Ala Leu Lys Met Asn
        455                 460                 465

AGC CCC TCA CAA AGC AGC CCT GGC ATG AAT CCA GGA CAG CCC ACC TCC    1614
Ser Pro Ser Gln Ser Ser Pro Gly Met Asn Pro Gly Gln Pro Thr Ser
        470                 475                 480
```

FIG.1D

| | | | | | | | | |
|---|---|---|---|---|---|---|---|---|
| ATG Met 485 | CTT Leu | TCA Ser | CCA Pro | AGG Arg | CAT His 490 | CGC Arg | ATG Met | AGC Ser | CCT Pro | GGA Gly 495 | GTG Val | GCT Ala | AGC Gly | CCT Pro 500 | 1662 |

Row by row:

ATG CTT TCA CCA AGG CAT CGC ATG AGC CCT GGA GTG GCT AGC CCT    1662
Met Leu Ser Pro Arg His Arg Met Ser Pro Gly Val Ala Gly Ser Pro
485              490                 495                500

CGA ATC CCA CCC AGT CAG TTT CCT GCA GGA AGC TTG CAT TCC CCT    1710
Arg Ile Pro Pro Ser Gln Phe Pro Ala Gly Ser Leu His Ser Pro
         505                 510                 515

GTG GGA GTT TGC AGC ACA GGA AAT AGC CAT AGT TAT ACC AAC AGC    1758
Val Gly Val Cys Ser Thr Gly Asn Ser His Ser Tyr Thr Asn Ser
        520                  525                 530

TCC CTC AAT GCA CTT CAG GCC CTC AGC GAG GGG CAC GGG GTC TCA TTA    1806
Ser Leu Asn Ala Leu Gln Ala Leu Ser Glu Gly His Gly Val Ser Leu
        535                 540                 545

GGG TCA TCG GCT TCA CCA GAC CTA AAA ATG GGC AAT TTG CAA AAC    1854
Gly Ser Ser Leu Ala Ser Pro Asp Leu Lys Met Gly Asn Leu Gln Asn
    550                 555                 560

TCC CCA GTT AAT ATG AAT CCT CCC CCA AGC CTC GAG AAG ATG AGC TTG    1902
Ser Pro Val Asn Met Asn Pro Pro Pro Ser Leu Glu Lys Met Gly Ser Leu
565                 570                 575                 580

GAC TCA AAA GAC TGT CTA TTT GGA TAT GGG TCT GAA GGT ACA    1950
Asp Ser Lys Asp Cys Phe Gly Leu Tyr Gly Ser Glu Gly Thr
585                 590                 595

ACT GGA CAA GCA GAG AGC TGC CAT CCT GGA GAG CAA AAG GAA ACA    1998
Thr Gly Gln Ala Glu Ser Cys His Pro Gly Glu Gln Lys Glu Thr
    600                 605                 610

FIG.1E

| | | | | | | | | | | | | | | | |
|---|---|---|---|---|---|---|---|---|---|---|---|---|---|---|---|
| AAT | GAC | CCC | AAC | CTG | CCC | CCG | GCC | GTG | AGC | AGT | GAG | AGA | GCT | GAC | GGG | 2046
| Asn | Asp | Pro | Asn | Leu | Pro | Pro | Ala | Val | Ser | Ser | Glu | Arg | Ala | Asp | Gly |
| | | 615 | | | | | 620 | | | | | 625 | | | |
| CAG | AGC | AGA | CTG | CAT | GAC | AGC | AGT | GGG | CAG | ATG | GAG | CCC | AAA | CTC | CTG | 2094
| Gln | Ser | Arg | Leu | His | Asp | Ser | Ser | Gly | Gln | Met | Glu | Pro | Lys | Leu | Leu |
| | 630 | | | | | 635 | | | | 640 | | | | | |
| CTG | ACC | AAA | TCT | GAT | CAG | ATG | GAG | CCC | TCG | CCC | TTA | GCC | AGC | TCT | | 2142
| Leu | Thr | Lys | Ser | Asp | Gln | Met | Glu | Pro | Ser | Pro | Leu | Ala | Ser | Ser | |
| 645 | | | | 650 | | | | 655 | | | | 660 | | | |
| TTG | TCG | GAT | ACA | AAC | GAC | TCC | ACA | GGT | AGC | TTG | CCT | GGT | TCT | GGG | | 2190
| Leu | Ser | Asp | Thr | Asn | Asp | Ser | Thr | Gly | Ser | Leu | Pro | Gly | Ser | Gly | |
| | | | 665 | | | | 670 | | | | 675 | | | | |
| TCT | ACA | CAT | GGA | ACC | TCG | CTC | AAG | GAG | AAG | CAT | AAA | ATT | TTG | CAC | AGA | 2238
| Ser | Thr | His | Gly | Thr | Ser | Leu | Lys | Glu | Lys | His | Lys | Ile | Leu | His | Arg |
| 680 | | | | | 685 | | | | 690 | | | | | | |
| CTC | TTG | CAG | GAC | AGT | TCC | CCT | GTG | GAC | CAG | GAG | TCC | TTG | GCC | AAG | TTA | ACA | GCA | 2286
| Leu | Leu | Gln | Asp | Ser | Ser | Pro | Val | Asp | Gln | Glu | Ser | Leu | Ala | Lys | Leu | Thr | Ala |
| | | 695 | | | | 700 | | | | 705 | | | | | |
| GAA | GCC | ACA | GGC | AAA | GAC | CTG | AGC | CAG | TCC | AGC | ACA | GCT | CCT | | 2334
| Glu | Ala | Thr | Gly | Lys | Asp | Leu | Ser | Gln | Ser | Ser | Thr | Ala | Pro | |
| 710 | | | | | 715 | | | | 720 | | | | | |
| GGA | TCA | GAA | GTG | ACT | ATT | AAA | CAA | GAG | CCG | GTG | AGC | ACA | AAG | AAG | AAA | 2382
| Gly | Ser | Glu | Val | Thr | Ile | Lys | Gln | Glu | Pro | Val | Ser | Pro | Lys | Lys | Lys |
| 725 | | | | | 730 | | | | 735 | | | | | 740 | |

FIG. 1F

| | | | | | | | | |
|---|---|---|---|---|---|---|---|---|
| GAG | AAT | GCA | CTA | CTT | CGC | TAT | TTG | CTA | GAT | AAA | GAT | ACT | AAA | GAT | 2430 |
| Glu | Asn | Ala | Leu | Leu | Arg | Tyr | Leu | Leu | Asp | Lys | Asp | Thr | Lys | Asp | |
| | | | | 745 | | | | | 750 | | | | | 755 | |

| ATT | GGT | TTA | CCA | GAA | ATA | ACC | CCC | AAA | GAT | GAT | CTG | GAC | AGT | AAG | 2478 |
| Ile | Gly | Leu | Pro | Glu | Ile | Thr | Pro | Lys | Asp | Asp | Leu | Asp | Ser | Lys | |
| | | 760 | | | | | 765 | | | | | 770 | | | |

| ACA | GAT | CCT | GCC | AGT | AAC | ACA | AAA | TTA | ATA | GCA | ATG | AAA | ACT | GAG | AAG | 2526 |
| Thr | Asp | Pro | Ala | Ser | Asn | Thr | Lys | Leu | Ile | Ala | Met | Lys | Thr | Glu | Lys |
| | | 775 | | | | | 780 | | | | | 785 | | | |

| GAG | GAG | ATG | AGC | TTT | GAG | CCT | GGT | GAC | CAG | CCT | GGC | AGT | GAG | CTG | GAC | 2574 |
| Glu | Glu | Met | Ser | Phe | Glu | Pro | Gly | Asp | Gln | Pro | Gly | Ser | Glu | Leu | Asp |
| | 790 | | | | | 795 | | | | | 800 | | | | |

| AAC | TTG | GAG | GAG | ATT | TTG | GAT | GAT | TTG | CAG | AAT | AGT | CAA | TTA | CCA | CAG | 2622 |
| Asn | Leu | Glu | Glu | Ile | Leu | Asp | Asp | Leu | Gln | Asn | Ser | Gln | Leu | Pro | Gln |
| 805 | | | | | 810 | | | | | 815 | | | | | 820 |

| CTT | TTC | CCA | GAC | ACG | AGG | CCA | GCC | GCC | CCT | GCT | GGA | TCA | GTT | GAC | AAG | 2670 |
| Leu | Phe | Pro | Asp | Thr | Arg | Pro | Ala | Ala | Pro | Ala | Gly | Ser | Val | Asp | Lys |
| | | 825 | | | | | 830 | | | | | 835 | | | |

| CAA | GCC | ATC | ATC | AAT | GAC | CTC | ATG | CAA | AAA | CTC | ACA | GCT | GAA | AAC | AGC | CCT | 2718 |
| Gln | Ala | Ile | Ile | Asn | Asp | Leu | Met | Gln | Lys | Leu | Thr | Ala | Glu | Asn | Ser | Pro |
| | 840 | | | | | 845 | | | | | 850 | | | | | |

| GTC | ACA | CCT | GTT | GGA | GCC | CAG | AAA | ACA | GCA | CTG | CGA | ATT | TCA | CAG | AGC | 2766 |
| Val | Thr | Pro | Val | Gly | Ala | Gln | Lys | Thr | Ala | Leu | Arg | Ile | Ser | Gln | Ser |
| 855 | | | | | 860 | | | | | 865 | | | | | |

FIG.1G

```
ACT TTT AAT AAC CCA CGA CCA GGG CAA CTG GGC AGG TTA TTG CCA AAC      2814
Thr Phe Asn Asn Pro Arg Pro Gly Gln Leu Gly Arg Leu Leu Pro Asn
870                 875                 880

CAG AAT TTA CCA CTT GAC ATC ACA TTG CAA AGC CCA ACT GGT GCT GGA      2862
Gln Asn Leu Pro Leu Asp Ile Thr Leu Gln Ser Pro Thr Gly Ala Gly
    885                 890                 895                 900

CCT TTC CCA CCA ATC AGA AAC AGT AGT CCC TAC TCA GTG ATA CCT CAG      2910
Pro Phe Pro Pro Ile Arg Asn Ser Ser Pro Tyr Ser Val Ile Pro Gln
            905                 910                 915

CCA GGA ATG ATG GGT AAT CAA GGG ATG ATA GGA AAC CAA GGA AAT TTA      2958
Pro Gly Met Met Gly Asn Gln Gly Met Ile Gly Asn Gln Gly Asn Leu
        920                 925                 930

GGG AAC AGT ACA AGC ACT GGA ATT GGT AAC AGT GCT TCT CGG CCT ACT      3006
Gly Asn Ser Thr Ser Thr Gly Ile Gly Asn Ser Ala Ser Arg Pro Thr
            935                 940                 945

ATG CCA TCT GGA GAA TGG GCA CCG CAG AGT TCG GCT GTG AGA GTC ACC      3054
Met Pro Ser Gly Glu Trp Ala Pro Gln Ser Ser Ala Val Arg Val Thr
    950                 955                 960

TGT GCT ACC ACC AGT ACC ATG GCC AAC CGG CCA GTC CAA GGA GGT ATG      3102
Cys Ala Thr Thr Ser Thr Met Ala Asn Arg Pro Val Gln Gly Gly Met
965                 970                 975                 980

ATT CGG AAC CCA GCA GCC AGC ATC CCC ATG AGG CCC ATG AGC AGC CAG CCT  3150
Ile Arg Asn Pro Ala Ala Ser Ile Pro Met Arg Pro Met Ser Ser Gln Pro
            985                 990                 995
```

FIG.1H

```
GGC CAA AGA CAG ACG CTT CAG TCT ATG AAT ATA GGG CCA TCT    3198
Gly Gln Arg Gln Thr Leu Gln Ser Met Asn Ile Gly Pro Ser
                1000                    1005                    1010

GAA TTA GAG ATG AAC ATG GGG GGA CCT CAG TAT AGC CAA CAA GCT    3246
Glu Leu Glu Met Asn Met Gly Gly Pro Gln Tyr Ser Gln Gln Ala
                1015                    1020                    1025

CCT CCA AAT CAG ACT GCC CCA TGG CCT GAA AGC ATC CTG CCT ATA GAC    3294
Pro Pro Asn Gln Thr Ala Pro Trp Pro Glu Ser Ile Leu Pro Ile Asp
                1030                    1035                    1040

CAG GCG TCT TTT GCC AGC CAA AAC AGG CAG CCA TTT GGC AGT TCT CCA    3342
Gln Ala Ser Phe Ala Ser Gln Asn Arg Gln Pro Phe Gly Ser Ser Pro
                1045                    1050                    1055                    1060

GAT GAC TTG CTA TGT CCA CAT CCT GCA GCT GAG TCT CCG AGT GAT GAG    3390
Asp Asp Leu Leu Cys Pro His Pro Ala Ala Glu Ser Pro Ser Asp Glu
                1065                    1070                    1075

GGA GCT CTC CTG GAC CAG CTG TAT CTG GCC TTG CGG AAT TTT GAT GGC    3438
Gly Ala Leu Leu Asp Gln Leu Tyr Leu Ala Leu Arg Asn Phe Asp Gly
                1080                    1085                    1090

CTG GAG GAG ATT GAT AGA GCC TTA GGA ATA CCC GAA CTG GTC AGC CAG    3486
Leu Glu Glu Ile Asp Arg Ala Leu Gly Ile Pro Glu Leu Val Ser Gln
                1095                    1100                    1105

AGC CAA GCA GTA GAT CCA GAA CAG TTC TCA AGT CAG GAT TCC AAC ATC    3534
Ser Gln Ala Val Asp Pro Glu Gln Phe Ser Ser Gln Asp Ser Asn Ile
                1110                    1115                    1120
```

FIG. 1I

```
ATG CTG GAG CAG AAG GCG CCC GTT TTC CCA CAG CAG TAT GCA TCT CAG      3582
Met Leu Glu Gln Lys Ala Pro Val Phe Pro Gln Gln Tyr Ala Ser Gln
1125                    1130                    1135            1140

GCA CAA ATG GCC CAG GGT AGC TAT TCT CCC ATG CAA GAT CCA AAC TTT      3630
Ala Gln Met Ala Gln Gly Ser Tyr Ser Pro Met Gln Asp Pro Asn Phe
            1145                    1150                    1155

CAC ACC ATG GGA CAG CGG CCT AGT TAT GCC ACA CTC CGT ATG CAG CCC      3678
His Thr Met Gly Gln Arg Pro Ser Tyr Ala Thr Leu Arg Met Gln Pro
        1160                    1165                    1170

AGA CCG GGC CTC AGG CCC ACG GGC CTA GTG CAG AAC CAG CCA AAT CAA      3726
Arg Pro Gly Leu Arg Pro Thr Gly Leu Val Gln Asn Gln Pro Asn Gln
            1175                    1180                    1185

CTA AGA CTT CAA CTT CAG CAT CGC CTC CAA GCA CAG CAG AAT CGC CAG      3774
Leu Arg Leu Gln Leu Gln His Arg Leu Gln Ala Gln Gln Asn Arg Gln
        1190                    1195                    1200

CCA CTT ATG AAT CAA ATC AGC AAT GTT TCC AAT GTG AAC TTG ACT CTG      3822
Pro Leu Met Asn Gln Ile Ser Asn Val Ser Asn Val Asn Leu Thr Leu
1205                    1210                    1215            1220

AGG CCT GGA GTA CCA ACA CAG CCT CAG ATT AAT GCA CAG ATG CTG GCC      3870
Arg Pro Gly Val Pro Thr Gln Pro Gln Ile Asn Ala Gln Met Leu Ala
            1225                    1230                    1235

CAG AGA CAG AGG GAA ATC CTG AAC CAG CAT CTT CGA CAG CAA AGA ATG      3918
Gln Arg Gln Arg Glu Ile Leu Asn Gln His Leu Arg Gln Gln Arg Met
        1240                    1245                    1250
```

FIG. 1J

```
CAT CAG CAA CAG CAA GTT CAG CAA CGA ACT TTG ATG ATG AGA GGA CAA           3966
His Gln Gln Gln Gln Val Gln Gln Arg Thr Leu Met Met Arg Gly Gln
1255                                  1260                      1265

GGG TTG AAT ATG ACA CCA AGC GTG ATG GCT CCT AGT GGT ATG CCA GCA           4014
Gly Leu Asn Met Thr Pro Ser Met Val Ala Pro Ser Gly Met Pro Ala
     1270                   1275                    1280

ACT ATG AGC AAC CCT CGG ATT CCC CAG GCA AAT GCA CAG CAG TTT CCA           4062
Thr Met Ser Asn Pro Arg Ile Pro Gln Ala Asn Ala Gln Gln Phe Pro
1285                            1290                   1295         1300

TTT CCT CCA AAC TAC ATA AGT CAG CAA CCT GAT CCA GGC TTT ACT              4110
Phe Pro Pro Asn Tyr Gly Ile Ser Gln Gln Pro Asp Pro Gly Phe Thr
          1305                        1310                    1315

GGG GCT ACG ACT CCC CAG AGC CCA CTT ATG TCA CCC CGA ATG GCA CAT           4158
Gly Ala Thr Thr Pro Gln Ser Pro Leu Met Ser Pro Arg Met Ala His
        1320                         1325                     1330

ACA CAG AGT CCC ATG ATG CAA CAG TCT CAG GCC AAC CCA GCC TAT CAG           4206
Thr Gln Ser Pro Met Met Gln Gln Ser Gln Ala Asn Pro Ala Tyr Gln
         1335                         1340                    1345

GCC CCC TCC GAC ATA AAT GGA TGG GCG CAG ATG GGC AAC GGA AAC              4254
Ala Pro Ser Asp Ile Asn Gly Trp Ala Gln Met Gly Asn Gly Asn
          1350                         1355                  1360

AGC ATG TTT TCC CAG CAG TCC CCA CAC TTT GGG CAG CAA GCA AAC               4302
Ser Met Phe Ser Gln Gln Ser Pro His Phe Gly Gln Gln Ala Asn
1365                    1370                    1375              1380
```

FIG.1K

```
ACC AGC ATG TAC AGT AAC AAC ATG AAC ATC AAT GTG TCC ATG GCG ACC    4350
Thr Ser Met Tyr Ser Asn Asn Met Asn Ile Asn Val Ser Met Ala Thr
                1385                    1390                1395

AAC ACA GGT GGC ATG AGC AGC ATG AGC AGC ATG AAC CAG ATG ACA GGA CAG ATC AGC    4398
Asn Thr Gly Gly Met Ser Ser Met Asn Gln Met Thr Gly Gln Ile Ser
        1400                    1405                    1410

ATG ACC TCA GTG ACC TCC GTG TCT ACG TCA GGG CTG TCC TCC ATG GGT    4446
Met Thr Ser Val Thr Ser Val Ser Thr Ser Gly Leu Ser Ser Met Gly
            1415                    1420                    1425

CCC GAG CAG GTT AAT GAT CCT GCT CTG AGG GGA GGC AAC CTG TTC CCA    4494
Pro Glu Gln Val Asn Asp Pro Ala Leu Arg Gly Gly Asn Leu Phe Pro
1430                    1435                    1440

AAC CAG CTG CCT GGA ATG GAT ATG ATT AAG CAG GAG GGA GAC ACA ACA    4542
Asn Gln Leu Pro Gly Met Asp Met Ile Lys Gln Glu Gly Asp Thr Thr
1445                    1450                    1455            1460

CGG AAA TAT TGC TGACACTGCT GAAGCCAGTT GCTTCTTCAG CTGACCGGGC    4594
Arg Lys Tyr Cys

TCACTTGCTC AAAACACTTC CAGTCTGGAG AGCTGTGTCT ATTTGTTTCA ACCCAACTGA    4654

CCTGCCAGCC GGTTCTGCTA GAGCAGACAG GCCTGGCCCT GGTTCCCAGG GTGGCGTCCA    4714

CTCGGCTGTG GCAGGAGGAG CTGCCTCTTC TCTTGACAGT CTGAAGCTCG CATCCAGACA    4774

GTCGCTCAGT CTGTTCCCTG CATTCACCTT AGTGCAACTT AGATCTCTCC TCCCCAAGTA    4834
```

FIG.1L

```
AATGTTGACA GGCCAATTTC ATACCATGT CAGATTGAAT GTATTTAAAT GTATGTATTT   4894
AAGGAGAAACC ATGCTCTTGT TCTGTTCCTG TTCGGTTCCA GACACTGGTT TCTTGCTTTG   4954
TTTTCCCTGG CTAACAGTCT AGTGCCAAAG ATTAAGATTT TATCTGGGGG AAAGAAAAGA   5014
ATTTTTTAAA AAATTAAACT AAAGATGTTT TAAGCTAAAG CCTGAATTTG GGATGGAAGC   5074
AGGACAGACA CCGTGGACAG CGCTGTATTT ACAGACACAC CCAGTGCGTG AAGACCAACA   5134
AAGTCACAGT CGTATCTCTA GAAAGCTCTA AAGACCATGT TGGAAAGAGT CTCCAGTTAC   5194
TGAACAGATG AAAAGGAGCC TGTGAGAGGG CTGTTAACAT TAGCAAATAT TTTTTCCTTG   5254
TTTTTCTTT GTTAAAACCA AACTGGTTCA CCTGAATCAT GAATTGAGAA GAAATAATTT   5314
TCATTTCTAA ATTAAGTCCC TTTTAGTTTG ATCAGACAGC TTGAATCAGC ATCTCTTCTT   5374
CCCTGTCAGC CTGACTCTTC CCTTCCCCTC TCTCATTCCC CATACTCCCT ATTTTCATTC   5434
CTTTTTTAAA AAATAATATA AGCTACAGAA ACCAGGTAAG CCCTTTATTT CCTTAAATGT   5494
TTTGCCAGCC ACTTACCAAT TGCTAAGTAT TGAATTTCAG AAAAAAAAAA TGCATTTACT   5554
GGCAAGGAGA AGAACAAAGT TAAGGCTTGA TACCAATCGA GCTAAGGATA CCTGCTTTGG   5614
AAGCATGTTT ATTCTGTTCC CCAGCAACTC TGGCCTCCAA AATGGGAGAA ACGCCAGTGT   5674
GTTTAAATTG ATAGCAGATA TCACGACAGA TTTAACCTCT GCCATGTGTT TTTTATTTTG   5734
TTTTTTAGCA GTGCTGACTA AGCCGAAGTT TTGTAAGGTA CATAAAATCC AATTTATATG   5794
```

FIG. 1M

```
TAAACAAGCA ATAATTTAAG TTGAGAACTT ATGTGTTTTA ATTGTATAAT TTTTGTGAGG    5854
TATACATATT GTGGAATTGA CTCAAAAATG AGGTACTTCA GTATTAAATT AGATATCTTC    5914
ATAGCAATGT CTCCTAAAGG TGTTTTGTAA AGGATATCAA TGCCTTGATT AGACCTAATT    5974
TGTAGACTTA AGACTTTTTA TTTTTCTAAAC CTTGTGATTC TGCTTATAAG TCATTTATCT   6034
AATCTATATG ATATGCAGCC GCTGTAGGAA CCAATTCTTG ATTTTTATAT GTTTATATTC    6094
TTTCTTAATG AACCTTAGAA AGACTACATG TTACTAAGCA GGCCACTTTT ATGGTTGTTT    6154
TT                                                                   6156
```

FIG.1N

```
          NLS              NLS
      TIF2
   1 MSGMGENTSDPSRAE TRKRKE CPDQLGPSPKRNTEKKRNREQENKYIEELAELIFANFNDIDNFNFKPDKCAILKETVKQIRQIKEQEKAAAANIDEVQKS
 101 DVSSTGQQVIDKDALGPMMLEALDGFFFVVNLEGNVVFVSENVTQYLRYNQEELMNKSVYS1LHVGDHTEFVKNLLPKSIVNGGSWSGEPPRRNSHIFNC
 201 RMLVKPLPDSEEEGHDNQEAHQKYETMQCFAVSQPKS1KEEGEDLQSCLICVARRVPMKERPVLPSSESFTTRQDLQGKITSLDTSTMRAAMKPGWEDLV
 301 RRC1QKFHAQHEGESVSYAKRHHEVLRQQLAFSQ1YRFSLSDGTLVAAQTIKSKLIRSQTTNEPQLV1SLHMLHREQNVCVMNPDLTGQTMGKPLNPTSS

MSIPRVNPSVNPSIS.....PAHGVARSSTLPPS
                              SRC-1
 401 NSPAHQALCSGNPGQDMTLSSNINFPINGPKEQMGMPNCRFGCSGGMNHVSGM....QATTPQGSNYALKMNSPSQSSPGWNPGQPTSMLSPRHRMSPGV
  30 NSNMVSTRINRQQSSDLHSSSHSN.........SSNSQCSFGCSPGSQ1VANVALNKGQASSQSSKPSLNLNNPPMEGTGISLAQ..FMSPRRQVTSGL

497 AGSPRIPPSQFSPAGS..LHSPVGVCSST..GNSHSYTNSSLNAL QALSEGHCVSLGSSLASPDLKMGNLQNSPVNMNPPPLSKAMGSLDSKDCFGLYGEPS
 118 ATRPRMPNNSFPPNISTLSSPVGMTSSACNNNNRSYSNIPVTSL QGMNNEGPNNSVGFSASSPVLRQMSSQNSPSRLNIQP.AKAESKDNKEIASILNEMI
      ▲ TIF2.1

594 EGTTGQAESSCHPGEQKETNDPNLPPAVSSERADGQSRLHDSKGQTKLLQLLITTKSDQ........MEPSPLASSLSDTNKDSTGSLPGSGSTHCTSLKE
 217 QSDNSSSDGKPLDSGLLHNNDR.........LSDGDSKY..SQTSHKLVQLLITTAEQQLRHADIDTSCKDVLSCTGTSNSASANSSGGSCPSSHSSLTA

686 KHKILHRLLQDSSSPVDLAKLTAEATGKDLSQEESSSTAP..GSEVTIIKQEPVSPKKKE..NALLRYLLDKDD......TKDIGLPEITPKLERLDSKTDP
 306 RHKILHRLLQE.GSPSDITTLSVEPDKKDSASTSVSVTGQVQGNSS.IKLELDASKKKESKDHQLLRYLLDKDEKDLRSTPNLSLDDVKVKVEKKE.QMDP

776 ASNTKLIAMKTEKEEMSFEPGSDQPGSELDNLEEILDDLQN.SQLPQLFPDTRPGAPAGSVDKQAIINDLMQLTAENSPVTPVGAQKTALRISQSTFNNPR
 404 CNTNPTPMTKATPEEIKLEAQSQFTADLDQFDQLLPTILEKAAQLPGLCETDRMDGAVTSVTIKSEI.........TIKSEILPASLQSATAR......
```

RECEPTORS

| | | | |
|---|---|---|---|
| RARα1 | 1 ─────────────── 462<br>[A1\|B\|C\|D\|E/F] | RXRα | 1 ─────────── 467<br>[AB\|C\|D\|E] |
| RARβ2 | 1 ─────────────── 448<br>[A2\|B\|C\|D\|E/F] | RXRβ | 1 ─────────── 448<br>[AB\|C\|D\|E] |
| RARγ1 | 1 ─────────────── 458<br>[A1\|B\|C\|D\|E/F] | RXRγ | 1 ─────────── 463<br>[AB\|C\|D\|E] |
| RARαΔA | 61 ──────────── 462<br>[B\|C\|D\|E/F] | RXRαΔAB | 140 ────── 467<br>[C\|D\|E] |
| RARα1ΔB | 1  60 86 ──── 462<br>[A1]  [C\|D\|E/F] | RXRαC160A | 1  160C→A ── 467<br>[AB\|C\|D\|E] |
| RARαΔAB | 84 ─────────── 462<br>[C\|D\|E/F] | dnRXRα | 1 ─────────── 448<br>[AB\|C\|D\|E] |
| RARα1C88G | 1  880→G ──── 462<br>[A1\|B\|C\|D\|E/F] | dnRXRαΔAB | 140 ────── 448<br>[C\|D\|E] |
| dnRARα1 | 1 ─────────────── 396<br>[A1\|B\|C\|D\|E] | RXRγΔAB | 139 ────── 463<br>[C\|D\|E] |
| RARα1-ER.Cas | 1  83  154 ── 462<br>[A1\|B\|C\|D\|E]<br>RARα1 / ER \ RARα<br>   185  250 | dnRXRβ | 1 ─────────── 429<br>[AB\|C\|D\|E] |
| | | dnRXRβΔAB | 123 ────── 429<br>[C\|D\|E] |

| | | | |
|---|---|---|---|
| RARα1(AB)-ER(C) | 1  87 176 282<br>[A1\|B\|C]<br>RARα1   ER | RXRα(AB)-ER(C) | 1  139 176 282<br>[AB\|C]<br>RXRα  ER |
| RARβ2(AB)-ER(C) | 1  80 176 282<br>[A2\|B\|C]<br>RARγ2   ER | RXRβ(AB)-ER(C) | 1  122 176 282<br>[AB\|C]<br>RXRβ  ER |
| RARγ1(AB)-ER(C) | 1  89 176 282<br>[A1\|B\|C]<br>RARγ1   ER | RXRγ(AB)-ER(C) | 1  138 176 282<br>[AB\|C]<br>RXRγ  ER |

FIG.6B

| WB Cos-1 | GAL-TIF | Fold Induction of (17M)₅-G-CAT | |
| --- | --- | --- | --- |
| | | Cos-1 | HeLa |
| | 2.0 | < 2 | < 2 |
| | 2.1 | 32 ±9 | 14 ±2 |
| | 2.2 | 60 ±5 | 31 ±5 |
| | 2.3 | 172 ±16 | 122 ±19 |
| | 2.4 | < 2 | < 2 |
| | 2.5 | < 2 | < 2 |
| | 2.6 | < 2 | < 2 |
| | 2.8 | 324 ±16 | 1220 ±28 |
| | 2.7 | 300 ±74 | 1002 ±67 |
| | 2.9 | 298 ±19 | 610 ±31 |
| | 2.12 | 592 ±29 | 772 ±16 |

FIG. 7C

```
                   NR box
TIFIα     724  - RSILTSLLLNSS - 735
RIP140    933  - FNVLKQLLLSEN - 944
TRIP3      95  - SATLRSLLLNPH - 106
TIF2(I)   638  - QTKLLQLLTTKS - 648
TIF2(II)  687  - HKILHRLLQDSS - 698
TIF2(III) 742  - NALLRYLLDKDD - 753
```

FIG.8B

| GAL-TIF | Fold Induction of (17m)₅-TATA-CAT | |
|---|---|---|
| | Cos-1 | HeLa |
| 2.13 | 462 ± 9 | 704 ± 33 |
| 2.14 | 392 ± 13 | 674 ± 23 |
| 2.15 | 279 ± 21 | 316 ± 49 |
| 2.16 | 390 ± 34 | 597 ± 54 |
| 2.17 | 389 ± 50 | 581 ± 58 |
| 2.18 | 314 ± 16 | 432 ± 19 |
| 2.19 | 341 ± 67 | 777 ± 30 |
| 2.20 | 107 ± 11 | 314 ± 27 |
| 2.21 | 129 ± 8 | 173 ± 22 |
| 2.24 | < 2 | < 2 |
| 2.27 | < 2 | < 2 |
| 2.29 | < 2 | < 2 |
| 2.30 | 98 ± 13 | 117 ± 6 |
| 2.31 | 35 ± 3 | 34 ± 3 |
| 2.32 | 2.8 ± 0.2 | 5.9 ± 0.9 |
| 2.32(LLL) | 1.4 ± 0.2 | 1.5 ± 0.1 |
| 2.32(DQ) | 1.7 ± 0.3 | 1.2 ± 0.2 |

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
      (A) LENGTH: 6156 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 163..4554

(xi) SEQUENCE DESCRIPTION: SEQ ID NO: 1:

```
GGCGGCCGCA GCCTCGGCTA CAGCTTCGGC GGCGAAGGTC AGCGCCGACG GCAGCCGGCA        60

CCTGACGGCG TGACCGACCC GAGCCGATTT CTCTTGGATT TGGCTACACA CTTATAGATC       120

TTCTGCACTG TTTACAGGCA CAGTTGCTGA TATGTGTTCA AG ATG AGT GGG ATG          174
                                              Met Ser Gly Met
                                                1

GGA GAA AAT ACC TCT GAC CCC TCC AGG GCA GAG ACA AGA AAG CGC AAG        222
Gly Glu Asn Thr Ser Asp Pro Ser Arg Ala Glu Thr Arg Lys Arg Lys
  5                  10                  15                  20
```

```
                                           -continued

GAA TGT CCT GAC CAA CTT GGA CCC AGC CCC AAA AGG AAC ACT GAA AAA        270
Glu Cys Pro Asp Gln Leu Gly Pro Ser Pro Lys Arg Asn Thr Glu Lys
            25                  30                  35

CGT AAT CGT GAA CAG GAA AAT AAA TAT ATA GAA GAA CTT GCA GAG TTG        318
Arg Asn Arg Glu Gln Glu Asn Lys Tyr Ile Glu Glu Leu Ala Glu Leu
                40                  45                  50

ATT TTT GCA AAT TTT AAT GAT ATA GAC AAC TTT AAC TTC AAA CCT GAC        366
Ile Phe Ala Asn Phe Asn Asp Ile Asp Asn Phe Asn Phe Lys Pro Asp
        55                  60                  65

AAA TGT GCA ATC TTA AAA GAA ACT GTG AAG CAA ATT CGT CAG ATC AAA        414
Lys Cys Ala Ile Leu Lys Glu Thr Val Lys Gln Ile Arg Gln Ile Lys
    70                  75                  80

GAA CAA GAG AAA GCA GCA GCT GCC AAC ATA GAT GAA GTG CAG AAG TCA        462
Glu Gln Glu Lys Ala Ala Ala Ala Asn Ile Asp Glu Val Gln Lys Ser
85                  90                  95                  100

GAT GTA TCC TCT ACA GGG CAG GGT GTC ATC GAC AAG GAT GCG CTG GGG        510
Asp Val Ser Ser Thr Gly Gln Gly Val Ile Asp Lys Asp Ala Leu Gly
                105                 110                 115

CCT ATG ATG CTT GAG GCC CTT GAT GGG TTC TTC TTT GTA GTG AAC CTG        558
Pro Met Met Leu Glu Ala Leu Asp Gly Phe Phe Phe Val Val Asn Leu
            120                 125                 130

GAA GGC AAC GTT GTG TTT GTG TCA GAG AAT GTG ACA CAG TAT CTA AGG        606
Glu Gly Asn Val Val Phe Val Ser Glu Asn Val Thr Gln Tyr Leu Arg
        135                 140                 145

TAT AAC CAA GAA GAG CTG ATG AAC AAA AGT GTA TAT AGC ATC TTG CAT        654
Tyr Asn Gln Glu Glu Leu Met Asn Lys Ser Val Tyr Ser Ile Leu His
    150                 155                 160

GTT GGG GAC CAC ACG GAA TTT GTC AAA AAC CTG CTG CCA AAG TCT ATA        702
Val Gly Asp His Thr Glu Phe Val Lys Asn Leu Leu Pro Lys Ser Ile
165                 170                 175                 180

GTA AAT GGG GGA TCT TGG TCT GGC GAA CCT CCG AGG CGG AAC AGC CAT        750
Val Asn Gly Gly Ser Trp Ser Gly Glu Pro Pro Arg Arg Asn Ser His
                185                 190                 195

ACC TTC AAT TGT CGG ATG CTG GTA AAA CCT TTA CCT GAT TCA GAA GAG        798
Thr Phe Asn Cys Arg Met Leu Val Lys Pro Leu Pro Asp Ser Glu Glu
            200                 205                 210

GAG GGT CAT GAT AAC CAG GAA GCT CAT CAG AAA TAT GAA ACT ATG CAG        846
Glu Gly His Asp Asn Gln Glu Ala His Gln Lys Tyr Glu Thr Met Gln
        215                 220                 225

TGC TTC GCT GTC TCT CAA CCA AAG TCC ATC AAA GAA GAA GGA GAA GAT        894
Cys Phe Ala Val Ser Gln Pro Lys Ser Ile Lys Glu Glu Gly Glu Asp
    230                 235                 240

TTG CAG TCC TGC TTG ATT TGC GTG GCA AGA AGA GTT CCC ATG AAG GAA        942
Leu Gln Ser Cys Leu Ile Cys Val Ala Arg Arg Val Pro Met Lys Glu
245                 250                 255                 260

AGA CCA GTT CTT CCC TCA TCA GAA AGT TTT ACT ACT CGC CAG GAT CTC        990
Arg Pro Val Leu Pro Ser Ser Glu Ser Phe Thr Thr Arg Gln Asp Leu
                265                 270                 275

CAA GGC AAG ATC ACG TCT CTG GAT ACC AGC ACC ATG AGA GCA GCC ATG       1038
Gln Gly Lys Ile Thr Ser Leu Asp Thr Ser Thr Met Arg Ala Ala Met
            280                 285                 290

AAA CCA GGC TGG GAG GAC CTG GTA AGA AGG TGT ATT CAG AAG TTC CAT       1086
Lys Pro Gly Trp Glu Asp Leu Val Arg Arg Cys Ile Gln Lys Phe His
        295                 300                 305

GCG CAG CAT GAA GGA GAA TCT GTG TCC TAT GCT AAG AGG CAT CAT CAT       1134
Ala Gln His Glu Gly Glu Ser Val Ser Tyr Ala Lys Arg His His His
    310                 315                 320

GAA GTA CTG AGA CAA GGA TTG GCA TTC AGT CAA ATC TAT CGT TTT TCC       1182
Glu Val Leu Arg Gln Gly Leu Ala Phe Ser Gln Ile Tyr Arg Phe Ser
325                 330                 335                 340
```

|  |  |
|---|---|
| TTG TCT GAT GGC ACT CTT GTT GCT GCA CAA ACG AAG AGC AAA CTC ATC<br>Leu Ser Asp Gly Thr Leu Val Ala Ala Gln Thr Lys Ser Lys Leu Ile<br>                        345                  350                    355 | 1230 |
| CGT TCT CAG ACT ACT AAT GAA CCT CAA CTT GTA ATA TCT TTA CAT ATG<br>Arg Ser Gln Thr Thr Asn Glu Pro Gln Leu Val Ile Ser Leu His Met<br>                        360                  365                    370 | 1278 |
| CTT CAC AGA GAG CAG AAT GTG TGT GTG ATG AAT CCG GAT CTG ACT GGA<br>Leu His Arg Glu Gln Asn Val Cys Val Met Asn Pro Asp Leu Thr Gly<br>                        375                  380                    385 | 1326 |
| CAA ACG ATG GGG AAG CCA CTG AAT CCA ATT AGC TCT AAC AGC CCT GCC<br>Gln Thr Met Gly Lys Pro Leu Asn Pro Ile Ser Ser Asn Ser Pro Ala<br>    390                  395                  400 | 1374 |
| CAT CAG GCC CTG TGC AGT GGG AAC CCA GGT CAG GAC ATG ACC CTC AGT<br>His Gln Ala Leu Cys Ser Gly Asn Pro Gly Gln Asp Met Thr Leu Ser<br>405                  410                  415                  420 | 1422 |
| AGC AAT ATA AAT TTT CCC ATA AAT GGC CCA AAG GAA CAA ATG GGC ATG<br>Ser Asn Ile Asn Phe Pro Ile Asn Gly Pro Lys Glu Gln Met Gly Met<br>                        425                  430                    435 | 1470 |
| CCC ATG GGC AGG TTT GGT GGT TCT GGG GGA ATG AAC CAT GTG TCA GGC<br>Pro Met Gly Arg Phe Gly Gly Ser Gly Gly Met Asn His Val Ser Gly<br>            440                  445                  450 | 1518 |
| ATG CAA GCA ACC ACT CCT CAG GGT AGT AAC TAT GCA CTC AAA ATG AAC<br>Met Gln Ala Thr Thr Pro Gln Gly Ser Asn Tyr Ala Leu Lys Met Asn<br>                        455                  460                    465 | 1566 |
| AGC CCC TCA CAA AGC AGC CCT GGC ATG AAT CCA GGA CAG CCC ACC TCC<br>Ser Pro Ser Gln Ser Ser Pro Gly Met Asn Pro Gly Gln Pro Thr Ser<br>    470                  475                  480 | 1614 |
| ATG CTT TCA CCA AGG CAT CGC ATG AGC CCT GGA GTG GCT GGC AGC CCT<br>Met Leu Ser Pro Arg His Arg Met Ser Pro Gly Val Ala Gly Ser Pro<br>485                  490                  495                  500 | 1662 |
| CGA ATC CCA CCC AGT CAG TTT TCC CCT GCA GGA AGC TTG CAT TCC CCT<br>Arg Ile Pro Pro Ser Gln Phe Ser Pro Ala Gly Ser Leu His Ser Pro<br>                        505                  510                    515 | 1710 |
| GTG GGA GTT TGC AGC AGC ACA GGA AAT AGC CAT AGT TAT ACC AAC AGC<br>Val Gly Val Cys Ser Ser Thr Gly Asn Ser His Ser Tyr Thr Asn Ser<br>            520                  525                  530 | 1758 |
| TCC CTC AAT GCA CTT CAG GCC CTC AGC GAG GGG CAC GGG GTC TCA TTA<br>Ser Leu Asn Ala Leu Gln Ala Leu Ser Glu Gly His Gly Val Ser Leu<br>                        535                  540                    545 | 1806 |
| GGG TCA TCG TTG GCT TCA CCA GAC CTA AAA ATG GGC AAT TTG CAA AAC<br>Gly Ser Ser Leu Ala Ser Pro Asp Leu Lys Met Gly Asn Leu Gln Asn<br>    550                  555                  560 | 1854 |
| TCC CCA GTT AAT ATG AAT CCT CCC CCA CTC AGC AAG ATG GGA AGC TTG<br>Ser Pro Val Asn Met Asn Pro Pro Pro Leu Ser Lys Met Gly Ser Leu<br>565                  570                  575                  580 | 1902 |
| GAC TCA AAA GAC TGT TTT GGA CTA TAT GGG GAG CCC TCT GAA GGT ACA<br>Asp Ser Lys Asp Cys Phe Gly Leu Tyr Gly Glu Pro Ser Glu Gly Thr<br>                        585                  590                    595 | 1950 |
| ACT GGA CAA GCA GAG AGC AGC TGC CAT CCT GGA GAG CAA AAG GAA ACA<br>Thr Gly Gln Ala Glu Ser Ser Cys His Pro Gly Glu Gln Lys Glu Thr<br>            600                  605                  610 | 1998 |
| AAT GAC CCC AAC CTG CCC CCG GCC GTG AGC AGT GAG AGA GCT GAC GGG<br>Asn Asp Pro Asn Leu Pro Pro Ala Val Ser Ser Glu Arg Ala Asp Gly<br>                        615                  620                    625 | 2046 |
| CAG AGC AGA CTG CAT GAC AGC AAA GGG CAG ACC AAA CTC CTG CAG CTG<br>Gln Ser Arg Leu His Asp Ser Lys Gly Gln Thr Lys Leu Leu Gln Leu<br>    630                  635                  640 | 2094 |
| CTG ACC ACC AAA TCT GAT CAG ATG GAG CCC TCG CCC TTA GCC AGC TCT<br>Leu Thr Thr Lys Ser Asp Gln Met Glu Pro Ser Pro Leu Ala Ser Ser | 2142 |

```
                                             -continued
645                 650                 655                 660

TTG TCG GAT ACA AAC AAA GAC TCC ACA GGT AGC TTG CCT GGT TCT GGG        2190
Leu Ser Asp Thr Asn Lys Asp Ser Thr Gly Ser Leu Pro Gly Ser Gly
            665                 670                 675

TCT ACA CAT GGA ACC TCG CTC AAG GAG AAG CAT AAA ATT TTG CAC AGA        2238
Ser Thr His Gly Thr Ser Leu Lys Glu Lys His Lys Ile Leu His Arg
            680                 685                 690

CTC TTG CAG GAC AGC AGT TCC CCT GTG GAC TTG GCC AAG TTA ACA GCA        2286
Leu Leu Gln Asp Ser Ser Ser Pro Val Asp Leu Ala Lys Leu Thr Ala
            695                 700                 705

GAA GCC ACA GGC AAA GAC CTG AGC CAG GAG TCC AGC AGC ACA GCT CCT        2334
Glu Ala Thr Gly Lys Asp Leu Ser Gln Glu Ser Ser Thr Ala Pro
            710                 715                 720

GGA TCA GAA GTG ACT ATT AAA CAA GAG CCG GTG AGC CCC AAG AAG AAA        2382
Gly Ser Glu Val Thr Ile Lys Gln Glu Pro Val Ser Pro Lys Lys Lys
725                 730                 735                 740

GAG AAT GCA CTA CTT CGC TAT TTG CTA GAT AAA GAT GAT ACT AAA GAT        2430
Glu Asn Ala Leu Leu Arg Tyr Leu Leu Asp Lys Asp Asp Thr Lys Asp
                745                 750                 755

ATT GGT TTA CCA GAA ATA ACC CCC AAA CTT GAG AGA CTG GAC AGT AAG        2478
Ile Gly Leu Pro Glu Ile Thr Pro Lys Leu Glu Arg Leu Asp Ser Lys
            760                 765                 770

ACA GAT CCT GCC AGT AAC ACA AAA TTA ATA GCA ATG AAA ACT GAG AAG        2526
Thr Asp Pro Ala Ser Asn Thr Lys Leu Ile Ala Met Lys Thr Glu Lys
            775                 780                 785

GAG GAG ATG AGC TTT GAG CCT GGT GAC CAG CCT GGC AGT GAG CTG GAC        2574
Glu Glu Met Ser Phe Glu Pro Gly Asp Gln Pro Gly Ser Glu Leu Asp
            790                 795                 800

AAC TTG GAG GAG ATT TTG GAT GAT TTG CAG AAT AGT CAA TTA CCA CAG        2622
Asn Leu Glu Glu Ile Leu Asp Asp Leu Gln Asn Ser Gln Leu Pro Gln
805                 810                 815                 820

CTT TTC CCA GAC ACG AGG CCA GGC GCC CCT GCT GGA TCA GTT GAC AAG        2670
Leu Phe Pro Asp Thr Arg Pro Gly Ala Pro Ala Gly Ser Val Asp Lys
                825                 830                 835

CAA GCC ATC ATC AAT GAC CTC ATG CAA CTC ACA GCT GAA AAC AGC CCT        2718
Gln Ala Ile Ile Asn Asp Leu Met Gln Leu Thr Ala Glu Asn Ser Pro
            840                 845                 850

GTC ACA CCT GTT GGA GCC CAG AAA ACA GCA CTG CGA ATT TCA CAG AGC        2766
Val Thr Pro Val Gly Ala Gln Lys Thr Ala Leu Arg Ile Ser Gln Ser
            855                 860                 865

ACT TTT AAT AAC CCA CGA CCA GGG CAA CTG GGC AGG TTA TTG CCA AAC        2814
Thr Phe Asn Asn Pro Arg Pro Gly Gln Leu Gly Arg Leu Leu Pro Asn
            870                 875                 880

CAG AAT TTA CCA CTT GAC ATC ACA TTG CAA AGC CCA ACT GGT GCT GGA        2862
Gln Asn Leu Pro Leu Asp Ile Thr Leu Gln Ser Pro Thr Gly Ala Gly
885                 890                 895                 900

CCT TTC CCA CCA ATC AGA AAC AGT AGT CCC TAC TCA GTG ATA CCT CAG        2910
Pro Phe Pro Pro Ile Arg Asn Ser Ser Pro Tyr Ser Val Ile Pro Gln
                905                 910                 915

CCA GGA ATG ATG GGT AAT CAA GGG ATG ATA GGA AAC CAA GGA AAT TTA        2958
Pro Gly Met Met Gly Asn Gln Gly Met Ile Gly Asn Gln Gly Asn Leu
            920                 925                 930

GGG AAC AGT AGC ACA GGA ATG ATT GGT AAC AGT GCT TCT CGG CCT ACT        3006
Gly Asn Ser Ser Thr Gly Met Ile Gly Asn Ser Ala Ser Arg Pro Thr
            935                 940                 945

ATG CCA TCT GGA GAA TGG GCA CCG CAG AGT TCG GCT GTG AGA GTC ACC        3054
Met Pro Ser Gly Glu Trp Ala Pro Gln Ser Ser Ala Val Arg Val Thr
            950                 955                 960

TGT GCT GCT ACC ACC AGT GCC ATG AAC CGG CCA GTC CAA GGA GGT ATG        3102
```

```
                                              -continued

Cys Ala Ala Thr Thr Ser Ala Met Asn Arg Pro Val Gln Gly Gly Met
965                 970                 975                 980

ATT CGG AAC CCA GCA GCC AGC ATC CCC ATG AGG CCC AGC AGC CAG CCT        3150
Ile Arg Asn Pro Ala Ala Ser Ile Pro Met Arg Pro Ser Ser Gln Pro
                    985                 990                 995

GGC CAA AGA CAG ACG CTT CAG TCT CAG GTC ATG AAT ATA GGG CCA TCT        3198
Gly Gln Arg Gln Thr Leu Gln Ser Gln Val Met Asn Ile Gly Pro Ser
                1000                1005                1010

GAA TTA GAG ATG AAC ATG GGG GGA CCT CAG TAT AGC CAA CAA CAA GCT        3246
Glu Leu Glu Met Asn Met Gly Gly Pro Gln Tyr Ser Gln Gln Gln Ala
            1015                1020                1025

CCT CCA AAT CAG ACT GCC CCA TGG CCT GAA AGC ATC CTG CCT ATA GAC        3294
Pro Pro Asn Gln Thr Ala Pro Trp Pro Glu Ser Ile Leu Pro Ile Asp
        1030                1035                1040

CAG GCG TCT TTT GCC AGC CAA AAC AGG CAG CCA TTT GGC AGT TCT CCA        3342
Gln Ala Ser Phe Ala Ser Gln Asn Arg Gln Pro Phe Gly Ser Ser Pro
1045                1050                1055                1060

GAT GAC TTG CTA TGT CCA CAT CCT GCA GCT GAG TCT CCG AGT GAT GAG        3390
Asp Asp Leu Leu Cys Pro His Pro Ala Ala Glu Ser Pro Ser Asp Glu
                1065                1070                1075

GGA GCT CTC CTG GAC CAG CTG TAT CTG GCC TTG CGG AAT TTT GAT GGC        3438
Gly Ala Leu Leu Asp Gln Leu Tyr Leu Ala Leu Arg Asn Phe Asp Gly
                1080                1085                1090

CTG GAG GAG ATT GAT AGA GCC TTA GGA ATA CCC GAA CTG GTC AGC CAG        3486
Leu Glu Glu Ile Asp Arg Ala Leu Gly Ile Pro Glu Leu Val Ser Gln
            1095                1100                1105

AGC CAA GCA GTA GAT CCA GAA CAG TTC TCA AGT CAG GAT TCC AAC ATC        3534
Ser Gln Ala Val Asp Pro Glu Gln Phe Ser Ser Gln Asp Ser Asn Ile
        1110                1115                1120

ATG CTG GAG CAG AAG GCG CCC GTT TTC CCA CAG CAG TAT GCA TCT CAG        3582
Met Leu Glu Gln Lys Ala Pro Val Phe Pro Gln Gln Tyr Ala Ser Gln
1125                1130                1135                1140

GCA CAA ATG GCC CAG GGT AGC TAT TCT CCC ATG CAA GAT CCA AAC TTT        3630
Ala Gln Met Ala Gln Gly Ser Tyr Ser Pro Met Gln Asp Pro Asn Phe
                1145                1150                1155

CAC ACC ATG GGA CAG CGG CCT AGT TAT GCC ACA CTC CGT ATG CAG CCC        3678
His Thr Met Gly Gln Arg Pro Ser Tyr Ala Thr Leu Arg Met Gln Pro
                1160                1165                1170

AGA CCG GGC CTC AGG CCC ACG GGC CTA GTG CAG AAC CAG CCA AAT CAA        3726
Arg Pro Gly Leu Arg Pro Thr Gly Leu Val Gln Asn Gln Pro Asn Gln
            1175                1180                1185

CTA AGA CTT CAA CTT CAG CAT CGC CTC CAA GCA CAG CAG AAT CGC CAG        3774
Leu Arg Leu Gln Leu Gln His Arg Leu Gln Ala Gln Gln Asn Arg Gln
        1190                1195                1200

CCA CTT ATG AAT CAA ATC AGC AAT GTT TCC AAT GTG AAC TTG ACT CTG        3822
Pro Leu Met Asn Gln Ile Ser Asn Val Ser Asn Val Asn Leu Thr Leu
1205                1210                1215                1220

AGG CCT GGA GTA CCA ACA CAG GCA CCT ATT AAT GCA CAG ATG CTG GCC        3870
Arg Pro Gly Val Pro Thr Gln Ala Pro Ile Asn Ala Gln Met Leu Ala
                1225                1230                1235

CAG AGA CAG AGG GAA ATC CTG AAC CAG CAT CTT CGA CAG AGA CAA ATG        3918
Gln Arg Gln Arg Glu Ile Leu Asn Gln His Leu Arg Gln Arg Gln Met
                1240                1245                1250

CAT CAG CAA CAG CAA GTT CAG CAA CGA ACT TTG ATG ATG AGA GGA CAA        3966
His Gln Gln Gln Gln Val Gln Gln Arg Thr Leu Met Met Arg Gly Gln
            1255                1260                1265

GGG TTG AAT ATG ACA CCA AGC ATG GTG GCT CCT AGT GGT ATG CCA GCA        4014
Gly Leu Asn Met Thr Pro Ser Met Val Ala Pro Ser Gly Met Pro Ala
        1270                1275                1280
```

|  |  |
|---|---|
| ACT ATG AGC AAC CCT CGG ATT CCC CAG GCA AAT GCA CAG CAG TTT CCA<br>Thr Met Ser Asn Pro Arg Ile Pro Gln Ala Asn Ala Gln Gln Phe Pro<br>1285                    1290                    1295                    1300 | 4062 |
| TTT CCT CCA AAC TAC GGA ATA AGT CAG CAA CCT GAT CCA GGC TTT ACT<br>Phe Pro Pro Asn Tyr Gly Ile Ser Gln Gln Pro Asp Pro Gly Phe Thr<br>              1305                    1310                    1315 | 4110 |
| GGG GCT ACG ACT CCC CAG AGC CCA CTT ATG TCA CCC CGA ATG GCA CAT<br>Gly Ala Thr Thr Pro Gln Ser Pro Leu Met Ser Pro Arg Met Ala His<br>           1320                    1325                    1330 | 4158 |
| ACA CAG AGT CCC ATG ATG CAA CAG TCT CAG GCC AAC CCA GCC TAT CAG<br>Thr Gln Ser Pro Met Met Gln Gln Ser Gln Ala Asn Pro Ala Tyr Gln<br>                1335                    1340                    1345 | 4206 |
| GCC CCC TCC GAC ATA AAT GGA TGG GCG CAG GGG AAC ATG GGC GGA AAC<br>Ala Pro Ser Asp Ile Asn Gly Trp Ala Gln Gly Asn Met Gly Gly Asn<br>1350                    1355                    1360 | 4254 |
| AGC ATG TTT TCC CAG CAG TCC CCA CCA CAC TTT GGG CAG CAA GCA AAC<br>Ser Met Phe Ser Gln Gln Ser Pro Pro His Phe Gly Gln Gln Ala Asn<br>1365                    1370                    1375                    1380 | 4302 |
| ACC AGC ATG TAC AGT AAC AAC ATG AAC ATC AAT GTG TCC ATG GCG ACC<br>Thr Ser Met Tyr Ser Asn Asn Met Asn Ile Asn Val Ser Met Ala Thr<br>              1385                    1390                    1395 | 4350 |
| AAC ACA GGT GGC ATG AGC AGC ATG AAC CAG ATG ACA GGA CAG ATC AGC<br>Asn Thr Gly Gly Met Ser Ser Met Asn Gln Met Thr Gly Gln Ile Ser<br>                  1400                    1405                    1410 | 4398 |
| ATG ACC TCA GTG ACC TCC GTG TCT ACG TCA GGG CTG TCC TCC ATG GGT<br>Met Thr Ser Val Thr Ser Val Ser Thr Ser Gly Leu Ser Ser Met Gly<br>                      1415                    1420                    1425 | 4446 |
| CCC GAG CAG GTT AAT GAT CCT GCT CTG AGG GGA GGC AAC CTG TTC CCA<br>Pro Glu Gln Val Asn Asp Pro Ala Leu Arg Gly Gly Asn Leu Phe Pro<br>1430                    1435                    1440 | 4494 |
| AAC CAG CTG CCT GGA ATG GAT ATG ATT AAG CAG GAG GGA GAC ACA ACA<br>Asn Gln Leu Pro Gly Met Asp Met Ile Lys Gln Glu Gly Asp Thr Thr<br>1445                    1450                    1455                    1460 | 4542 |
| CGG AAA TAT TGC TGACACTGCT GAAGCCAGTT GCTTCTTCAG CTGACCGGGC<br>Arg Lys Tyr Cys | 4594 |
| TCACTTGCTC AAAACACTTC AGTCTGGAG AGCTGTGTCT ATTTGTTTCA ACCCAACTGA | 4654 |
| CCTGCCAGCC GGTTCTGCTA GAGCAGACAG GCCTGGCCCT GGTTCCCAGG GTGGCGTCCA | 4714 |
| CTCGGCTGTG GCAGGAGGAG CTGCCTCTTC TCTTGACAGT CTGAAGCTCG CATCCAGACA | 4774 |
| GTCGCTCAGT CTGTTCCCTG CATTCACCTT AGTGCAACTT AGATCTCTCC TCCCCAAGTA | 4834 |
| AATGTTGACA GGCCAATTTC ATACCCATGT CAGATTGAAT GTATTTAAAT GTATGTATTT | 4894 |
| AAGGAGAACC ATGCTCTTGT TCTGTTCCTG TTCGGTTCCA GACACTGGTT TCTTGCTTTG | 4954 |
| TTTTCCCTGG CTAACAGTCT AGTGCCAAAG ATTAAGATTT TATCTGGGGG AAAGAAAAGA | 5014 |
| ATTTTTAAA AAATTAAACT AAAGATGTTT TAAGCTAAAG CCTGAATTTG GGATGGAAGC | 5074 |
| AGGACAGACA CCGTGGACAG CGCTGTATTT ACAGACACAC CCAGTGCGTG AAGACCAACA | 5134 |
| AAGTCACAGT CGTATCTCTA GAAAGCTCTA AAGACCATGT TGGAAAGAGT CTCCAGTTAC | 5194 |
| TGAACAGATG AAAAGGAGCC TGTGAGAGGG CTGTTAACAT TAGCAAATAT TTTTTCCTTG | 5254 |
| TTTTTTCTTT GTTAAAACCA AACTGGTTCA CCTGAATCAT GAATTGAGAA GAAATAATTT | 5314 |
| TCATTTCTAA ATTAAGTCCC TTTTAGTTTG ATCAGACAGC TTGAATCAGC ATCTCTTCTT | 5374 |
| CCCTGTCAGC CTGACTCTTC CCTTCCCCTC TCTCATTCCC CATACTCCCT ATTTTCATTC | 5434 |
| CTTTTTTAAA AATAATATA AGCTACAGAA ACCAGGTAAG CCCTTTATTT CCTTAAATGT | 5494 |
| TTTGCCAGCC ACTTACCAAT TGCTAAGTAT TGAATTTCAG AAAAAAAAAA TGCATTTACT | 5554 |
| GGCAAGGAGA AGAGCAAAGT TAAGGCTTGA TACCAATCGA GCTAAGGATA CCTGCTTTGG | 5614 |

-continued

```
AAGCATGTTT ATTCTGTTCC CCAGCAACTC TGGCCTCCAA AATGGGAGAA ACGCCAGTGT      5674

GTTTAAATTG ATAGCAGATA TCACGACAGA TTTAACCTCT GCCATGTGTT TTTTATTTTG      5734

TTTTTTAGCA GTGCTGACTA AGCCGAAGTT TTGTAAGGTA CATAAAATCC AATTTATATG      5794

TAAACAAGCA ATAATTTAAG TTGAGAACTT ATGTGTTTTA ATTGTATAAT TTTTGTGAGG      5854

TATACATATT GTGGAATTGA CTCAAAAATG AGGTACTTCA GTATTAAATT AGATATCTTC      5914

ATAGCAATGT CTCCTAAAGG TGTTTTGTAA AGGATATCAA TGCCTTGATT AGACCTAATT      5974

TGTAGACTTA AGACTTTTTA TTTTCTAAAC CTTGTGATTC TGCTTATAAG TCATTTATCT      6034

AATCTATATG ATATGCAGCC GCTGTAGGAA CCAATTCTTG ATTTTTATAT GTTTATATTC      6094

TTTCTTAATG AACCTTAGAA AGACTACATG TTACTAAGCA GGCCACTTTT ATGGTTGTTT      6154

TT                                                                    6156
```

(2) INFORMATION FOR SEQ ID NO: 2:

(i) SEQUENCE CHARACTERISTICS:
        (A) LENGTH: 1464 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ser Gly Met Gly Glu Asn Thr Ser Asp Pro Ser Arg Ala Glu Thr
  1               5                  10                  15

Arg Lys Arg Lys Glu Cys Pro Asp Gln Leu Gly Ser Pro Lys Arg
                 20                  25                  30

Asn Thr Glu Lys Arg Asn Arg Glu Gln Glu Asn Lys Tyr Ile Glu Glu
             35                  40                  45

Leu Ala Glu Leu Ile Phe Ala Asn Phe Asn Asp Ile Asp Asn Phe Asn
         50                  55                  60

Phe Lys Pro Asp Lys Cys Ala Ile Leu Lys Glu Thr Val Lys Gln Ile
 65                  70                  75                  80

Arg Gln Ile Lys Glu Gln Glu Lys Ala Ala Ala Ala Asn Ile Asp Glu
                 85                  90                  95

Val Gln Lys Ser Asp Val Ser Ser Thr Gly Gln Gly Val Ile Asp Lys
                100                 105                 110

Asp Ala Leu Gly Pro Met Met Leu Glu Ala Leu Asp Gly Phe Phe Phe
            115                 120                 125

Val Val Asn Leu Glu Gly Asn Val Val Phe Val Ser Glu Asn Val Thr
        130                 135                 140

Gln Tyr Leu Arg Tyr Asn Gln Glu Glu Leu Met Asn Lys Ser Val Tyr
145                 150                 155                 160

Ser Ile Leu His Val Gly Asp His Thr Glu Phe Val Lys Asn Leu Leu
                165                 170                 175

Pro Lys Ser Ile Val Asn Gly Gly Ser Trp Ser Gly Glu Pro Pro Arg
            180                 185                 190

Arg Asn Ser His Thr Phe Asn Cys Arg Met Leu Val Lys Pro Leu Pro
        195                 200                 205

Asp Ser Glu Glu Glu Gly His Asp Asn Gln Glu Ala His Gln Lys Tyr
    210                 215                 220

Glu Thr Met Gln Cys Phe Ala Val Ser Gln Pro Lys Ser Ile Lys Glu
225                 230                 235                 240

Glu Gly Glu Asp Leu Gln Ser Cys Leu Ile Cys Val Ala Arg Arg Val
```

-continued

```
                245                 250                 255
Pro Met Lys Glu Arg Pro Val Leu Pro Ser Ser Glu Ser Phe Thr Thr
            260                 265                 270
Arg Gln Asp Leu Gln Gly Lys Ile Thr Ser Leu Asp Thr Ser Thr Met
        275                 280                 285
Arg Ala Ala Met Lys Pro Gly Trp Glu Asp Leu Val Arg Arg Cys Ile
    290                 295                 300
Gln Lys Phe His Ala Gln His Glu Gly Glu Ser Val Ser Tyr Ala Lys
305                 310                 315                 320
Arg His His His Glu Val Leu Arg Gln Gly Leu Ala Phe Ser Gln Ile
                325                 330                 335
Tyr Arg Phe Ser Leu Ser Asp Gly Thr Leu Val Ala Ala Gln Thr Lys
            340                 345                 350
Ser Lys Leu Ile Arg Ser Gln Thr Thr Asn Glu Pro Gln Leu Val Ile
        355                 360                 365
Ser Leu His Met Leu His Arg Glu Gln Asn Val Cys Val Met Asn Pro
    370                 375                 380
Asp Leu Thr Gly Gln Thr Met Gly Lys Pro Leu Asn Pro Ile Ser Ser
385                 390                 395                 400
Asn Ser Pro Ala His Gln Ala Leu Cys Ser Gly Asn Pro Gly Gln Asp
                405                 410                 415
Met Thr Leu Ser Ser Asn Ile Asn Phe Pro Ile Asn Gly Pro Lys Glu
            420                 425                 430
Gln Met Gly Met Pro Met Gly Arg Phe Gly Ser Gly Gly Met Asn
        435                 440                 445
His Val Ser Gly Met Gln Ala Thr Thr Pro Gln Gly Ser Asn Tyr Ala
    450                 455                 460
Leu Lys Met Asn Ser Pro Ser Gln Ser Ser Pro Gly Met Asn Pro Gly
465                 470                 475                 480
Gln Pro Thr Ser Met Leu Ser Pro Arg His Arg Met Ser Pro Gly Val
                485                 490                 495
Ala Gly Ser Pro Arg Ile Pro Pro Ser Gln Phe Ser Pro Ala Gly Ser
            500                 505                 510
Leu His Ser Pro Val Gly Val Cys Ser Ser Thr Gly Asn Ser His Ser
        515                 520                 525
Tyr Thr Asn Ser Ser Leu Asn Ala Leu Gln Ala Leu Ser Glu Gly His
    530                 535                 540
Gly Val Ser Leu Gly Ser Ser Leu Ala Ser Pro Asp Leu Lys Met Gly
545                 550                 555                 560
Asn Leu Gln Asn Ser Pro Val Asn Met Asn Pro Pro Leu Ser Lys
                565                 570                 575
Met Gly Ser Leu Asp Ser Lys Asp Cys Phe Gly Leu Tyr Gly Glu Pro
            580                 585                 590
Ser Glu Gly Thr Thr Gly Gln Ala Glu Ser Ser Cys His Pro Gly Glu
        595                 600                 605
Gln Lys Glu Thr Asn Asp Pro Asn Leu Pro Pro Ala Val Ser Ser Glu
    610                 615                 620
Arg Ala Asp Gly Gln Ser Arg Leu His Asp Ser Lys Gly Gln Thr Lys
625                 630                 635                 640
Leu Leu Gln Leu Leu Thr Thr Lys Ser Asp Gln Met Glu Pro Ser Pro
                645                 650                 655
Leu Ala Ser Ser Leu Ser Asp Thr Asn Lys Asp Ser Thr Gly Ser Leu
            660                 665                 670
```

-continued

```
Pro Gly Ser Gly Ser Thr His Gly Thr Ser Leu Lys Glu Lys His Lys
        675                 680                 685

Ile Leu His Arg Leu Leu Gln Asp Ser Ser Pro Val Asp Leu Ala
690                 695                 700

Lys Leu Thr Ala Glu Ala Thr Gly Lys Asp Leu Ser Gln Glu Ser Ser
705                 710                 715                 720

Ser Thr Ala Pro Gly Ser Glu Val Thr Ile Lys Gln Glu Pro Val Ser
                725                 730                 735

Pro Lys Lys Lys Glu Asn Ala Leu Leu Arg Tyr Leu Leu Asp Lys Asp
                740                 745                 750

Asp Thr Lys Asp Ile Gly Leu Pro Glu Ile Thr Pro Lys Leu Glu Arg
                755                 760                 765

Leu Asp Ser Lys Thr Asp Pro Ala Ser Asn Thr Lys Leu Ile Ala Met
770                 775                 780

Lys Thr Glu Lys Glu Glu Met Ser Phe Glu Pro Gly Asp Gln Pro Gly
785                 790                 795                 800

Ser Glu Leu Asp Asn Leu Glu Glu Ile Leu Asp Asp Leu Gln Asn Ser
                805                 810                 815

Gln Leu Pro Gln Leu Phe Pro Asp Thr Arg Pro Gly Ala Pro Ala Gly
                820                 825                 830

Ser Val Asp Lys Gln Ala Ile Ile Asn Asp Leu Met Gln Leu Thr Ala
                835                 840                 845

Glu Asn Ser Pro Val Thr Pro Val Gly Ala Gln Lys Thr Ala Leu Arg
850                 855                 860

Ile Ser Gln Ser Thr Phe Asn Asn Pro Arg Pro Gly Gln Leu Gly Arg
865                 870                 875                 880

Leu Leu Pro Asn Gln Asn Leu Pro Leu Asp Ile Thr Leu Gln Ser Pro
                885                 890                 895

Thr Gly Ala Gly Pro Phe Pro Pro Ile Arg Asn Ser Ser Pro Tyr Ser
                900                 905                 910

Val Ile Pro Gln Pro Gly Met Met Gly Asn Gln Gly Met Ile Gly Asn
                915                 920                 925

Gln Gly Asn Leu Gly Asn Ser Ser Thr Gly Met Ile Gly Asn Ser Ala
930                 935                 940

Ser Arg Pro Thr Met Pro Ser Gly Glu Trp Ala Pro Gln Ser Ser Ala
945                 950                 955                 960

Val Arg Val Thr Cys Ala Ala Thr Thr Ser Ala Met Asn Arg Pro Val
                965                 970                 975

Gln Gly Gly Met Ile Arg Asn Pro Ala Ala Ser Ile Pro Met Arg Pro
                980                 985                 990

Ser Ser Gln Pro Gly Gln Arg Gln Thr Leu Gln Ser Gln Val Met Asn
                995                 1000                1005

Ile Gly Pro Ser Glu Leu Glu Met Asn Met Gly Gly Pro Gln Tyr Ser
        1010                1015                1020

Gln Gln Gln Ala Pro Pro Asn Gln Thr Ala Pro Trp Pro Glu Ser Ile
1025                1030                1035                1040

Leu Pro Ile Asp Gln Ala Ser Phe Ala Ser Gln Asn Arg Gln Pro Phe
                1045                1050                1055

Gly Ser Ser Pro Asp Asp Leu Leu Cys Pro His Pro Ala Ala Glu Ser
                1060                1065                1070

Pro Ser Asp Glu Gly Ala Leu Leu Asp Gln Leu Tyr Leu Ala Leu Arg
                1075                1080                1085
```

-continued

```
Asn Phe Asp Gly Leu Glu Glu Ile Asp Arg Ala Leu Gly Ile Pro Glu
    1090                1095                1100
Leu Val Ser Gln Ser Gln Ala Val Asp Pro Glu Gln Phe Ser Ser Gln
1105                1110                1115                1120
Asp Ser Asn Ile Met Leu Glu Gln Lys Ala Pro Val Phe Pro Gln Gln
            1125                1130                1135
Tyr Ala Ser Gln Ala Gln Met Ala Gln Gly Ser Tyr Ser Pro Met Gln
            1140                1145                1150
Asp Pro Asn Phe His Thr Met Gly Gln Arg Pro Ser Tyr Ala Thr Leu
            1155                1160                1165
Arg Met Gln Pro Arg Pro Gly Leu Arg Pro Thr Gly Leu Val Gln Asn
    1170                1175                1180
Gln Pro Asn Gln Leu Arg Leu Gln Leu Gln His Arg Leu Gln Ala Gln
1185                1190                1195                1200
Gln Asn Arg Gln Pro Leu Met Asn Gln Ile Ser Asn Val Ser Asn Val
            1205                1210                1215
Asn Leu Thr Leu Arg Pro Gly Val Pro Thr Gln Ala Pro Ile Asn Ala
            1220                1225                1230
Gln Met Leu Ala Gln Arg Gln Arg Glu Ile Leu Asn Gln His Leu Arg
            1235                1240                1245
Gln Arg Gln Met His Gln Gln Gln Val Gln Gln Arg Thr Leu Met
1250                1255                1260
Met Arg Gly Gln Gly Leu Asn Met Thr Pro Ser Met Val Ala Pro Ser
1265                1270                1275                1280
Gly Met Pro Ala Thr Met Ser Asn Pro Arg Ile Pro Gln Ala Asn Ala
            1285                1290                1295
Gln Gln Phe Pro Phe Pro Pro Asn Tyr Gly Ile Ser Gln Gln Pro Asp
            1300                1305                1310
Pro Gly Phe Thr Gly Ala Thr Thr Pro Gln Ser Pro Leu Met Ser Pro
            1315                1320                1325
Arg Met Ala His Thr Gln Ser Pro Met Met Gln Gln Ser Gln Ala Asn
    1330                1335                1340
Pro Ala Tyr Gln Ala Pro Ser Asp Ile Asn Gly Trp Ala Gln Gly Asn
1345                1350                1355                1360
Met Gly Gly Asn Ser Met Phe Ser Gln Gln Ser Pro Pro His Phe Gly
            1365                1370                1375
Gln Gln Ala Asn Thr Ser Met Tyr Ser Asn Asn Met Asn Ile Asn Val
            1380                1385                1390
Ser Met Ala Thr Asn Thr Gly Gly Met Ser Ser Met Asn Gln Met Thr
            1395                1400                1405
Gly Gln Ile Ser Met Thr Ser Val Thr Ser Val Ser Thr Ser Gly Leu
    1410                1415                1420
Ser Ser Met Gly Pro Glu Gln Val Asn Asp Pro Ala Leu Arg Gly Gly
1425                1430                1435                1440
Asn Leu Phe Pro Asn Gln Leu Pro Gly Met Asp Met Ile Lys Gln Glu
            1445                1450                1455
Gly Asp Thr Thr Arg Lys Tyr Cys
            1460
```

(2) INFORMATION FOR SEQ ID NO: 3:

(i) SEQUENCE CHARACTERISTICS:
        (A) LENGTH: 1036 amino acids
        (B) TYPE: amino acid
        (C) STRANDEDNESS: single -continued (D) TOPOLOGY: not relevant (ii) MOLECULE TYPE: peptide (xi) SEQUENCE DESCRIPTION: SEQ ID NO: 3:

```
Met Ser Ile Pro Arg Val Asn Pro Ser Val Asn Pro Ser Ile Ser Pro
1               5                   10                  15

Ala His Gly Val Ala Arg Ser Ser Thr Leu Pro Pro Ser Asn Ser Asn
            20                  25                  30

Met Val Ser Thr Arg Ile Asn Arg Gln Gln Ser Ser Asp Leu His Ser
            35                  40                  45

Ser Ser His Ser Asn Ser Ser Asn Ser Gln Gly Ser Phe Gly Cys Ser
        50                  55                  60

Pro Gly Ser Gln Ile Val Ala Asn Val Ala Leu Asn Lys Gly Gln Ala
65                  70                  75                  80

Ser Ser Gln Ser Ser Lys Pro Ser Leu Asn Leu Asn Asn Pro Pro Met
            85                  90                  95

Glu Gly Thr Gly Ile Ser Leu Ala Gln Phe Met Ser Pro Arg Arg Gln
            100                 105                 110

Val Thr Ser Gly Leu Ala Thr Arg Pro Arg Met Pro Asn Asn Ser Phe
            115                 120                 125

Pro Pro Asn Ile Ser Thr Leu Ser Ser Pro Val Gly Met Thr Ser Ser
130                 135                 140

Ala Cys Asn Asn Asn Arg Ser Tyr Ser Asn Ile Pro Val Thr Ser
145                 150                 155                 160

Leu Gln Gly Met Asn Glu Gly Pro Asn Asn Ser Val Gly Phe Ser Ala
            165                 170                 175

Ser Ser Pro Val Leu Arg Gln Met Ser Ser Gln Asn Ser Pro Ser Arg
            180                 185                 190

Leu Asn Ile Gln Pro Ala Lys Ala Glu Ser Lys Asp Asn Lys Glu Ile
            195                 200                 205

Ala Ser Thr Leu Asn Glu Met Ile Gln Ser Asp Asn Ser Ser Ser Asp
            210                 215                 220

Gly Lys Pro Leu Asp Ser Gly Leu Leu His Asn Asn Asp Arg Leu Ser
225                 230                 235                 240

Asp Gly Asp Ser Lys Tyr Ser Gln Thr Ser His Lys Leu Val Gln Leu
            245                 250                 255

Leu Thr Thr Thr Ala Glu Gln Gln Leu Arg His Ala Asp Ile Asp Thr
            260                 265                 270

Ser Cys Lys Asp Val Leu Ser Cys Thr Gly Thr Ser Asn Ser Ala Ser
            275                 280                 285

Ala Asn Ser Ser Gly Gly Ser Cys Pro Ser Ser His Ser Ser Leu Thr
            290                 295                 300

Ala Arg His Lys Ile Leu His Arg Leu Leu Gln Glu Gly Ser Pro Ser
305                 310                 315                 320

Asp Ile Thr Thr Leu Ser Val Glu Pro Asp Lys Lys Asp Ser Ala Ser
            325                 330                 335

Thr Ser Val Ser Val Thr Gly Gln Val Gln Gly Asn Ser Ser Ile Lys
            340                 345                 350

Leu Glu Leu Asp Ala Ser Lys Lys Glu Ser Lys Asp His Gln Leu
            355                 360                 365

Leu Arg Tyr Leu Leu Asp Lys Asp Glu Lys Asp Leu Arg Ser Thr Pro
            370                 375                 380

Asn Leu Ser Leu Asp Asp Val Lys Val Lys Val Glu Lys Lys Glu Gln
```

-continued

```
        385                 390                 395                 400
Met Asp Pro Cys Asn Thr Asn Pro Thr Pro Met Thr Lys Ala Thr Pro
                    405                 410                 415
Glu Glu Ile Lys Leu Glu Ala Gln Ser Gln Phe Thr Ala Asp Leu Asp
                420                 425                 430
Gln Phe Asp Gln Leu Leu Pro Thr Leu Glu Lys Ala Ala Gln Leu Pro
            435                 440                 445
Gly Leu Cys Glu Thr Asp Arg Met Asp Gly Ala Val Thr Ser Val Thr
        450                 455                 460
Ile Lys Ser Glu Ile Thr Ile Lys Ser Glu Ile Leu Pro Ala Ser Leu
465                 470                 475                 480
Gln Ser Ala Thr Ala Arg Pro Thr Ser Arg Leu Asn Arg Leu Pro Glu
                485                 490                 495
Leu Glu Leu Glu Ala Ile Asp Asn Gln Phe Gly Gln Pro Gly Thr Gly
                500                 505                 510
Asp Gln Ile Pro Trp Thr Asn Asn Thr Val Thr Ala Ile Asn Gln Ser
            515                 520                 525
Lys Ser Glu Asp Gln Cys Ile Ser Ser Gln Leu Asp Glu Leu Leu Cys
530                 535                 540
Pro Pro Thr Thr Val Glu Gly Arg Asn Asp Glu Lys Ala Leu Leu Glu
545                 550                 555                 560
Gln Leu Val Ser Phe Leu Ser Gly Lys Asp Glu Thr Glu Leu Ala Glu
                565                 570                 575
Leu Asp Arg Ala Leu Gly Ile Asp Lys Leu Val Gln Gly Gly Gly Leu
            580                 585                 590
Asp Val Leu Ser Glu Arg Phe Pro Pro Gln Ala Thr Pro Pro Leu
            595                 600                 605
Ile Met Glu Glu Arg Pro Asn Leu Tyr Ser Gln Pro Tyr Ser Ser Pro
        610                 615                 620
Phe Pro Thr Ala Asn Leu Pro Ser Pro Phe Gln Gly Met Val Arg Gln
625                 630                 635                 640
Lys Pro Ser Leu Gly Thr Met Pro Val Gln Val Thr Pro Pro Arg Gly
                645                 650                 655
Ala Phe Ser Pro Gly Met Gly Met Gln Pro Arg Gln Thr Leu Asn Arg
                660                 665                 670
Pro Pro Ala Ala Pro Asn Gln Leu Arg Leu Gln Leu Gln Gln Arg Leu
            675                 680                 685
Gln Gly Gln Gln Leu Ile His Gln Asn Arg Gln Ala Ile Leu Asn
        690                 695                 700
Gln Phe Ala Ala Thr Ala Pro Val Gly Ile Asn Met Arg Ser Gly Met
705                 710                 715                 720
Gln Gln Gln Ile Thr Pro Gln Pro Pro Leu Asn Ala Gln Met Leu Ala
                725                 730                 735
Gln Arg Gln Arg Glu Leu Tyr Ser Gln Gln His Arg Gln Arg Gln Leu
                740                 745                 750
Ile Gln Gln Gln Arg Ala Met Leu Met Arg Gln Gln Ser Phe Gly Asn
            755                 760                 765
Asn Leu Pro Pro Ser Ser Gly Leu Pro Val Gln Thr Gly Asn Pro Arg
        770                 775                 780
Leu Pro Gln Gly Ala Pro Gln Gln Phe Pro Tyr Pro Pro Asn Tyr Gly
785                 790                 795                 800
Thr Asn Pro Gly Thr Pro Pro Ala Ser Thr Ser Pro Phe Ser Gln Leu
                805                 810                 815
```

-continued

```
Ala Ala Asn Pro Glu Ala Ser Leu Ala Asn Arg Asn Ser Met Val Ser
            820                 825                 830
Arg Gly Met Thr Gly Asn Ile Gly Gly Gln Phe Gly Thr Gly Ile Asn
            835                 840                 845
Pro Gln Met Gln Gln Asn Val Phe Gln Tyr Pro Gly Ala Gly Met Val
            850                 855                 860
Pro Gln Gly Glu Ala Asn Phe Ala Pro Ser Leu Ser Pro Gly Ser Ser
865                 870                 875                 880
Met Val Pro Met Pro Ile Pro Pro Gln Ser Ser Leu Leu Gln Gln
                    885                 890                 895
Thr Pro Pro Ala Ser Gly Tyr Gln Ser Pro Asp Met Lys Ala Trp Gln
            900                 905                 910
Gln Gly Ala Ile Gly Asn Asn Val Phe Ser Gln Ala Val Gln Asn
            915                 920                 925
Gln Pro Thr Pro Ala Gln Pro Gly Val Tyr Asn Asn Met Ser Ile Thr
            930                 935                 940
Val Ser Met Ala Gly Gly Asn Thr Asn Val Gln Asn Met Asn Pro Met
945                 950                 955                 960
Met Ala Gln Met Gln Met Ser Ser Leu Gln Met Pro Gly Met Asn Thr
                    965                 970                 975
Val Cys Pro Glu Gln Ile Asn Asp Pro Ala Leu Arg His Thr Gly Leu
            980                 985                 990
Tyr Cys Asn Gln Leu Ser Ser Thr Asp Leu Leu Lys Thr Glu Ala Asp
            995                 1000                1005
Gly Thr Gln Gln Val Gln Gln Val Gln Val Phe Ala Asp Val Gln Cys
   1010                 1015                1020
Thr Val Asn Leu Val Gly Gly Asp Pro Tyr Leu Asn
1025                1030                1035

(2) INFORMATION FOR SEQ ID NO: 4:

(i) SEQUENCE CHARACTERISTICS:
        (A) LENGTH: 21 amino acids
        (B) TYPE: amino acid
        (C) STRANDEDNESS: single
        (D) TOPOLOGY: not relevant (ii) MOLECULE TYPE: peptide (xi) SEQUENCE DESCRIPTION: SEQ ID NO: 4:

Glu Arg Ala Asp Gly Gln Ser Arg Leu His Asp Ser Lys Gly Gln Thr
1               5                   10                  15
Lys Leu Leu Gln Cys
            20

(2) INFORMATION FOR SEQ ID NO: 5:

(i) SEQUENCE CHARACTERISTICS:
        (A) LENGTH: 48 amino acids
        (B) TYPE: amino acid
        (C) STRANDEDNESS: single
        (D) TOPOLOGY: not relevant (ii) MOLECULE TYPE: peptide (xi) SEQUENCE DESCRIPTION: SEQ ID NO: 5:

Gly His Lys Lys Leu Leu Gln Leu Leu Thr Cys Ser Ser His Gly Ser
1               5                   10                  15
Leu Leu Gln Glu Lys His Arg Ile Leu His Lys Leu Leu Gln Asn Gly
```

```
                    20                  25                  30
Asn Asn Ala Leu Leu Arg Tyr Leu Leu Asp Arg Asp Asp Pro Ser Asp
            35                  40                  45
```

(2) INFORMATION FOR SEQ ID NO: 6:

(i) SEQUENCE CHARACTERISTICS:
        (A) LENGTH: 12 amino acids
        (B) TYPE: amino acid
        (C) STRANDEDNESS: single
        (D) TOPOLOGY: not relevant (ii) MOLECULE TYPE: peptide (xi) SEQUENCE DESCRIPTION: SEQ ID NO: 6:

```
Arg Ser Ile Leu Thr Ser Leu Leu Leu Asn Ser Ser
1               5                   10
```

(2) INFORMATION FOR SEQ ID NO: 7:

(i) SEQUENCE CHARACTERISTICS:
        (A) LENGTH: 12 amino acids
        (B) TYPE: amino acid
        (C) STRANDEDNESS: single
        (D) TOPOLOGY: not relevant (ii) MOLECULE TYPE: peptide (xi) SEQUENCE DESCRIPTION: SEQ ID NO: 7:

```
Phe Asn Val Leu Lys Gln Leu Leu Leu Ser Glu Asn
1               5                   10
```

(2) INFORMATION FOR SEQ ID NO: 8:

(i) SEQUENCE CHARACTERISTICS:
        (A) LENGTH: 12 amino acids
        (B) TYPE: amino acid
        (C) STRANDEDNESS: single
        (D) TOPOLOGY: not relevant (ii) MOLECULE TYPE: peptide (xi) SEQUENCE DESCRIPTION: SEQ ID NO: 8:

```
Ser Ala Thr Leu Arg Ser Leu Leu Leu Asn Pro His
1               5                   10
```

(2) INFORMATION FOR SEQ ID NO: 9:

(i) SEQUENCE CHARACTERISTICS:
        (A) LENGTH: 58 amino acids
        (B) TYPE: amino acid
        (C) STRANDEDNESS: single
        (D) TOPOLOGY: not relevant (ii) MOLECULE TYPE: peptide (xi) SEQUENCE DESCRIPTION: SEQ ID NO: 9:

```
Leu Arg Asn Ser Leu Asp Asp Leu Leu Gly Pro Pro Ser Asn Ala Glu
1               5                   10                  15
Gly Gln Ser Asp Glu Arg Ala Leu Leu Asp Gln Leu His Thr Phe Leu
            20                  25                  30
Ser Asn Thr Asp Ala Thr Gly Leu Glu Glu Ile Asp Arg Ala Leu Gly
            35                  40                  45
Ile Pro Glu Leu Val Asn Gln Gly Gln Ala
        50                  55
```

(2) INFORMATION FOR SEQ ID NO: 10:

(i) SEQUENCE CHARACTERISTICS:
        (A) LENGTH: 64 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 10:

```
AGACCTGTTG AACTTTGCAA AGGCAAGGGC AGTTCCTTTG AGCTGGGCTT ATGACCTTTG      60

ACTC                                                                  64
```

(2) INFORMATION FOR SEQ ID NO: 11:

(i) SEQUENCE CHARACTERISTICS:
        (A) LENGTH: 38 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 11:

```
CGGAGGACAG TCCTCCGGCG GCCGCGGTCA CAGTGACC                              38
```

(2) INFORMATION FOR SEQ ID NO: 12:

(i) SEQUENCE CHARACTERISTICS:
        (A) LENGTH: 5 amino acids
        (B) TYPE: amino acid
        (C) STRANDEDNESS: single
        (D) TOPOLOGY: not relevant (ii) MOLECULE TYPE: peptide (xi) SEQUENCE DESCRIPTION: SEQ ID NO: 12:

```
Leu Xaa Xaa Leu Leu
1               5
```

(2) INFORMATION FOR SEQ ID NO: 13:

(i) SEQUENCE CHARACTERISTICS:
        (A) LENGTH: 6 amino acids
        (B) TYPE: amino acid
        (C) STRANDEDNESS: single
        (D) TOPOLOGY: not relevant (ii) MOLECULE TYPE: peptide (xi) SEQUENCE DESCRIPTION: SEQ ID NO: 13:

```
Leu Xaa Xaa Leu Leu Leu
1               5
```

(2) INFORMATION FOR SEQ ID NO: 14:

(i) SEQUENCE CHARACTERISTICS:
        (A) LENGTH: 9 amino acids
        (B) TYPE: amino acid
        (C) STRANDEDNESS: single
        (D) TOPOLOGY: not relevant (ii) MOLECULE TYPE: peptide (xi) SEQUENCE DESCRIPTION: SEQ ID NO: 14:

```
Leu Leu Xaa Xaa Leu Xaa Xaa Xaa Leu
1               5
```

TRANSCRIPTIONAL INTERMEDIARY FACTOR-2

This application is a divisional of U.S. application Ser. No. 08/891,640, filed Jul. 11, 1997; said Ser. No. 08/891,640 claims priority to U.S. application Ser. No. 60/021,247, filed Jul. 12, 1996, the disclosures of both of which are herein incorporated by reference.

FIELD OF THE INVENTION

The present invention relates to a nuclear receptor (NR) transcriptional mediator. More specifically, isolated nucleic acid molecules are provided encoding transcriptional intermediary factor-2 (TIF2). Recombinant methods for making TIF2 polypeptides are also provided as are screening methods for identifying agonists and antagonists of the activation function AF-2 of nuclear receptors, as well as TIF2 antibodies. Also provided are screening methods for identifying agonists and antagonists of TIF2 AD1 activation domain activity, as are provided screening methods for identifying agonists and antagonists of TIF2 AD2 activation domain activity.

BACKGROUND OF THE INVENTION

Activators that enhance the initiation of transcription by RNA polymerase B (II) are composed of at least two functional domains: a DNA binding domain and an activating domain (M. Ptashne, Nature 335:683–689 (1988); P. J. Mitchell et al., Science 245:371–378 (1989)). These two domains are generally separable functional units and each can actually be interchanged with the complementary region of an unrelated activator, thereby creating functional chimeric activators (S. Green et al., Nature 325:75–78 (1987)).

A number of structure-function analyses of eukaryotic transcriptional activators have been performed, focussing primarily on the yeast GAL4 and GCN4 proteins and on members of the nuclear receptor family. GAL4 and GCN4 proteins activate transcription by binding to specific upstream activation sequence, which have many of the characteristics of higher eukaryotic enhancer elements (K. Struhl, Cell 49:295–297 (1987)). The herpes simplex activator VP16 represents another type of activator, which activates transcription by binding to the DNA-bound octamer transcription factor rather than binding to the DNA directly (T. Gerster et al., Proc. Natl. Acad. Sci. USA 85:6347–6351 (1988)).

The nuclear receptor family, which includes receptors for steroid hormones, thyroid hormones, vitamin D, and the vitamin A derivative retinoic acid, are also transcriptional enhancer factors which bind DNA directly in the presence of their cognate ligand by recognition of specific enhancer elements, i.e., hormone- or ligand-responsive elements (R. M. Evans, Cell 240:889–895 (1988)). These cognate ligands tend to be small, hydrophobic molecules, including steroid hormones such as estrogen and progesterone, thyroid hormone, vitamin D, and various retinoids (S. Halachmi et al., Science 264:1455–1458 (1994); Gronemeyer, H. and Laudet, V., Protein Profile 2:1173–1308 (1995)).

Despite their small size and apparently simple structure, however, the cognate ligands associated with NRs are known to elicit a wide range of physiological responses. Adrenal steroids for example, such as cortisol and aldosterone, widely influence body homeostasis, controlling glycogen and mineral metabolism, have widespread effects on the immune and nervous systems, and influence the growth and differentiation of cultured cells. The sex hormones (progesterone, estrogen and testosterone) provoke the development and determination of the embryonic reproductive system, masculinize/feminize the brain at birth, control reproduction and related behavior in adults and are responsible for development of secondary sex characteristics. Vitamin D is necessary for proper bone development and plays a critical role in calcium metabolism and bone differentiation. Significantly, aberrant production of these hormones has been associated with a broad spectrum of clinical disease, including cancer and similar pathologic conditions.

All NRs display a modular structure, with five to six distinct regions, termed A–F. The N-terminal A/B region contains the activation function AF-1, which can activate transcription constitutively. Region C encompasses the DNA binding domain (DBD), which recognizes cognate cis-acting elements. Region E contains the ligand-binding domain (LBD), a dimerization surface and the ligand-dependent transcriptional activation function AF-2 (reviewed in Mangelsdorft, D. J. et al., Cell 83:835–839 (1995a); Mangelsdorft & Evans, Cell 83:841–850 (1995b); Beato, M. et al., Cell 83:851–857 (1995); Gronemeyer & Laudet, "Transcription Factors 3: Nuclear Receptors", in Protein Profile, vol. 2, Academic Press (1995); Kastner, P. et al, EMBO J. 11:629–642 (1992); Chambon, P., FASEB J 10:940–954 (1996)).

Several classes of domains in activators are capable of mediating transcriptional activation. Yeast activators GAL4 and GCN4 and herpes simplex VP16 all contain activation domains that are composed of acidic stretches of amino acids, which may act by forming amphipathic a helices (I. A. Hope et al., Cell 46:885–894 (1986); J. Ma et al, Cell 48:847–853 (1987); E. Giniger et al., Nature 330:670–672 (1987); S. J. Triezenberg et al, Genes Dev. 2:718–729 (1988)). The activation functions of human Sp1 and CTF/NFI proteins contain glutamine- and proline-rich areas, respectively (A. J. Courey et al., Cell 55:887–898 (1988); N. Mermod et al., Cell 58:741–753 (1989)). Studies with steroid hormone receptors have shown that both the N-terminal A/B domain and the C-terminal hormone binding domain (RBD) contain transcription activation functions (AFs) (M. T. Bocquel et al., Nucl. Acids Res., 17:2581–2595 (1989); L. Tora et al, Cell 59:477487 (1989)). The AFs of the human estrogen receptor (hER) do not contain stretches of acidic amino acids (S. Halachmi et al., Science 264:1455–1458 (1994)). Conversely, however, the human glucocorticoid receptor (hGR) contains two activation functions, τ-1 (located in the A/B domain) and τ-2 (located in the N-terminal region of the HBD), both of which are acidic (S. M. Hollenberg et al., Cell 55:899–906 (1988)).

From the results of studies on transcriptional interference/squelching between nuclear receptors and on homo- and heterosynergistic stimulation of initiation of transcription from minimal promoters by the activation functions present in hER (AF-1 and AF-2) and the acidic activator VP16, it has been proposed that AFs may activate transcription by interacting with different components of the basic initiation complex (Bocquel et al., Nucl. Acids. Res. 17:2581–2595 (1989); Meyer et al., Cell 57:433–442 (1989); L. Tora et al., Cell 59:477487 (1989)). Studies of the transcriptional interference/squelching properties of AADs, hER AF-1 and hER AF-2, however, showed that both hER AF-1 and AF-2 can squelch acidic activators, such as VP 16, but that the converse was not true, i.e., AADs do not squelch hER AF-1 or AF-2. Moreover, hER AF-1 and AF-2, which are clearly distinguished by their synergistic properties, nevertheless squelch each other (D. Tasset et al., Cell 62:1177–1187 (1990)).

Based on these results, it was proposed that a string of transcriptional intermediary factors (TIFs) exists, interposed between enhancer factors and the basic transcriptional factors. For example, AF-1 and AF-2 have been suggested to contact the string of TIFs at functionally equivalent points, while AADs are believed to interact at an earlier point in the series (D. Tasset et al., Cell 62:1177–1187 (1990)).

Several putative coactivator TIFs for NR AF-2s have been characterized (see Chambon, P., FASEB J 10:940–954 (1996); Glass, C. K. et al., Current Opin. Cell Biol. 9:222–232 (1997); Horwitz, K. B. et al., Mol. Endocrinol. 10:1167–1177 (1996) for recent reviews). In particular, LeDouarin, B. et al., EMBO J. 15:6701–6715 (1996) have demonstrated that a 10-amino acid fragment of TIF1α is necessary and sufficient to mediate interaction with RXR in a ligand- and AF-2 integrity-dependent manner. Notably, within this TIF1α fragment, they identified a LxxLLL (SEQ ID NO: 13) motif, termed NR box, whose integrity is required for interaction with nuclear receptors, and pointed out that this motif is conserved in several other putative coactivators (LeDouarin, B. et al, EMBO J. 15:6701–6715 (1996)) Whereas TIF1α and several other putative coactivators do not, or only very poorly, stimulate transactivation by NRs in transiently transfected mammalian cels, the TIF2/SRC-1 family (Onate, S. A. et al., Science 270:1354–1357 (1995); Voegel, J. J. et al., EMBO J. 15:3667–3675 (1996)), the CBP/p300 family (Kamei, Y. et al., Cell 85:403414 (1996), Chakravarti D. et al, Nature 5:99–103 (1996); Hanstein, B., et al., Proc. Natl. Acad Sci USA 93:11540–11545 (1996); Smith, C. L. et al., Proc. Natl. Acad. Sci. USA 93:8884–8888 (1996); for recent reviews see Eckner, R., Biol. Chem. 377:685–688 (1996); Janknecht & Hunter, Current Biol. 6:951–954 (1996b); Shikama, N. et al., Trends in Cell Biol. 7:230–236 (1997)) and the androgen receptor coactivator ARA70 (Yeh & Chang, Proc. Natl. Acad. Sci. USA 93:5517–5521 (1996)) have been unequivocally shown to enhance AF-2 activity.

In addition to binding NRs, CBP/p300 can also interact directly with SRC-1 (Kamei, Y. et al., Cell 85:403–414 (1996); Yao, T. P. et al., Proc. Natl. Acad. Sci. USA 93:10626–10631 (1996)) and both factors have been shown to exert histone acetyltransferase activity (Bannister & Kouzarides, Nature 384:641–643 (1996); Ogryzko, V. V. et al., Cell 87:953–959 (1996)). Moreover, CBP/p300 can recruit p/CAF which is itself a nuclear histone acetyltransferase (Yang, X. J. et al., Nature 382:319–324 (1996)). However, apart from interacting with coactivators in a ligand-dependent manner, NRs have also been shown to interact, often in a ligand-independent fashion, directly or indirectly with components of the transcriptional machinery, suds as TFIIB, TBP, TAFs, or TFIIH (Baniahmad et al., (1993)); Jacq, X. et al., Cell 79:107–117 (1994); Schulman, IG. et al., Mol. Cell Biol. 16:3807–3813 (1996); May, M et al., EMBO J. 15:3093–3104 (1996); Mengus, G. et al., Genes & Dev. 11: 1381–1395 (1997)).

Hong, H. et al., Proc. Natl. Acad. Sci. USA 93:4948–4952 (1996) originally described a partial cDNA of the mouse homologue of TIF2, named GRIP1, and recently reported the isolation of a full length GRIP1 cDNA (Hong, H. et al., Mol. Cell. Biol. 17:2735–2744 (1997)). Using the yeast Saccharomyces cerevisiae as a model system, they have shown that transcriptional activation by TR, RAR and RXR, could also be stimulated by GRIP1 coexpression, which suggests that TIF2/GRIP1 could be a general coactivator for NRs (Hong, H. et al., Mol. Cell. Biol. 17:2735–2744 (1997)).

The overall picture emerging from multiple recent studies on the mechanisms by which nuclear receptors modulate target gene transcription involves three subsequent steps, (i) the ligand-induced transconformation of the NR LBD, which results in (ii) the dissociation of corepressors and formation of TIFs/coactivator complexes, which themselves (iii) through interaction with additional downstream factors (e.g., CBP, p300) modulate the acetylation status of core histones and, thus, chromatin condensation/decondensation. Histone acetylation on its own is, however, insufficient for transcription activation (Wong et al, (1997)), and a simultaneous or subsequent fourth event comprises the direct and/or indirect recruitment of elements of the transcription machinery (e.g., TFIB, TBP, TAFs, TFIIH; Jacq, X. et al., Cell 79:107–117 (1994); Schulman, IG. et al., Mol. Cell. Biol. 16:3807–3813 (1996); May, M. et al., EMBO J. 15:3093–3104 (1996); Mengus, G. et al., Genes & Dev. 11: 1381–1395 (1997)). Note that such interactions do not need to be ligand-dependent, if the primary function of the liganded LBD (AF-2) is to regulate DNA accessibility through chromatin remodeling. Indeed, several of the reported interactions between NRs and general transcription factors occur in a ligand-independent manner. Accordingly, there is a need in the art for the isolation and characterization of transcriptional intermediary factors.

SUMMARY OF THE INVENTION

By screening 340,000 clones of a human placenta cDNA expression library with an estradiol-bound estrogen receptor probe, the present inventors have identified a cDNA clone containing the gene encoding transcriptional intermediary factor 2 (TIF2). By the invention, TIF2 has been shown to exhibit all the properties expected for a TIF/mediator of AF-2: it interacts directly with the LBDs of several NRs in an agonist- and AF-2-integrity-dependent manner in vitro and in vivo, harbours an autonomous AF, relieves NR auto/squelching, and enhances the activity of NR AF-2s when overexpressed in mammalian cells.

Thus, in one aspect, the present invention provides isolated nucleic acid molecules comprising a polynucleotide encoding TIF2 whose amino acid sequence is shown in FIG. 1 (SEQ ID NO:2) or a fragment thereof. In another aspect, the invention provides isolated nucleic acid molecules encoding TIF2 having an amino acid sequence as encoded by the cDNA deposited as ATCC Deposit No. 97612.

The invention further provides an isolated nucleic acid molecule that hybridizes under stringent conditions to the above-described nucleic acid molecules. The present invention also relates to variants of the nucleic acid molecules of the present invention, which encode fragments, analogs or derivatives of the TIF2 protein, e.g., polypeptides having at least one biological activity that is substantially similar to at least on biological activity of the TIF2 protein.

The present invention is further directed to isolated nucleic acid molecules that encode a cytoplasmic TIF2 polypeptide. Methods for generating nucleic acid molecules that encode a cytoplasmic TIF2 polypeptide include mutating or deleting the NLSs-coding N-terminal region of the nucleotide sequence shown in FIG. 1 (SEQ ID NO:1). Preferably, nucleic acid molecules encoding a cytoplasmic TIF2 polypeptide will be fragments having a deletion in all or part of the N-terminal NLSs coding region. By the invention, the cytoplasmic TIF2 polypeptides described herein display at least one biological activity that is substantially similar to at least one biological activity of TIF2.

Further embodiments of the invention include isolated nucleic acid molecules comprising a polynucleotide having a nucleotide sequence at least 90% identical, and more preferably at least 95%, 96%, 97%, 98%, or 99% identical to the above described nucleic acid molecules.

The present invention also relates to vectors which contain the above-described isolated nucleic acid molecules, host cells transformed with the vectors and the production of TIF2 polypeptides by recombinant methods.

The present invention further provides isolated TIF2 polypeptides having the amino acid sequence shown in FIG. 1 (SEQ ID NO:2). In a further aspect, isolated TIF polypeptides are provided having an amino acid sequence as encoded by the cDNA deposited as ATCC Deposit No. 97612.

Screening methods are also provided for identifying agonists and antagonists of nuclear receptor AF-2 function, for identifying agonists and antagonists of TIF2 AD1 activity, and for identifying agonists and antagonists of TIF2 AD2 activity. Also provided are TIF2 antibodies.

BRIEF DESCRIPTION OF THE FIGURES

FIG. 1(a–n). The nucleotide (SEQ ID NO:1) and amino acid (SEQ ID NO:2) sequences of the transcriptional intermediary factor-2 (TIF2) protein. This protein has a deduced molecular weight of about 160 kDa. The amino acid sequence of the functional coactivator TIF2.1 protein fragment is shown from amino acid residue 624 to residue 1287.

Figures 2A, 2B:
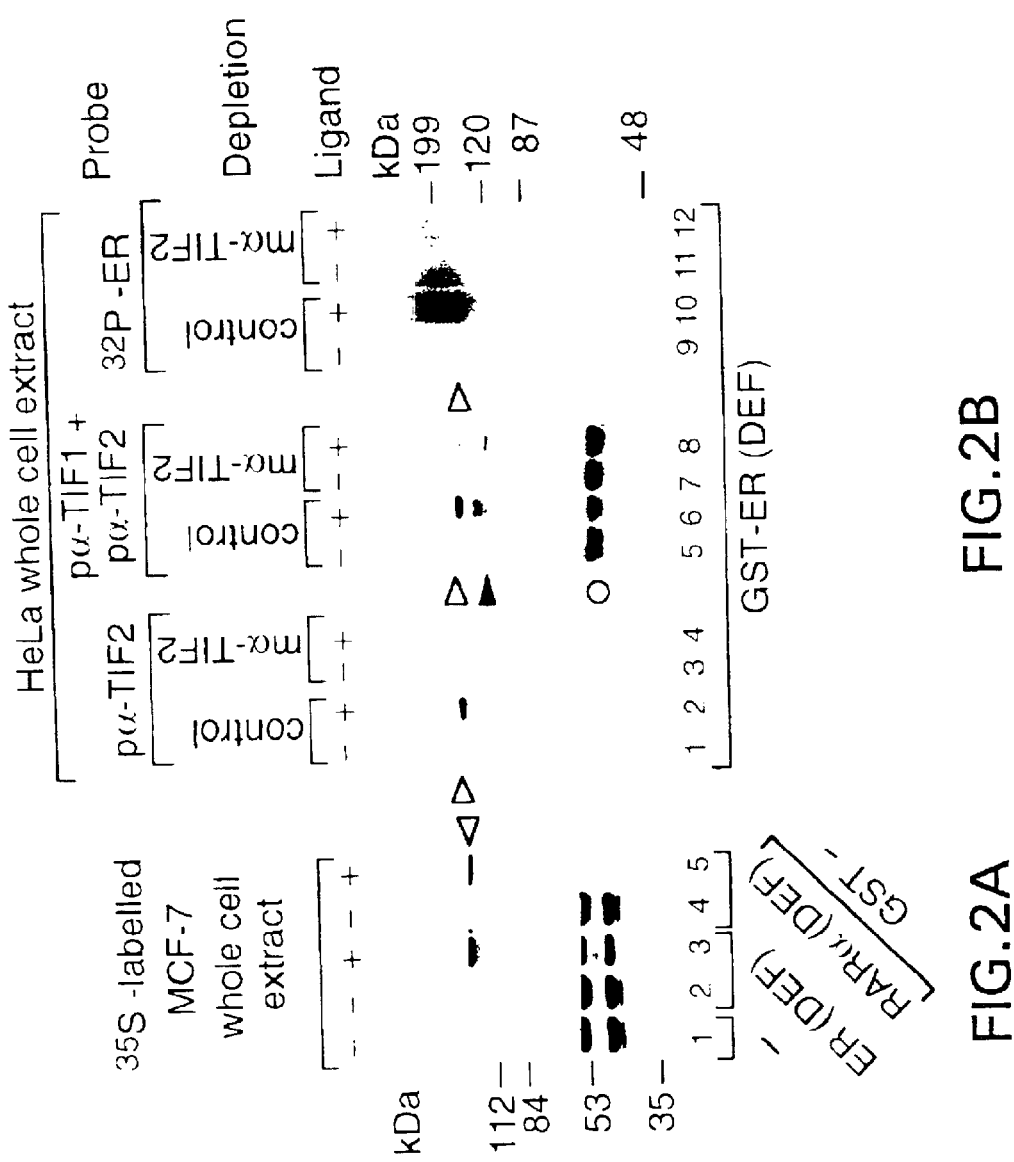
FIG. 2(a–c). TIF2 is the 160-kDa nuclear-receptor-interacting factor.

(a) GST pull-down experiments identify a 160-kDa protein interacting with liganded estrogen receptor (ER) and retinoic acid receptor (RAR)-α ligand binding domains (LBDs) (ER(DEF) and RARα(DEF), respectively). Note that less material was run in lane 5 than in lanes 1–4.

(b) Immunodepletion followed by Far-Western detection demonstrates identity of TIF2 with the biochemically identified 160-kDa protein. Open triangle, TIF2; arrowhead, TIF1; circle, antibody crossreaction to GST-ER(DEF). The pα-TIF2-immunodetected species smaller that TIF2 (lanes 2 and 6) most probably is a degradation product of TIF2, as it is removed by immunodepletion with mα-TIF2 (lanes 4 and 8).

(c) Northern blotting reveals a ≈9-kb TIF2 transcript in various human tissues.

Methods. (a) In vivo $^{35}$S-Met-labeled MCF7 whole cell extracts (Cavailles, V. et al., *Proc. Natl. Acad. Sci. USA* 91:10009–100013 (1994)) twice precleared with GST-loaded glutathione sepharose, were incubated (Le Douarin, B. et al., *EMBO J.* 14:2020–2033 (1995)) with GST, GST-HER (DEF) or GST-hRARα(DEF), in presence or absence of 104 M E2 or T-RA. Bound proteins were recovered with SDS sample buffer and revealed by fluorography (Amplify, Amersham) of SDS-polyacrylamide gels.

(b) HeLa whole cell extracts (2 ml in 500 mM NaCl, 250 mM Tris HCl pH 7.5, 20% glycerol, 5 mM DTT), were precleared with protein-G sepharose (400 µl) and treated with protein-G sepharose (3×400 µl) loaded with ma-TIF2 (raised against a synthetic peptide encompassing amino acids E624-Q643 coupled to ovalbumin) or non-specific mouse-IgG serum. After further clearing with protein-G sepharose (400 µl), the supernatant was incubated (Le Douarin, B. et al., *EMBO J.* 14:2020–2033 (1995)) with GST-hER(DEF) in presence or absence of E2 ($10^{-6}$M). Retained proteins were recovered with SDS sample buffer, separated by SDS-PAGE and electroblotted on nitrocellulose membranes. Far Western blotting was as described (Cavalle's, V. et al., *Proc. Natl. Acad. Sci. USA* 91:10009–100013 (1994)). For immunoblotting rabbit polyclonal antiserum (pα-TIF2), raised against purified (Chen, Z-P. et al., *J. Biol. Chem.* 269:25770–25776 (1994)) recombinant *E. coli*-expressed His-tagged TIF2.1, was used. pα-TIF2 and rabbit polyclonal pα-TIF1 were diluted 1:2000 for ECL-based Western blotting (Amersham). All constructs used in this study were verified by DNA sequencing.

(c) Human Northern blot (Clonetech, No 7760-1; Lot 5×332) was revealed with $^{32}$P-labeled TIF2.1. To confirm proportionate loading, the membrane was rehybridized with $^{32}$P-labeled β-actin cDNA (Clonetech).

Figure 3B:
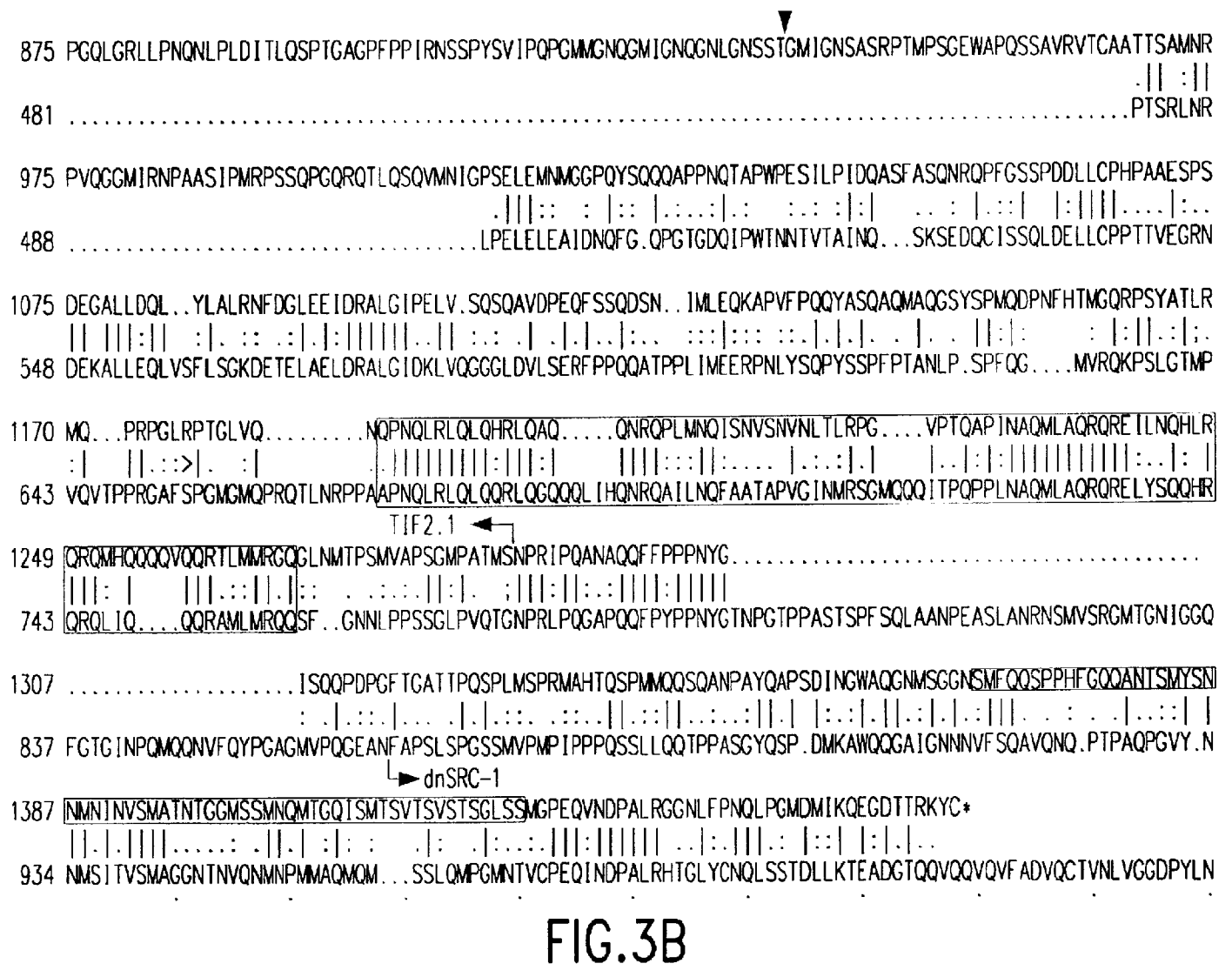
Figure 3C:
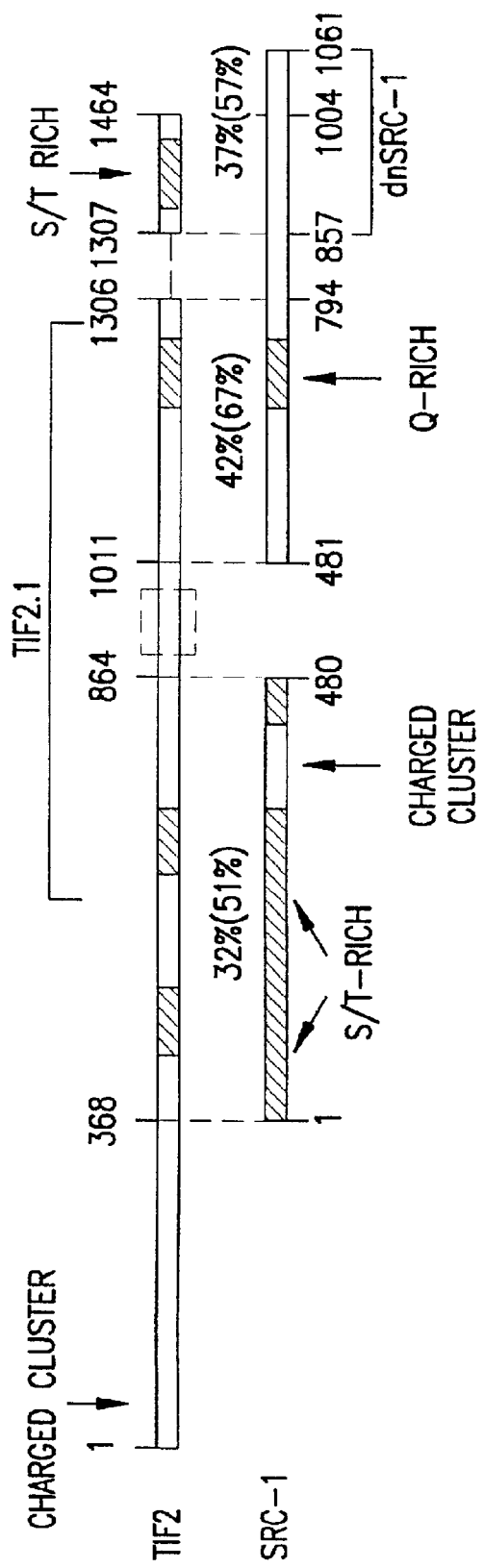

FIG. 3(a–c). Amino acid sequence of TIF2: homology with SRC-1 indicates the existence of a novel family of NR mediators.

(a-b) Alignment and amino acid sequences of TIF-2 (SEQ ID NO:2) and the steroid receptor coactivator SRC-1 (SEQ ID NO:3) (Onate, S. A. et al., *Science* 270:1354–1357 (1995)). Two charged clusters rich in acidic and basic amino acid residues, three serine/threonine (S/T)—rich regions and one glutamine-rich region are highlighted. The N-terminal charged cluster contains putative bipartite nuclear localization signals (NLSs) (overlined). The regions encoding TIF2.1 (amino acids 624 to 1287; functional coactivator fragment) and dnSRC-1 (amino acids 865 to 1061; dominant negative fragment) are indicated. An asterisk identifies the TIF2 stop codon. Note that TIF2.1 and dnSRC-1 do not overlap, indicating that dnSRC-1 may possibly contain a NR-interacting region distinct from that of TIF2.1.

(c) Schematic comparison of TIF2 and SRC-1. Percent identities (similarities in parentheses) of homologous regions are indicated. The N-terminal charged cluster harboring the putative NLS and the C-terminal S/T-rich region of TIF2 are not, or only weakly, conserved in SRC-1.

Methods. 340,000 clones of a human placenta cDNA λEXlox expression library were screened with a $^{32}$P-labeled GST-hER(DEF) probe in presence of 10M E2 using the Far-Western technique (Cavaillès, V. et al., *Proc. Natl. Acad. Sci. USA* 91:10009–100013 (1994)). The 1992-bp insert corresponding to the initial clone (TIF2.1) was used to rescreen the same library. Five highly overlapping cDNA inserts covered a region of 6 kb containing a 1,464-amino acid ORF. All inserts were sequenced on both strands. Transient expression of the assembled cDNA inserts encompassing the predicted ORF yielded a 160-kDa protein.

FIG. 4(a–n). In vivo and in vitro interactions of TIF2 with nuclear receptors.

(a) Overexpressed TIF2 protein is mostly localized in discrete nuclear bodies and excluded from nucleoli. A superposed image of Hoechst DNA staining and TIF2 immunostaining is shown.

(b–i) Cytoplasmic TIF2.1 interacts in an agonist-dependent manner with nuclear receptors in mammalian cells. Light staining indicates TIF2.1-NO colocalization.

(k–n) TLF2.1 directly interacts in vitro in an agonist-dependent manner with nuclear receptors, and point mutations within the AF-2 activation domain (AD) core abolish this interaction. WT, wild-type. Ligand concentrations for n: 9C-RA, T-RA and T3, $10^{-6}$ M; E2, $5\times10^{-9}$M; OHT, $5\times10^{-6}$M. The smaller immunodetected polypeptide is a degradation product of TIF2.1. Note that the anti-TIF2 serum weakly crossreacts with GST-hER(DEF).

Methods. (a–i) Cos-1 cells were transiently transfected with TIF2.1 (10 µg) either (a) alone or (b-i) in addition with the indicated NR expression vectors (10 µg, except RARα, 1 µg) in absence or presence of the cognate ligand($10^{-6}$M, except R5020, $10^{-8}$M). In d-f HE0 (Webster, N. J. et al., *Cell* 54:199–207 (1988)) was used. Immunocytofluorescence assays were as described (Kastner, P. et al, *EMBO J.* 11: 629–642 (1992)). Images were recorded by confocal laser microscopy.

(k-n) GST interaction assays with *E. coli*-expressed recombinant TIF2.1 (FIG. 2b) were performed as described (Le Douarin, B. et al., *EMBO J.* 14:2020–2033 (1995)). Bound proteins were revealed by Western blotting with pa-TIF2 antiserum (dilution 1:30,000), equal loading of affinity matrices was verified by SDS-PAGE and Coomassie staining. 'Input' lanes contain one third of TIF2.1 input.

FIG. 5(*a–e*). TIF2 contains an autonomous AF, "antisquelches", and stimulates NO-AF2 activity in an agonist-, promoter- and cell-dependent manner.

(a) Increasing amounts of GAL-TIF2.1 fusion protein (lanes 2–4) activates transcription of a cognate reporter in transfected cells. Fold-induction is given below the CAT assays.

(b) TIF2.1 partially reverses transcriptional autointerference of ER. Normalized CAT expression (mean±s.e. of 4 independent experiments) is shown. Open circles, +E2, +TIF2; squares, +E2, -TIF2; crosses, +OHT, +TIF2.

(c) TIF2 enhances transactivation mediated by some NR AF-2s, but not that mediated by other transcription factors. Mean TIF2 stimulations of 3 independent experiments are given (variation≦13%). Ligands: lanes 34, E2; lanes 7–8, DHT (dihydrotestosterone); lanes 11–12, R5020; lanes 15–16, T-RA.

(d) TIF2 enhances PR-mediated transcriptional activation from both a minimal (GRE-TATA) and a complex (MMTV) promoter; this stimulation is significantly greater in Cos-1 than in HeLa cells.

(e) TIF2 greatly enhances agonist-induced activation by ER in Cos-1 and more weakly in HeLa cells. Note that the weak, seemingly ligand-independent, TIF2-induction of ER (compare lanes 1 with 2 and 7 with 8) is due to residual estradiol in the culture medium. In d and e, TIF2 inductions of $\geq 3$ experiments are shown (variation≦10%).

Methods. With the exception of GAL-TIF2.1, TIF2.1 and TIF2, the construction of reporter plasmids and expression vectors has been described (Meyer, M-E. et al., *Cell* 57:433442 (1989); Bocquel, M-T. et al., *Nucl. acids Res.* 17:2581–2595 (1989); Tasset, D. et al., *Cell* 62:1177–1187 (1990); Gronemeyer, H. and Laudet, V., *Protein Profile* 2:1173–1308 (1995); Webster, N. J. et al., *Cell* 54:199–207 (1988); Strahle, U. et al., *EMBO J.* 7:3389–3395 (1988); Seipel, K. et al., *EMBO J.* 11:49614968 (1992); Nagpal, S. et al, *EMBO J.* 12:2349–2360 (1993); Chen, J-Y. et al., *EMBO J.* 14:1187–1197 (1995)). CAT assays were performed as described (Bocquel, M-T. et al., *Nucl. Acids Res.* 17:2581–2595 (1989)).

(a) HeLa cells were cotransfected with 1 μg (17m)$_5$-βG-CAT and 10 μg GAL(1–147) or 1,3 and 10 μg GAL(1–147)-TIF2.1, respectively.

(b) HeLa cells were cotransfected with 5 μg Vit-tk-CAT and the indicated amount of HEGO, with or without 5 μg TIF2.1 in the presence of 104 M E2 or OHT. CAT activity is given relative to that induced by 100 ng HEGO in presence of E2.

(c) HeLa cells were cotransfected with 1 μg 17m-tk-CAT and 1 μg of the indicated GAL-fusion vectors with or without the addition of 3 jug TIF2 expression vector in presence or absence of $10^{-6}$M ligand.

(d) HeLa (lanes 1–12) or Cos-1 lanes 13–18) cells were transfected with 5 fig GRE-TATA-CAT (lanes 1–6) or 1 μg MMTV-CAT (lanes 7–18) together with 1 μg hPR with or without 3 μg TIF 2 in presence or absence of 106 M of the indicated ligand.

(e) Cos-1 cells were cotransfected with 1 μg Vit-tk-CAT and 1 μg HEGO with or without 3 μg TIF2 in presence or absence of $10^{-6}$ M of the indicated ligands.

Figure 6A:
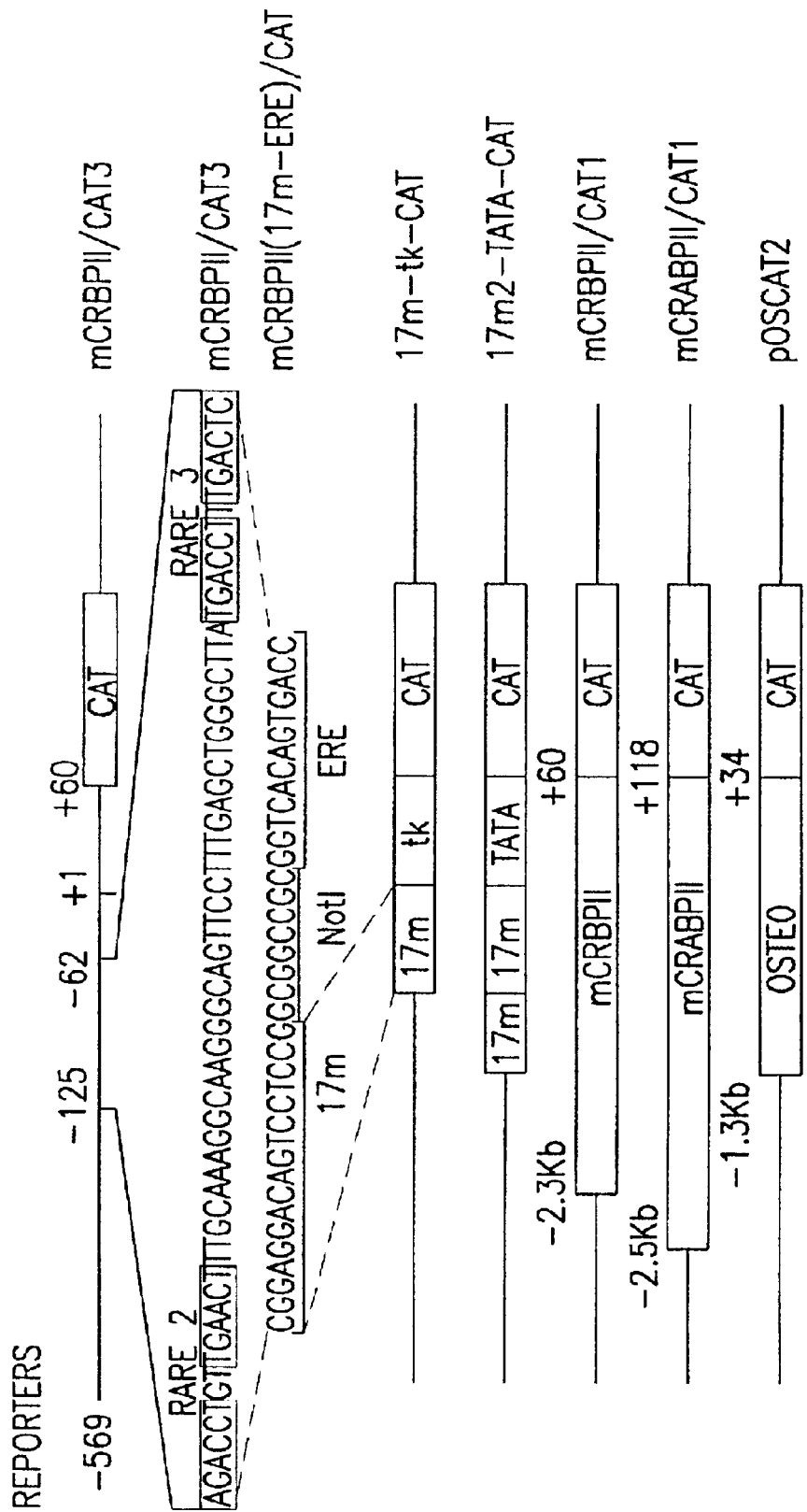
Figure 6C:
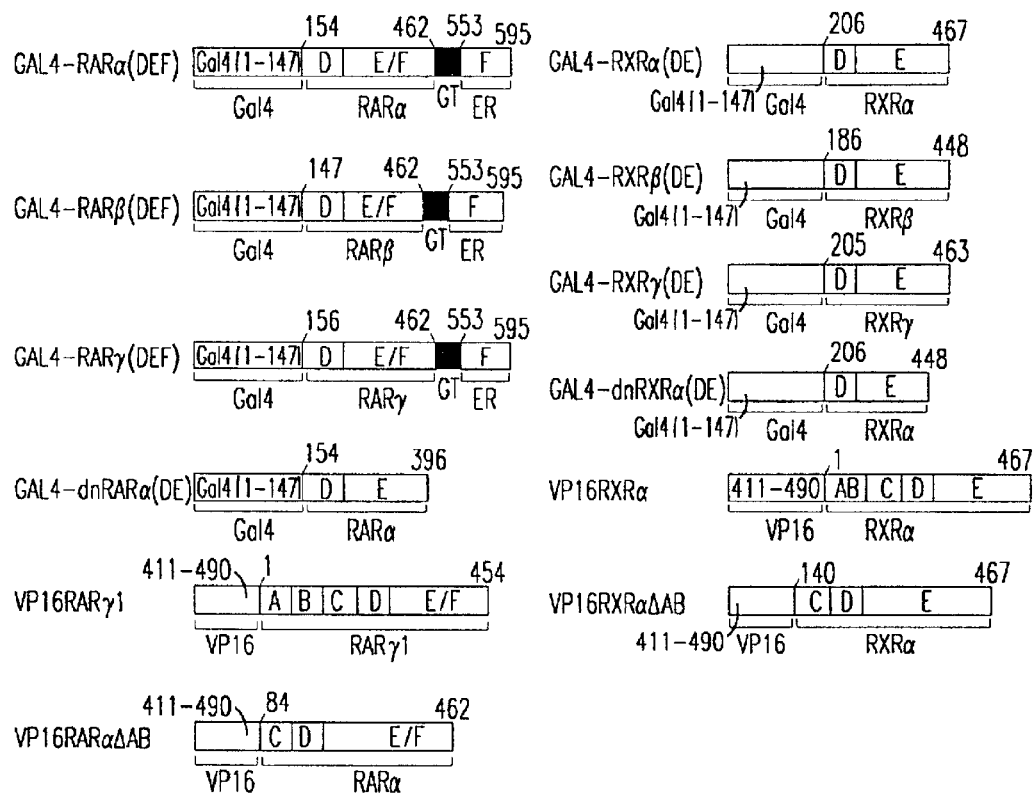

FIG. 6(*a–c*). Schematic representation of reporter genes (A) and receptor expression vectors (B–C) (see the Materials and Methods section of Nagpal et al., *EMBO J.* 12 (6):2349–2360 (1993) for a detailed description of construction). Sequences of mCRBPII (SEQ ID NO:11) and mCRBPII(17m-ERE)/CAT (SEQ ID NO:11) are indicated. Minus and plus numbers are with respect to the RNA start site (+1). In (B–C), the various regions (A–F) of wild-type RARs and RXRs, as well as their truncation mutants, substitution mutants and chimeric receptor constructs are schematically represented (not to scale) (see Zelent et al., *Nature* 339:714–717 (1989); Leid et al., *Trends Biochem. Sci.* 17:427–433 (1992); Leid et al., *Cell* 68:377–395 (1992); Nagpal et al., *Cell* 70.1007–1019 (1992); and Allenby et al., *Proc. Natl. Acad. Sci. USA* 90:30–34 (1993)). Numbers indicate the amino acid positions in the wild-type receptor. The positions of the amino acid substitutions are indicated with an arrow.

FIG. 7(*a*-e). Mapping of TIF2 domains.

(a) Schematic representation of functional domains identified in TIIF2. The various TIF2 constructs are denoted; expressed residues are given in parentheses. Bold lines indicate expressed sequences. Constructs that score positive or negative for NR interaction, transactivation or CBP binding are identified on the right by "+" and "−" signs respectively; nd, not determined.

(b) Mapping of the nuclear receptor-interacting domain of TIF2. Glutathione-S-transferase (GST) pull-down experiments were performed with $^{35}$S-labeled in-vitro-translated TIF2 polypeptides and bacterially produced GST, GST-hERα(DEF) and GST-hRARα(DEF) in the presence or absence of $10^{-6}$ M of the cognate ligand (E2, estradiol for ER; RA, all-trans-retinoic acid for RAR).

(c) Analysis of the transcriptional activity of GAL-TIF2 fusion proteins. Cos-1 and HeLa cells were transfected with 3 lag of plasmids expressing different regions of TIF2 fised to the DNA-binding domain of the yeast transcription factor GALA together with 1 μg of the (7m)$_5$-G-CAT reporterplasmid. CAT assays were performed as described (Bocquel, M. T. et al., *Nucl Acids Res.* 17:2581–2595 (1989)). Quantitative data on CAT reporter expression were obtained either by phosphoimager analysis (BAS2000, Fuji) of $^{14}$C-labeled CAT reaction products separated by thin-layer chromatography, or using the CAT ELISA Kit (Boehringer Mannheim). In all cases, CAT activities were normalized to the β-galactosidase concentrations resulting from cotransfection of 1 μg of pCMVPGal (gift from T. Lerouge) as internal control. Fold inductions above the GAL4 DBD value are indicated. The mean and standard deviation of at least three experiments are shown. A representative Western blot, illustrating the expression levels of the GAL4-TIF2 fusion proteins, expressed from 10 μg of the corresponding expression vectors, is shown on the left. The blot was revealed with mouse monoclonal antibodies 2GV3 and 3GV2 specific for GALA DBD and 2GV4B7 specific for VPI6 activation domain.

(d) Mapping of the CBP-interacting domain of TIF2. GST puld own experiments were performed with $^{35}$S-labeled in-vitro-translated TIF2 polypeptides and bacterially produced GST and GST-CBP (expressing CBP residues 1872 to 2165).

(e) Two hybrid analysis of the CBP-TIF2 interaction in mammalian cells in vivo. HeLa cells were transfected with 0.2 µg of the GAL4 or GALA-CBP (expressing CBP residues 1872 to 2165) expression vectors together with 0.2 µg of the VP16 or VPI6-TF2 expression vectors in the presence of 2 µg of (17m)$_5$-TATA-CAT reporter plasmid. Fold induction relative to the GAL-CBP activity is indicated. The mean of three experiments is shown; in each case, values varied by less than ±20%.

FIG. 8(a–f). Mapping of the TIF2 nuclear receptor interacting domain (NID).

(a) Alignment of the TIF2 NED (SEQ ID NO:2) with the corresponding regions of SRC-1 (SEQ ID NO:3) and P/CIP (SEQ ID NO:5) and description of NID mutations. The three conserved regions are displayed with the corresponding amino acid numbers of hTIF2 or full-length hSRC-1 (FSRC-1); the leucines pertaining to the three NR box motifs (I, II, III) are boxed. The various deletion and leucine-to-alanine point mutation constructs are denoted.

(b) Alignment of the TIF2 (SEQ ID NO:2) NR boxes with NR boxes identified in several cofactors: TIFIa (SEQ ID NO:6), RIP140 (SEQ ID NO:7), and TRIP3 (SEQ ID NO:8). The conserved leucines are boxed.

(c–d) Interaction of TIF2 NID mutants with NRs in vitro. GST affinity chromatography experiments were carried out with $^{35}$S-labelled in-vitro-translated GALA DBD fusions of TIF2 deletion mutants (c) or TIF2.1 point mutants (d) and bacterially expressed GST and GST fusions of the ER(DEF) and RAR(DEF) in the absence or presence of $10^{-6}$ M estradiol or all-trans-retinoic acid, respectively. For quantification of point mutant interactions, see below.

(e-f) Effect of TIF2 NID point mutations on stimulation of NR AF-2 activity. Cos-1 cells were cotransfected with 1 µg of the (17m)$_5$-TATA-CAT reporter, 0.2 µg of GAL-hERα (EF) or GAL-mRXRα(DE), and 2.5 µg of the TIF2.1 wildtype or mutated fragments, as indicated. The reporter gene activation relative to the TIF2.1 wildtype activity and in presence of $10^{-6}$ M estradiol (E2) or all-trans-retinoic acid (RA), respectively, is indicated for each mutant (black bars); for comparison, in vitro binding of the respective mutants relative to TIF2.1 wildtype binding in presence of ligand is indicated by the white bars. Each bar represents the mean value obtained from at least three (interaction) or at least four (transactivation) experiments, respectively; standard deviations are indicated. Note that the absolute values for TIF2.1 wildtype activity varied by ±16% when cotransfected with GAL-hERα(EF) and by ±34% when cotransfected with GAL-mRXRα(DE). In the in-vitro-interaction assays, the affinity of the TIF2.1 wildtype standard varied by less than ±25%. Expression levels of TIF2 mutants in the cells were verified by Western blot (not shown) with mouse monoclonal antibody 3Ti3F1, which is directed against an epitope outside the mutated area.

FIG. 9(a–c). Mapping of the TEF2 activation function-1 (AF-1) and interaction of the AF-1 domain with CBP.

(a) Alignment of the TIF2 AF-1 with the corresponding region of SRC-1 (SEQ ID NO:3) and P/CIP (SEQ ID NO:9). Description of TIF2 AF-1 deletion mutants and their properties. The regions of TIF2 and hSRC-1 predicted to fold into α-helices are boxed (PHD program). GAL-TIF2 constructs that score positive or negative for transactivation of a GAL4 reporter are identified on the right by "+" and "−" signs, respectively; nd, not determined.

(b) Transcriptional activation of TIF2 AF-1 mutants. Cos-1 and HeLa cells were cotransfected with 3 µg of plasmids expressing different mutants of the TIF2 AF-1 fused to the DNA-binding domain of the yeast transcription factor GAL4 together with 1 µg of the (17m)$_5$-G-CAT reporter plasmid. Fold inductions above the activation seen with the GAL4 DBD alone are indicated. The values represent the mean of at least three experiments. Note that all GALA-TIF2 fusion proteins were expressed to similar levels, as revealed by Western blot with antibodies directed against GAL4 DBD (data not shown).

(c) Interaction of TIF2 AF-1 mutants with CBP in vitro. GST pull-down experiments were performed with $^{35}$S-labeled in-vitro-translated GAL-TIF2 fusion proteins and bacterially produced GST and GST-CBP. Note, that the GAL4 DBD on its own does not interact with the GST-CBP affinity matrix.

Figure 10A:
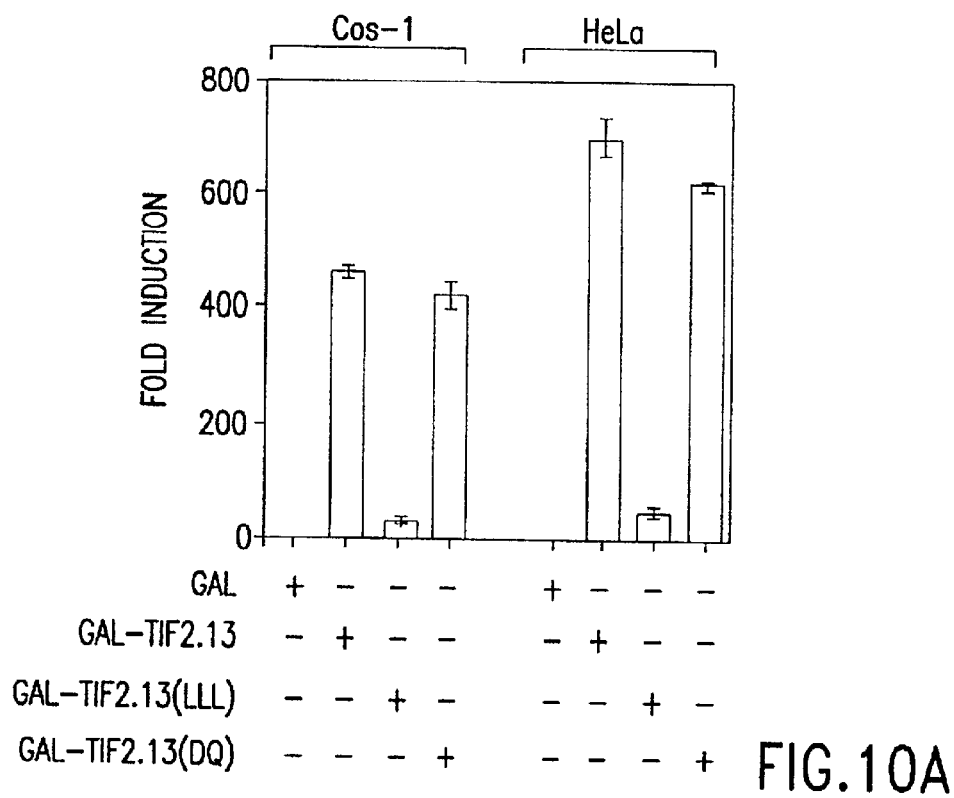

FIG. 10(a–c). Identification of TIF2 AF-1 mutants which are impaired in both transcriptional activation and interaction with CBP.

(a) Transcriptional activation by TIF2.13 and TIF2.13 mutants. Cos-1 and HeLa cells were cotransfected with 3 µg of plasmids expressing the TIF2.13 region and the indicated TIF2.13 mutants fused to the DNA-binding domain of the yeast transcription factor GALA together with 1 µg of the (17m)$_5$-G-CAT reporter plasmid. Fold inductions above the GAL4 DBD 1-fold value are indicated. The mean and standard deviation obtained from at least four experiments are shown. The expression levels of the GAL4-TIF2.13 fusion proteins were confirmed by western blotting (data not shown).

(b) Interaction of TIF2.13 wildtype and TIF2.13 mutants with CBP in mammalian cells revealed by two hybrid analysis. HeLa cells were transfected with 0.2 µg of GAL4 or GAL-CBP expression vectors together with 0.2 µg of VP16 or VP16-TIF2.13 expression vectors in the presence of 1 µg of (17m)$_5$-TATA-CAT reporter plasmid. Data are represented as fold induction of the activity seen with GAL-CBP alone. The mean and standard, deviation obtained from ten experiments are shown. The expression levels were confirmed by Western blotting with antibodies directed against GAL4 DBD and VP16 AAD (data not shown).

(c) Interaction of TIF2.13 wildtype and TIF2.13 mutants with CBP in vitro. GST pull-down experiments were performed with $^{35}$S-labeled in-vitro-translated VP16-TIF2.13 polypeptides and bacterially produced GST and GST-CBP. Note that the VP16 activation domain on its own does not interact with GST-CBP.

Figure 11:
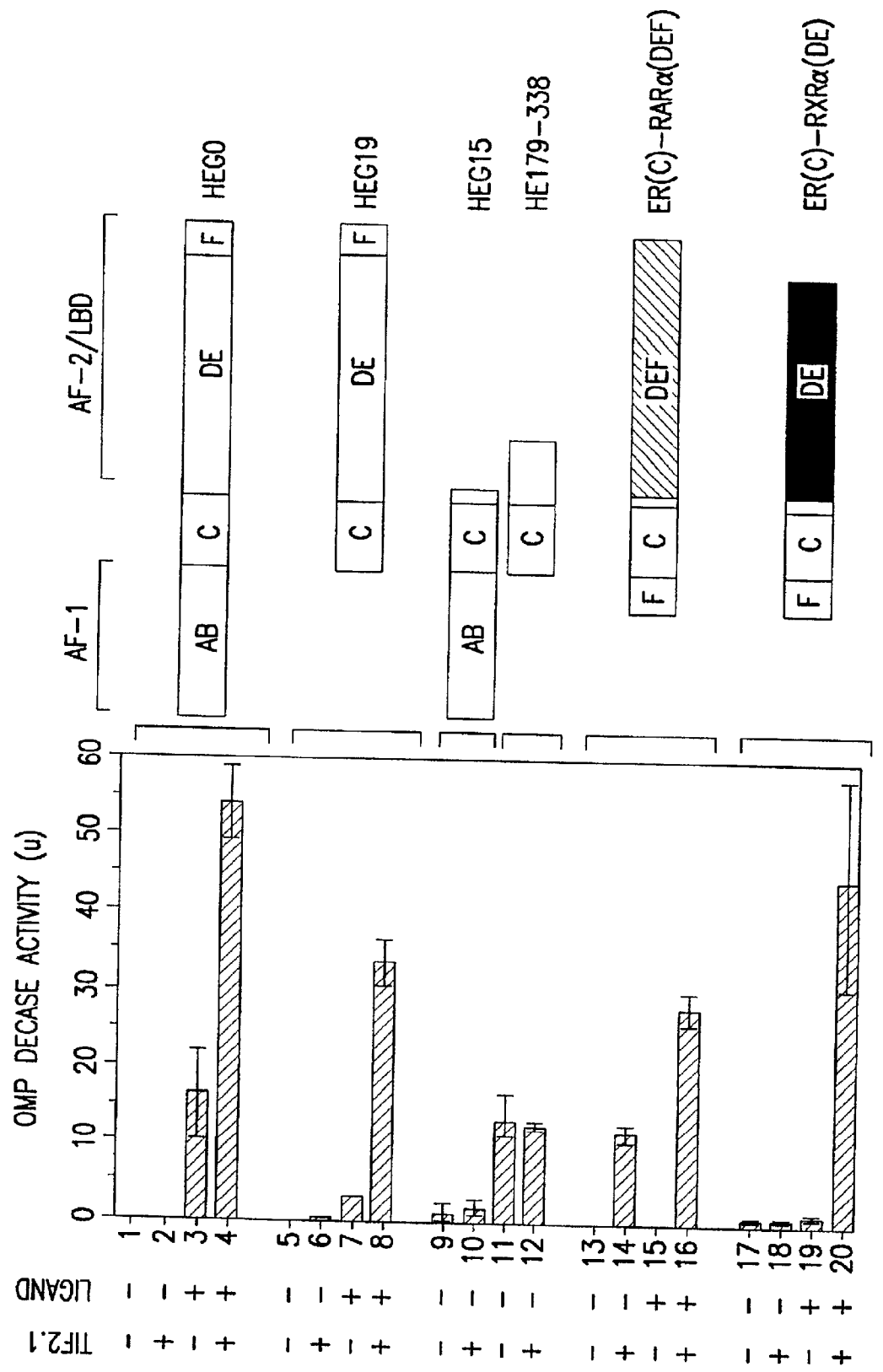

FIG. 11. The TIF2.1 coactivator fragment efficiently stimulates the ligand-dependent AF-2 of ER, RAR and RXR in yeast. No stimulatory effect of TIF2.1 on the isolated AF-1 of ER (HE15) is observable. Plasmids expressing different regions of hERα (white), hRARα (grey) and mRXRα (black) fused to the ER DBD (hERα(C)) were introduced into the yeast reporter strain PL3 (α) together with TIF2.1 as indicated. White boxes represent sequences of transformants that were grown in the presence or absence of $10^{-6}$ M of the cognate ligand (estradiol for ER, all-trans-retinoic acid for RAR, 9-cis-retinoic acid for RXR). OMP decase activities determined on each cell-free extract are expressed in nmoyrnin/mg protein; the mean and standard deviation of at least four experiments are shown.

FIG. 12(a–d). The isolated nuclear receptor-interacting domain (ND) of TIF2 acts dominant-negatively on the transcriptional activation by the ER, RXR and RAR LBDs. The mean value of induction obtained from the quantitation of at least three experiments (relative to the respective receptor LBD activity in absence of recombinant TIF2) is indicated below each panel. Expression levels of TIF2, TIF2.1 and TIF2.5 were routinely verified by Western blot with mouse monoclonal antibody 3Ti3C11 directed against a region of TIF2.5 (not shown).

(a) Overexpression of the TIF2.5 fragment containing the isolated NID reverses the stimulatory effect of the potent coactivator fragment TIF2.1. Cos-1 cells were cotransfected with 1 μg of the (17m)$_5$-TATA-CAT reporter and 0.2 μg GAL-ERα(EF) expression vector in the presence or absence of 10$^{-4}$ M estradiol. Where indicated, 0.1 μg of TIF2.1 and 2.5 μg of TIF2.5 expression vectors were cotransfected in addition.

(b–d) Full length TIF2 and the coactivator fragment TIF2.1 enhance, whereas the nuclear receptor interacting domain TJF2.5 blocks the activity of the ER, RXR and RAR LBDs. Cos-1 and HeLa cells were cotransfected with 1 μg of the (17m)$_5$-TATA-CAT reporter and 0.2 μg of the expression vector encoding the respective GAL DBD-fusion of hERα(EF), mRXRα(DE) or mRARα(DEF). In the presence or absence of 10$^{-6}$ M ligand (E2, estradiol; 9C-RA, 9-cis-retinoic acid; T-RA, all-trans-retinoic acid), together with 0.25 μg or 2.5 μg of TIF2, TIF2.1 and TIF2.5 expression vectors.

DETAILED DESCRIPTION OF THE PREFERRED EMBODIMENTS

The present invention provides isolated nucleic acid molecules comprising a polynucleotide encoding transcriptional intermediary factor-2 (TIF2) whose amino acid sequence is shown in FIG. 1 (SEQ ID NO:2). The TIF2 protein of the present invention shares sequence homology with the human steroid receptor coactivator SRC-1 (SEQ ID NO:3) (FIG. 3). The nucleotide sequence shown in FIG. 1 (SEQ ID NO:1) was obtained by sequencing a cDNA clone which was deposited on Jun. 14, 1996 at the ATCC and given accession number 97612.

Nucleic Acid Molecules

Figure 2C:
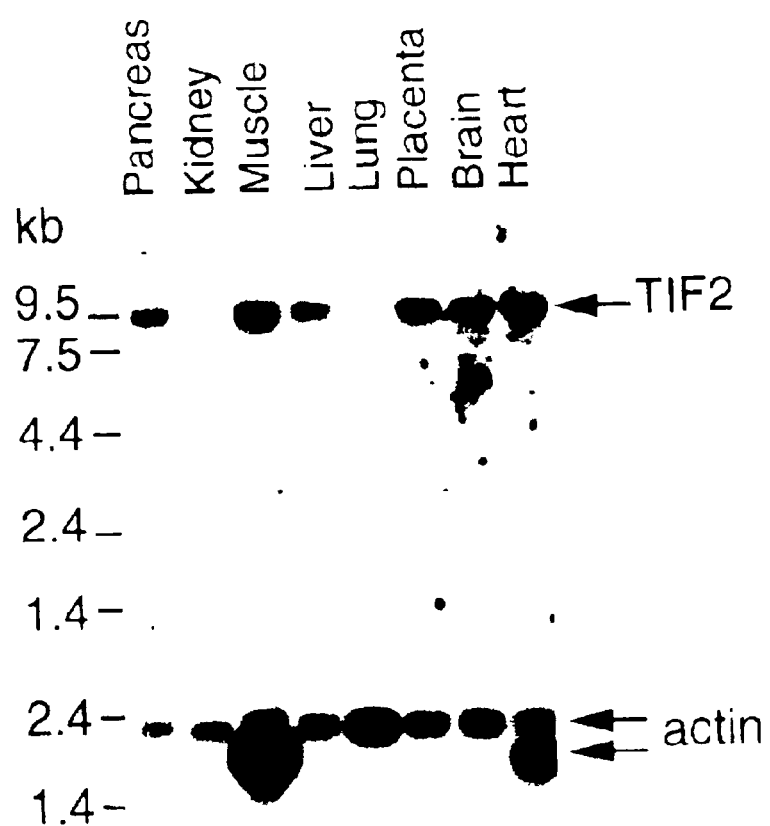

In one embodiment of the present invention, isolated nucleic acid molecules are provided which encode the TIF2 protein. Sequence similarities between TIF2 and SRC-1 (Onate et al., *Science* 270:1354 (1995)) indicate the existence of a novel gene family of NR transcriptional mediators. Using information provided herein, such as the nucleotide sequence in FIG. 1 (SEQ ID NO:1) or the above-described deposited clone, a nucleic acid molecule of the present invention encoding a TIF2 polypeptide may be obtained using standard cloning and screening procedures. Illustrative of the invention, the nucleic acid molecule described in FIG. 1 (SEQ ID NO:1) was discovered in a cDNA expression library from human placenta tissue. The TIF2 cDNA of the present invention encodes a protein of about 159 kDa (1,464 amino acids), which includes N-terminal nuclear localization signals (NLSs), one Gln- and three Ser/Thr-rich regions, and two charged clusters FIG. 3). TIF2 is widely expressed, since the corresponding transcript was found in several human tissues, including pancreas, kidney, muscle, liver, lung, placenta, brain and heart (FIG. 2c). Isolated nucleic acids of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for purposes of the present invention. Additional illustrative examples of isolated DNA molecules include recombinant DNA molecules maintained in heterologous host cells and purified (partially or substantially) DNA molecules in solution. Isolated RNA molecules include ini vitro RNA transcripts of the DNA molecules of the present invention as well as partially or substantially purified mRNA molecules. Isolated nucleic acid molecules according to the present invention further include such molecules produced synthetically.

Isolated nucleic acid molecules of the present invention include DNA molecules comprising an open reading frame (ORF) with an initiation codon at position 163–165 of the nucleotide sequence shown in FIG. 1 (SEQ ID NO:1); and DNA molecules which comprise a sequence substantially different than that described above but which, due to the degeneracy of the genetic code, still encode the TIF2 protein. Of course, the genetic code is well known in the art. Thus, it would be routine for one skilled in the art to generate the degenerate variants described above.

In another aspect, the invention provides isolated nucleic acid molecules encoding the TIF2 polypeptide having an amino acid sequence as encoded by the cDNA clone deposited as ATCC Deposit No. 97612 on Jun. 14, 1996 (American Type Culture Collection, (ATCC) 10801 University Boulevard, Manassas, Va. 20110-2209). The invention further provides an isolated nucleic acid molecule having the nucleotide sequence shown in FIG. 1 (SEQ ID NO:1) or the nucleotide sequence of the TIF2 cDNA contained in the above-described clone, or a nucleic acid molecule having a sequence complementary to one of the above sequences. Such isolated nucleic acid molecules, preferably DNA molecules, are useful as probes for gene mapping by in situ hybridization with chromosomes and for detecting expression of the TIF2 gene in human tissue, for instance, by Northern blot analysis.

In another aspect, the invention provides an isolated nucleic acid molecule that hybridizes under stringent conditions to the above-described nucleic acid molecules. As used herein "stringent conditions" is intended to mean, as a non-limiting example, overnight incubation at 42° C. in a solution comprising 50% formamide, 5×SSC (150 mM NaCl, 15 mM trisodium citrate), 50 mM sodium phosphate (pH7.6), 5× Denhardt's solution, 10% dextran sulfate, and 20 μg/ml denatured, sheared salmon sperm DNA, followed by washing the filters in 0.1×SSC at about 65° C. Preferably, such "an isolated nucleic acid molecule that hybridizes under stringent conditions" will be at least 15 bp, preferably at least 20 bp, more preferably at least 30 bp, and most preferably, at least 50 bp in length.

As used herein, "fragments" of an isolated DNA molecule having the nucleotide sequence of the deposited cDNA or the nucleotide sequence as shown in FIG. 1 (SEQ ID NO:1) is intended to mean DNA fragments at least 15 bp, more preferably at least 20 bp, and most more preferably at least 30 bp in length which are useful as diagnostic probes and primers as discussed above and in more detail below. Larger DNA fragments, up to, for example, 500 bp in length, are also useful as probes according to the present invention. A fragment of at least 20 bp in length, for example, is intended to mean fragments which include 20 or more contiguous bases from the nucleotide sequence of the deposited cDNA or the nucleotide sequence as shown in FIG. 1 (SEQ ID NO:1). As indicated, such fragments are useful diagnostically either as a probe according to conventional DNA hybridization techniques or as primers for amplification of a target sequence by the polymerase chain reaction (PCR).

Since the gene has been deposited and the nucleotide sequence shown in FIG. 1 (SEQ ID NO:1) is provided, generating such DNA fragments would be routine to the skilled worker in the relevant art. Restriction endonuclease cleavage or shearing by sonication, for example, may easily be used to generate fragments of various sizes. Alternatively, the DNA fragments of the present invention can be generated synthetically according to the methods and techniques known and available to those skilled in the art. Ten expressed sequence tags with homology to part of the TIF-2 nucleoide sequence were identified by the inventors in GenBank: GenBank Accession numbers T77249, R77864, T77464, R77770, R08880, T85560, R25318, T85561, R08986 and R26517.

The present invention further relates to variants of the nucleic acid molecules of the present invention, which encode for fragments, analogs or derivatives of the TIF2 protein, e.g., polypeptides having biological activity substantially similar to the TIF2 protein. Variants may occur naturally, such as isoforms and allelic variants. Non-naturally occurring variants may be produced using any of the mutagenesis techniques known and available to those skilled in the art.

Such variants include those produced by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions. Especially preferred among these are silent substitutions, additions and deletions, which do not alter the properties and activities of the TIF2 protein or fragment thereof. Also especially preferred in this regard are conservative substitutions.

The present invention is further directed to isolated nucleic acid molecules that encode a cytoplasmic TIF2 polypeptide. Full-length TIF2 is a nuclear protein due to the presence of N-terminal nuclear localization signals (NLSs) (FIG. 3). By a "cytoplasmic TIF2 polypeptide", is intended a TIF2 polypeptide that is essentially found in the cytoplasm after being recombinantly expressed in mammalian cells. Methods for generating nucleic acid molecules that encode a cytoplasmic TIF2 polypeptide include mutating or deleting the NLSs-coding N-terminal region of the nucleotide sequence shown in FIG. 1 (SEQ ID NO:1). Examples of NLS sequences include amino acids 13–20 and 31–39 and nucleotides 199–222 and 253–279 of FIG. 1 (See also, FIG. 3). Suitable mutations to the NLSs-coding N-terminal region include substitutions, deletions and insertions which result in a nucleic acid molecule that encodes a TIF2 polypeptide lacking the nuclear localization function. Methods for generating such mutations will be readily apparent to the skilled artisan and are described, for instance, in *Molecular Cloning, A Laboratory Manual*, 2nd edition, edited by Sambrook, J., Fritsch, E. F. and Maniatis, T., (1989), Cold Spring Harbor Laboratory Press.

Preferably, nucleic acid molecules encoding a cytoplasmic TIF2 polypeptide will be fragments having a deletion in all or part of the N-terminal NLSs coding region. Methods for generating such fragments are described below. According to the present invention, such nucleic acid fragments further include N-terminal deletions extending beyond the NLSs coding region and may also include C-terminal deletions. For example, the present inventors have generated a nucleic acid molecule encoding the cytoplasmic TIF2.1 polypeptide (amino acids 624 to 1287 in FIGS. 1 and 3 (SEQ ID NO: 2)), which, like the nuclear full-length TIF2, interacts in an agonist-dependent manner with the nuclear receptors and enhances nuclear receptor-mediated transcriptional activation. The present inventors have also generated a nucleic acid molecule encoding the cytoplasmic TIF2.5 polypeptide (amino acids 624–869 in FIGS. 1 and 3 (SEQ ID NO:2)), which interacts with the NID domain of nuclear receptors, but does not enhance transcription. Also generated were nucleic acids encoding the cytoplasmic TIF2.8 and TIF 2.12 polypeptides (amino acids 1010–1179 and amino acids 940–1131, respectively, in FIGS. 1 and 3 (SEQ ID NO:2), which enhance transcription, but do not bind to nuclear receptors. Thus, by the invention, nucleic acid molecules are provided encoding cytoplasmic TIF2 polypeptides that interact in an agonist-dependent manner with nuclear receptors and enhance nuclear receptor-mediated transcriptional activation. Also provided are cytoplasmic TIF2 polypeptides that bind to nuclear receptors, but do not enhance transcription as are provided cytoplasmic TIF2 polypeptides that enhance transcription, but do not bind to nuclear receptors. As the skilled artisan will recognize, the length of such nucleic acid molecules can vary.

Further embodiments of the invention include isolated nucleic acid molecules comprising a polynucleotide having a nucleotide sequence at least 90% identical, and more preferably at least 95%, 96%, 97%, 98%, or 99% identical to: (a) the nucleotide sequence of the cDNA deposited as ATCC 97612; (b) the nucleotide sequence shown in FIG. 1 (SEQ ID NO:1); (c) the nucleotide sequence of the cDNA deposited as ATCC 97612 which encodes the full-length TIF2 protein; (d) the nucleotide sequence shown in FIG. 1 (SEQ ID NO:1), which encodes the full-length TIF2 protein; (e) the nucleotide sequence of the cDNA deposited as ATCC 97612, which encodes the functional coactivator TIF2.1 protein; (f) the nucleotide sequence shown in FIG. 1 (SEQ ID NO:1), which encodes the functional coactivator TIF2.1 protein; (g) the nucleotide sequence shown in FIG. 1 (SEQ ID NO:1) which encodes the TIF2.0 polypeptide; (h) the nucleotide sequence shown in FIG. 1 (SEQ ID NO:1) which encodes the TIF2.2 polypeptide; (i) the nucleotide sequence shown in FIG. 1 (SEQ ID NO:1) which encodes the TIF2.3 polypeptide; (O) the nucleotide sequence shown in FIG. 1 (SEQ ID NO:1) which encodes the TIF2.4 polypeptide; (k) the nucleotide sequence shown in FIG. 1 (SEQ ID NO:1) which encodes the TIF2.5 polypeptide; (1) the nucleotide sequence shown in FIG. 1 (SEQ ID NO:1) which encodes the TIF2.6 polypeptide; (m) the nucleotide sequence shown in FIG. 1 (SEQ H)NO:1) which encodes the TIF2.7 polypeptide; (n) the nucleotide sequence shown in FIG. 1 (SEQ ID NO:1) which encodes the TIF2.8 polypeptide; (o) the nucleotide sequence shown in FIG. 1 (SEQ ID NO:1) which encodes the TIF2.9 polypeptide; (p) the nucleotide sequence shown in FIG. 1 (SEQ ID NO:1) which encodes the TIF2.10 polypeptide; (q) the nucleotide sequence shown in FIG. 1 (SEQ ID NO:1) which encodes the TIF2.12 polypeptide; and (r) a nucleotide sequence complementary to any of the nucleotide sequences in (a–q).

Whether any two nucleic acid molecules have nucleotide sequences that are at least 90%, 95%, 96%, 97%, 98%, or 99% "identical" can be determined conventionally using known computer algorithms such as the "fastA" program using, for example, the default parameters (Pearson and Lipman, *Proc. Natl. Acad. Sci. USA* 85:2444 (1988)). The present application is directed to such nucleic acid molecules having a nucleotide sequence at least 90%, 95%, 96%, 97%, 98%, 99%, identical to the nucleotide sequence of the above-recited nucleic acid molecules irrespective of whether they encode a polypeptide having TIF2 activity. This is because, even where a particular nucleic acid molecule does not encode a polypeptide having TIF2 activity, one of skill in the art would still know how to use the nucleic acid molecule as a probe. Uses of the nucleic acid molecules of the present invention that do not encode a polypeptide having TIF2 activity include, inter alia, (1) isolating the TIF2 gene or allelic variants thereof in a cDNA library; (2) in situ hybridization (FISH) to metaphase chromosomal spreads to provide precise chromosomal location of the TIF2 gene as described in Verma et al., *Human Chromosomes: a Manual of Basic Techniques*, Pergamon Press, New York (1988); and Northern Blot analysis for detecting TIF2 mRNA expression in specific tissues, such as placenta tissue.

Preferred, however, are nucleic acid molecules having a nucleotide sequence at least 90%, and preferably at least 95%, 96%, 97%, 98%, or 99% identical to the nucleotide sequence of the above-described nucleic acid molecules which do, in fact, encode a polypeptide having at least one TIF2 protein activity. As used herein, "a polypeptide having a TIF2 protein activity" is intended to mean polypeptides exhibiting similar, but not necessarily identical, activity as at least one biological activity of the TIF2 protein as measured in a particular biological assay. For example, the TIF2 protein of the present invention interacts directly in an agonist-dependent manner with the ligand binding domains of several nuclear receptors. Moreover, when recombinantly expressed in mammalian cells, the TIF2 protein of the present invention enhances transcription via CBP-dependent and CBP-independent routes.

Thus, "a polypeptide having a TIF2 protein activity" includes polypeptides having one or more of the following activities: interaction with the LBD of one or more NRs in an agonist-dependent manner; enhancement of CBP-dependent transcriptional activation; or enhancement of CBP-independent transcriptional activation.

Screening assays for determining whether a candidate polypeptide has TIF2 protein activity are described in detail in Examples 1, 3, 4, and 6 below. For example, by performing such assays, the present inventors have discovered that the functional coactivator fragment TIF2.1 (amino acids 624 to 1287 in FIGS. 1 and 3 (SEQ ID NO: 2)) is "a polypeptide having a TIF2 protein activity." The present inventors have also discovered that the fragment TIF2.5 (amino acids 624–869) binds to the LBD of NRs without activating transcription, and is "a polypeptide having a TIF2 protein activity." Also discovered was the fragment TIF2.2 (amino acids 1288–1464 as shown in FIG. 1 (SEQ ID NO:2)), which enhances CBP-independent transcription. Thus, TIF2.2 is "a polypeptide having a TIF2 protein activity." Another fragment discovered by the inventors, TIF 2.8 (amino acids 1010–1179 as shown in FIG. 1 (SEQ ID NO:2)) is a "polypeptide having a TIF2 protein activity" as it activates CBP-dependent transcription.

Due to the degeneracy of the genetic code, one of ordinary skill in the art will immediately recognize that a large number of the nucleic acid molecules having a nucleotide sequence at least 90%, preferably at least 95%, 96%, 97%, 98%, 99% identical to the nucleotide sequence of the above-described nucleic acid molecules will encode "a polypeptide having a TIF2 protein activity." In fact, since degenerate variants all encode the same polypeptide, this will be clear to the skilled artisan even without performing the above described screening assays. It will be further recognized by those skilled in the art that, for such nucleic acid molecules that are not degenerate variants, a reasonable number will also encode a polypeptide having a TIF2 protein activity. This is because the skilled artisan is fully aware of possible amino acid substitutions that are either less likely or not likely to significantly affect protein function (e.g., replacing one aliphatic amino acid with a second aliphatic amino acid).

Guidance concerning how to make phenotypically silent amino acid substitutions is provided, for example, in J. U. Bowie et al., "Deciphering the Message in Protein Sequences: Tolerance to Amino Acid Substitutions," Science 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce anmno acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie et al., supra, and the references cited therein.

Vectors and Host Cells

The present invention also relates to Vectors which include the isolated DNA molecules of the present invention, host cells which are genetically engineered with the recombinant vectors, and the production of TIF2 polypeptides or fragments thereof, such as TIF2.1, by recombinant techniques. Recombinant constructs may be introduced into host cells using well known techniques such infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate trans-acting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate proriioter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating AUG at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in E. coli and other bacteria. Representative examples of appropriate hosts include, but are not limited to, bacterial cells, such as *E. coli, Streptomyces* and *Salmonella typhimurium* cells, fungal cells, such as yeast cells; insect cells such as *Drosophila* S2 and *Spodoptera* Sf9 cells; animal cells such as CHO, Cos and Bowes melanoma cells; and plant cells. Appropriate culture mediums and conditions for the above-described host cells are known in the art.

Illustrative examples of vectors preferred for use in bacteria include, but are not limited to, pA2, pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Preferred eukaryotic vectors include, but are not limited to, pWLNEO, pSV2CAT, pOG44, pXT1 and pSG available (from Stratagene; and pSVK3, pBPV, pMSG and pSVL available from Pharmacia. Other suitable vectors will be readily apparent to the skilled artisan.

Among known bacterial promoters suitable for use in the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods in Molecular Biology* (1986).

Transcription of the DNA encoding the polypeptides of the present invention by higher eukaryotes may be increased by inserting an enhancer sequence into the vector. Enhancers are cis-acting elements of DNA, generally about 10 to 300 bp in size, that act to increase transcriptional activity of a promoter in a given host cell-type. Illustrative examples of enhancers include, but are not limited to, the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals, but also additional heterologous functional regions. Thus, for instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification.

The TIF2 protein or fraction thereof can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention include, but are not limited to, naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be post translationally modified (e.g., glycosylated, phosphorylated, farnesylated, etc.). In addition, polypeptides of the invention may also include an initial modified methionine residue, in some cases as a result of host-mediated processes.

TIF2 Polypeptides and Fragments

The invention further provides an isolated TIF2 polypeptide having the amino acid sequence encoded by the deposited cDNA, or the amino acid sequence as shown in FIG. 1 (SEQ ID NO:2), or a fragment thereof. Preferred polypeptide fragments will have a TIF2 protein activity. In order for a TIF2 polypeptide to interact in anagonist-dependent manner with nuclear receptors and to enhance nuclear receptor-mediated transcriptional activation, such TIF2 polypeptide fragments should at least include amino acid residues 624 to 1131 as shown in FIG. 1(SEQ ID NO:2) or amino acid substitutions, additions or deletions thereof that are not significantly detrimental to the polypeptides' ability to interact in an agonist-dependent manner with nuclear receptors and to enhance nuclear receptor-mediated transcriptional activation. In order for a TIF2 polypeptide fragment to interact with the LBD of an NR without activating transcription, the TIF2 polypeptide fragments should at least include amino acids 624–869 as shown in FIG. 1 (SEQ ID NO:2), or amino acid substitutions, additions or deletions thereof that are not significantly detrimental to the polypeptides' ability to interact with the LBD of an NR. In order for a TIF2 polypeptide fragment to activate CBP-dependent transcription, the TIF2 polypeptide should at least include amino acid residues 1010–1131 as shown in FIG. 1 (SEQ ID NO:2) or amino acid substitutions, additions or deletions thereof that are not significantly detrimental to the polypeptides' ability to activate CBP-dependent transcription. For a TIF2 polypeptide to activate CBP-independent transcription, the TIF2 polypeptide should at least include amino acid residues 1288–1464 as shown in FIG. 1 (SEQ ID NO:2) or amino acid substitutions, additions or deletions thereof that are not significantly detrimental to the polypeptides' ability to activate CBP-indepentent transcription.

Exemplary TIF2 polypeptide fragments according to the present invention include cytoplasmic TIF2 polypeptides having at least one mutation or deletion in a N-terminal NLS region that interferes with the nuclear localization function. Methods for generating cytoplasmic TIF2 polypeptides are described above.

As used herein, an "isolated" polypeptide or protein is intended to mean a polypeptide or protein removed from its native environment, such as recombinantly produced polypeptides and proteins expressed in host cells and native or recombinant polypeptides which have been substantially purified by any suitable technique (e.g., the single-step purification method disclosed in Smith and Johnson, Gene 67:31–40 (1988), which is incorporated by reference herein). Isolated polypeptides or proteins according to the present invention further include such compounds produced synthetically.

The present inventors have discovered that the full-length TIF2 protein is an about 1464 amino acid residue protein with a deduced molecular weight of about 160 kDa. It will be recognized by those skilled in the art that some amino acid sequence of the TIF2 protein can be varied without significant effect on the structure or function of the protein. If such differences in sequence are contemplated, it should be remembered that there will be critical areas on the protein which determine activity, such as the region described above which has been determined by the inventors as being critical to the protein's ability to enhance nuclear receptor-mediated transcriptional activation. In general, it is often possible to replace residues which form the tertiary structure, provided that residues performing a similar function are used. In other instances, the type of residue may be completely unimportant if the alteration occurs at a non-critical region of the protein.

Thus, the present invention further includes variations of the TIF2 polypeptide which show substantial TIF2 polypeptide activity or which include regions of TIF2 protein such as the protein fragments discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and fie; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr.

As indicated in detail above, further guidance concerning which amino acid changes are likely to be phenotypically silent (i.e., not likely to have a significant deleterious effect on a function) can be found in Bowie et al., "Deciphering the Message in Protein Sequences: Tolerance to Amino Acid Substitutions," Science 247:1306–1310 (1990)).

The polypeptides of the present invention include polypeptides having an e=, amino acid sequence as encoded by the deposited cDNA, an amino acid sequence as shown in SEQ ID NO:2, as well as an amino acid sequence at least 80% identical, more preferably at least 90% identical, and most preferably at least 95%, 96%, 97%, 98%, or 99% identical, to the amino acid sequence encoded by the deposited cDNA, to the amino acid sequence as shown in SEQ ID NO:2, or to the amino acid sequence of a polypeptide fragment described above. Whether two polypeptides have an amino acid sequence that is at least 80%, 90% or 95% identical can be determined using a computer algorithm as described above.

As described in detail below, the nucleic acid molecules and polypeptides of the present invention are useful in screening assays for identifying agonist and antagonist of NR AF2-mediated transactivation. For example, in Halachmi, S., et al., Science 264: 1455 (1994), the authors show that tamoxifen, which has growth inhibitory effects in breast cancer, disrupts the formation of a complex that includes the estrogen receptor and ERAP160. Accordingly, the nucleic acid molecules and polypeptides of the present invention are useful in assays for identifying drugs capable of enhancing or inhibiting nuclear receptor-mediated pathways.

The nucleic acid molecules and polypeptides of the present invention are useful in screening assays for identifying agonists and antagonists of TIF2 AD1 activity, and in screening assays for identifying agonist and antagonists of TIF2 AD2 activity, as described in detail below.

Screening Methods

Nuclear receptors (NRs) are members of a superfamily of ligand-inducible transcriptional regulatory factors that include steroid hormone, thyroid hormone, vitamin D3 and retinoid receptors (Leid, M., et al., Trends Biochem. Sci. 1 7:427–433 (1992); Leid, M., et al., Cell 68:377–395 (1992); and Linney, E. Curr. Top. Dev. Biol., 27:309–350 (1992)). NRs exhibit a modular structure which reflects the existence of several autonomous functional domains. Based on amino acid sequence similarity between the chicken estrogen receptor, the human estrogen and glucocorticoid receptors, and the v-erb-A oncogene, Krust, A., et al., EMBO J 5:891–897 (1986), defined six regions, A, B, C, D, E and F (see FIG. 6), which display different degrees of evolutionary conservation amongst various members of the nuclear receptor superfamily. The highly conserved region C contains two zinc fingers and corresponds to the core of the DNA-binding domain (DBD), which is responsible for specific recognition of the cognate response elements. Region E is functionally complex, since in addition to the ligand-binding domain (LBD), it contains a ligand-dependent activation function (AF-2) and a dimerization interface. An autonomous transcriptional activation function (AF-1) is present in the non-conserved N-terminal A/B regions of the steroid receptors. Interestingly, both AF-1 and AF-2 of steroid receptors exhibit differential transcriptional activation properties which appear to be both cell type and promoter context specific (Gronemeyer, H. Annu. Rev. Genet. 25:89–123 (1991)).

The all-trans Cr-RA) and 9-cis (9C-RA) retinoic acid signals are transduced by two families of nuclear receptors, RAR α, β and γ (and their isoforms) are activated by both T-RA and 9C-RA, whereas RXR α, β and γ are exclusively activated by 9C-RA (Allenby, G. et al., Proc. Natl. Acad. Sci. USA 90:30–34 (1993)). The three RAR types differ in their B regions, and their main isoforms (α1 and α2, β1–4, and γ1 and γ2) have different N-terminal A regions (Leid, M. et al., Trends Biochem. Sci. 17:427433 (1992)). Similarly, the RXR types differ in their A/B regions (Mangelsdorf, D. J. et al, Genes Dev. 6:329–344 (1992)).

The E-region of RARs and RXRs has also been shown to contain a dimerization interface (Yu, V. C. et al., Curr. Opin. Biotechnol. 3:597–602 (1992)). Most interestingly, it was demonstrated that RAR/RXR heterodimers bind much more efficiently in vitro than homodimers of either receptor to a number of RA response elements (RAREs) (Yu, V. C. et al., Cell 67:1251–1266 (1991); Berrodin, T. J. et al., Mol. Endocrinol 6:1468–1478 (1992); Bugge, T. H. et al., EMBO J. 11:1409–1418 (1992); Hall, R. K. et al., Mol. Cell. Biol. 12: 5527–5535 (1992); Hallenbeck, P. L. et al., Proc. Natl. Acad. Sci. USA 89:5572–5576 (1992); Husmann, M. et al., Biochem. Biophys. Res. Commun. 187:1558–1564 (1992); Kliewer, S. A. et al, *Nature* 355:446–449 (1992b); Leid, M. et al., *Cell* 68:377–395 (1992); Marks, M. S. et al., *EMBO J* 11:1419–1435 (1992); Zhang, X. K. et al., *Nature* 355:441446 (1992)). RAR and RXR heterodimers are also preferentially formed in solution in vitro (Yu, V. C. et al., *Cell* 67:1251–1266 (1991); Leid, M. et al., *Cell* 68:377–395 (1992); Marks, M. S. et al., EMBO J. 11:1419–1435 (1992)), although the addition of 9C-RA appears to enhance the formation of RXR homodimers in vitro (Lehman, J. M. et al., *Science* 258:1944–1946 (1992); Zhang, X. K. et al., *Nature* 358:587–591 (1992b)). That RAR-RXR heterodimers, rather than the corresponding homodimers, preferentially bind to RAREs in cultured cells in vivo has been strongly supported by experiments described in Durand, B. et al., *Cell* 71:73–85 (1992).

As retinoic acid is known to regulate the proliferative and differentiative capacities of several mammalian cell types (Gudas, L. J. et al. (1994) In Sporn, M. B., Roberts, A. B. and Goodman, D. S.(eds), *The Relinoids*. 2nd edition, Raven Press, New York, pp. 443–520), retinoids are used in a variety of chemopreventive and chemotherapeutic settings. The prevention of oral, skin and head and neck cancers in patients at risk for these tumors has been reported (Hong, W. K. et al., *N. Engl. J. Med* 315:1501–1505 (1986); Hong, W. K. et al., *N. Engl. J. Med.* 323:795–801 (1990); Kraemer, K. H. et al., *N. Engl. J. Med.* 318:1633–1637 (1988); Bollag, W. et al., *Ann. Oncol.* 3:513–526 (1992); Chiesa, F. et al., *Eur. J. Cancer B. Oral Oncol.* 28:97–102 (1992); Costa, A. et al., *Cancer Res.* 54:Suppl. 7, 2032–2037 (1994)), and retinoids are used in the therapy of acute promyelocytic leukemia (Huang, M. E. et al., *Blood* 72:567–572 (1988); Castaigne, S. et al., *Blood* 76:1704–1709 (1990); Chomienne, C. et al., *Blood* 76:1710–1717 (1990); Chomienne, C. et al., *J. Clin. Invest.* 88:2150–2154 (1991); Chen Z. et al., *Leukemia* 5:288–292 (1991); Lo Coco, F. et al., *Blood* 77:165701659 (1991);Warrefl,R. P., Jr. et al., *N. Engl. J. Med.* 324:1385–1393 (1991)), squamous cell carcinoma of the cervix and the skin (Verma, A. K., *Cancer Res.* 47:5097–5101 (1987); Lippman S. M. et al.,*J. Natl. Cancer Inst.* 84:235–241 (1992); Lippman S. M. et al., *J. Natl. Cancer Inst.* 84:241–245 (1992)) and. Kaposi sarcoma (Bonhomme, L. et al., *Ann. Oncol.* 2:234–235 (1991)).

For example, in Chen, J-Y et al., *EMBO J.* 14 (6):1187–1197 (1995), a number of dissociating synthetic retinoids are characterized that selectively induce AF-2 activation function present in the LBD of RARβ ((βAF-2). The authors also report that these synthetic retinoids, like RA, can inhibit the anchorage-independent growth of oncogene-transformed 3T3 cells. Further, the promoter of the human interdeukin-6 (IL-6) gene, whose product is involved in the regulation of hematopoiesis, immune responses and inflammation (Kishimoto, T. et al., *Science* 258:593–597 (1992)), is induced by RA but not by the 'dissociating' retinoids which repressed its activity.

In addition to the retinoid receptors, compounds with agonistic and antagonistic properties on functions of the steroid receptors have also been reported. For example, in Meyer, M-E. et al., *EMBO J.* 9 (12): 3923–3932 (1990), a transient expression/gel retardation system was used to study the effects of RU486 and R5020 on glucocorticoid and progesterone receptor function. Further, in Halachimi, S., et al., *Science* 264:1455–1458 (1994), tamoxifen is shown to competitively inhibit estradiol-induced ERAP160 binding to the estrogen receptor, suggesting a mechanism for its growth-inhibitory effects in breast cancer. Accordingly, due to their clinical importance, there is great interest in developing screening methods capable of identifying agonist and antagonist of nuclear receptor transactivation.

As indicated, the present inventors have cloned a gene encoding TIF2 and have shown that TIF2 and a cytoplasmic fragment thereof bind, in an agonist-dependent manner, to all nuclear receptors analyzed—RAR, RXR, ER, TR, VDR, GR and AR. Further, the present inventors have shown that TIF2 polypeptides are transcriptional mediators of the nuclear receptor AF-2. Thus, the present invention further provides a screening method for identifying a nuclear receptor (NR) antagonist, which involves: (a) providing a host cell containing recombinant genes which express a polypeptide comprising a NR ligand binding domain (LBD) and a polypeptide comprising transcriptional intermediary factor-2 (TIF-2) or a TIF-2-fragment, wherein, in the presence of an agonist, said TIF-2 and said TIF-2-fragment bind said NR LBD; (b) administering a candidate antagonist to said cell; and (c) determining whether said candidate antagonist reduces either: (1) TIF-2- or TIF-2-fragment-binding to the AF-2 of said NR LBD as compared to said binding in the absence of said candidate antagonist; or (2) TIF-2- or TIF-2-fragment-stimulated NR LBD AF-2-mediated transactivation as compared to said transactivation in the absence of said candidate antagonist.

In a further aspect, a screening method is provided for identifying a nuclear receptor (NR) agonist, which involves: (a) providing a host cell containing recombinant genes which express a polypeptide comprising a NR ligand binding domain (LLBD) and a polypeptide comprising transcriptional intermediary factor-2 (TIF-2) or a TIF-2-fragment, wherein, in the presence of an agonist, said TrF-2 and said TIF-2-fragment bind said NR LBD; (b) administering a candidate agonist to said cell; and (c) determining whether said candidate agonist enhances either: (1) TIF-2- or TIF-2-fragment-binding to the AF-2 of said NR LBD as compared to said binding in the absence of said candidate agonist; or (2) TIF-2- or TIF-2-fragment-stimulated NR LBD AF-2-mediated transactivation as compared to said transactivation in the absence of said candidate agonist.

By "a host cell containing recombinant genes" is intended host cells into which one or more of the recombinant constructs described herein have been introduced or a progeny of such host cells.

Candidate antagonist and agonist according to the present invention include 'dissociating' ligands for nuclear receptors such as those described in Chen et al., *EMBO J* 14:1187–1197 (1995) and Ostrowski et al, *Proc. Natl. Acad. Sci. USA* 92:1812–1816 (1995). Progesterone and glucocorticoid receptor agonist and antagonist are described in Meyer et al., EMBO J. 9 (12): 3923–3932 (1990). An estrogen receptor antagonist is described in Halachmi et al., *Science* 264:1455–1458 (1994). Thus, methods are known in the art for developing candidate nuclear receptor agonist and antagonist for screening according to the present invention. For example, the crystal structure of the ligand binding domains of certain nuclear receptors have been described. In particular, the crystal structure of the RXR LBD is described in Bourguet et al., *Nature* 375:377–382 (1995); the crystal structure of the RAR LBD is described in Renaud et al., *Nature* 378:681–689 (1995); and the crystal structure of a thyroid hormone receptor is described in Wagner et al., *Nature* 378:690–697 (1995). Using information from the crystal structure of a nuclear receptor, computer programs are available for designing the structure of candidate agonist and antagonist which would likely bind to the ligand binding domain. Suitable computer program packages for this purpose include WHAT IF (Vriend, G., *J. Mol. Graphics*

8:52–56 (1990)), and GRID (Goodford, *J. Med. Chem.* 28:849–857 (1985)).

Recombinant genes encoding a polypeptide comprising TIF2 or a TIF2-fragment capable of binding nuclear receptors in an agonist-dependent manner are described above. Recombinant genes encoding a polypeptide comprising a NR LBD have been described in great detail in the art. Methods for determining whether a candidate agonist or antagonist enhances or interferes with TIF-2 or TIF-2-fragment binding to a NR are known in the art. For example, the effect of a candidate agonist or antagonist on TIF2- or TIF-2-fragment-binding to a NR LBD can be studied using glutathione-S-transferase (GST) interaction assays by tagging NR LBDs with GST as described in detail in the Experimental section below and in Le Douarin et al., *EMBO J.* 14:2020–2033 (1995).

Where the effect of a candidate agonist or antagonist on NR AF-2 transactivation is to be assayed, preferably, the recombinant genes will encode a chimeric polypeptide comprising a NR LBD fused to a DNA binding domain from a transactivator protein. In a further preferred embodiment, the host cell epressing the recombinant genes will also express a reporter gene. For example, in Chen et al., *EMBO J.* 14 (6): 1187–1197 (1995), three 'reporter' cell lines have been established in which RARα, RARβ, or RARγ agonists induce luciferase activity that can be measured in the intact cells using a single-photon-counting camera. These cell lines stably express chimeric proteins containing the DNA binding domain of the yeast transactivator GALA fused to the EF regions (which contain that LBD and the AF-2 activation function) of RARα (GAL-RARα), RARβ (GAL-RARβ) or RARγ (GAL-RARγ), and a luciferase reporter gene driven by a pentamer of the GAL4 recognition sequence ('17m') in front of the β-globin promoter (17mx5-G-Luc). This reporter system is insensitive to endogenous receptors which cannot recognize the GAL4 binding site. Further examples of reporter genes and reporter expression vectors for use according to the present invention to screen candidate agonist and antagonist of retinoid receptors are provided in FIG. 6.

The ER expression vectors HEO, HE19 and HE15, the GR expression vectors HG1 and HG3 and the PR expression cPR1 and cPR3 are described in Kumar et al., *Cell* 51:941–951 (1987) and Gronemeyer et al., *EMBO J.* 6:3985–3994 (1987). The GR expression vector HG8 and the PR expression vector cPR5A are described in Bocquel et al., *Nucl. Acids Res.* 17:2581–2595 (1989). Reporter genes for the above described ER, GR and PR expression vectors include MMTV-CAT (in the case of PR and GR; Cato et al., *EMBO J:* 5:2237–2240 (1986)) and vit-tk-CAT (in the case of ER; Klein-Hitpass et al., *Cell* 41:1055–1061 (1986)).

The TR expression vector LexA-TR is described in Lee et al., *Nature* 374:91–94 (1995), which also describes using the yeast two hybrid system to identify compounds that affect TR transactivation.

Still further references disclosing reporter plasmids containing a reporter gene and expression vectors encoding a NR LBD include Meyer et al., *Cell* 57:433–442 (1989); Meyer et al., *EMBO J.* 9 (12):3923–3932 (1990); Tasset et al., *Cell* 62:1177–1187 (1990); Gronemeyer, H. and Laudet, V., *Protein Profile* 2:1173–1308 (1995); Webster et al., *Cell* 54:199–207 (1988); Stramhe et al., *EMBO J.* 7:3389–3395 (1988); Seipel et al., *EMBO J.* 11:4961–4968 (1992); and Nagpal et al., *EMBO J.* 12:2349–2360 (1993). In a particularly preferred embodiment, the effect of a candidate agonist or antagonist on NR AF-2-mediated transactivation is assayed according to the method described in the legend to FIG. 5 above.

The present inventors have identified an activation domain of TIF2, AD1 (amino acids 1010–1131 as shown in FIG. 1 (SEQ ID NO:2)), which mediates the CBP-dependent transcriptional activation function of TIF2. Further, the present inventors have shown that polypeptides containing this activation domain, when fused to a DNA-binding domain of a transcriptional activator, is capable of activating transcription via a CBP-dependent pathway. Accordingly, the present invention further provides a screening method of identifying an agonist of TIF2 AD1 activation domain activity, which involves: (a) providing a host cell containing a recombinant gene or genes which express a polypeptide comprising a transcriptional activator DNA-binding domain (DBD) and a TEF-2 AD1 activation domain 1; (b) administering a candidate agonist to said cell; and (c) determining whether said candidate agonist enhances TIF2 AD1 activation domain activity.

The invention further provides for a screening method for identifying an antagonist of TIF2 AD1 activation domain activity, which comprises: (a) providing a host cell containing a recombinant gene or genes which express a polypeptide comprising a transcriptional activator DNA-binding domain (DBD) and a TIF-2 AD1 activation domain 1; (b) administering a candidate antagonist to said cell; and (c) determining whether said candidate antagonist inhibits TIF2 AD1 activation domain activity.

By "transcriptional activator" it is meant molecules that enhance the initiation of transcription by RNA polymerase B (II). Transcriptional activators include yeast transcriptional activators, such as GAL4 and GCN4; the herpes simplex activator, VP16; and members of the nuclear receptor family, which includes RAR, RXR, ER, TR, VDR, GR, and AR.

Recombinant genes encoding a polypeptide comprising a TIF2 AD1 activation domain are described below. Recombinant genes encoding a polypeptide comprising a transcriptional activator DBD are well known in the art. Methods for determining whether a candidate agonist or antagonist enhances or interferes with transcription are well known in the art. For example, the effect of a candidate agonist or antagonist of TIF2 AD1 activation domain activity can be determined using CAT assays as described below and in Gronemeyer et al. (1987) and Bocquel et al., *Nucl. Acids Res.* (1989).

Where the effect of a candidate agonist or antagonist of TIF2 AD1 activation domain activity is to be determined, preferably, recombinant genes will encode a chimeric polypeptide comprising a transcriptional activator DBD fused to a TIF2 polypeptide comprising the AD1 activation domain. In a further embodiment, the host cell expressing the recombinant genes will also express a reporter gene. Examples of reporter genes are described above. In a particularly preferred embodiment, the effect of a candidate agonist or antagonist of TIF2 AD1 activation domain function will be determined as described in the legend to FIG. 7(*c*).

The present inventors have also identified a second activation domain of TIF2, AD2 (amino acids 1288–1464 as shown in FIG. 1 (SEQ ID NO:2)), which mediates CBP-independent transcriptional activation. Further, the present inventors have shown that polypeptides containing this activation domain, when fused to a DNA-binding domain of a transcriptional activator, are capable of activating transcription via a CBP-independent pathway. Accordingly, the present invention further provides a screening method for identifying an agonist of TIF2 AD2 activation domain activity, which comprises: (a) providing a host cell containing a recombinant gene or genes which express a polypeptide comprising a transcriptional activator DNA-binding-domain (DBD) and a TIF-2. AD2 activation domain; (b) administering a candidate agonist to said cell; and (c) determining whether said candidate agonist enhances TIF2 AD2 activation domain activity.

The invention further provides for a screening method for identifying an antagonist of TIF2 AD2 activation domain activity, which comprises: (a) providing a host cell containing a recombinant gene or genes which express a polypeptide comprising a transcriptional activator DNA-binding domain (DBD) and a TIF-2 AD2 activation domain; (b) administering a candidate antagonist to said cell; and (c) determining whether said candidate antagonist inhibits TIF2 AD2 activation domain activity.

Recombinant genes encoding a polypeptide comprising a TIF2 AD2 activation domain are described below. Recombinant genes encoding a polypeptide comprising a transcriptional activator DBD are well known in the art. Methods for determining whether a candidate agonist or antagonist enhances or interferes with transcription are known in the art. Where the effect of a candidate agonist or antagonist of TIF2 AD2 activation domain activity is to be determined, preferably, recombinant genes will encode a chimeric polypeptide comprising a transcriptional activator DBD fused to a TIF2 polypeptide comprising the AD2 activation domain. Transcriptional activators are described above. In a further embodiment, the host cell expressing the recombinant genes will also express a reporter gene. Examples of reporter genes are described above. In a particularly preferred embodiment, the effect of a candidate agonist or antagonist of TIF2 AD2 activation domain activity will be determined as described in the legend to FIG. 7(c).

TIF-2 Antibodies and Methods

TIF2 antibodies are also provided by the present invention, as specific for a TIF2 protein, a TIF2 polypeptide, a TIF2 protein fragment or a TIF2 polypeptide fragment. The term "antibody" is meant to include polyclonal antibodies, monoclonal antibodies (mAbs), chimeric antibodies, anti-idiotypic (anti-Id) antibodies to antibodies that can be labeled in soluble or bound form, as well as fragments thereof provided by any known technique, such as, but not limited to enzymatic cleavage, peptide synthesis or recombinant techniques. Polyclonal antibodies are heterogeneous populations of antibody molecules derived from the sera of animals immunized with an antigen. A monoclonal antibody contains a substantially homogeneous population of antibodies specific to antigens, which population contains substantially similar epitope binding sites. MAbs may be obtained by methods known to those skilled in the art. See, for example Kohler and Milstein, *Nature* 256:495–497 (1975); U.S. Pat. No. 4,376,110; Ausubel et al, eds., CURRENT PROTOCOLS IN MOLECULAR BIOLOGY, Greene Publishing Assoc. and Wiley Interscience, N.Y., (1987–1996); and Harlow and Lane ANTIBODIES: A LABORATORY MANUAL Cold Spring Harbor Laboratory (1988); Colligan et al., eds., *Current Protocols in Immunology*, Greene Publishing Assoc. and Wiley Interscience, N.Y., (1992–1996), the contents of which references are incorporated entirely herein by reference. Such antibodies may be of any immunoglobulin class including IgG, IgM, IgE, IgA, GILD and any subclass thereof A hybridoma producing a mAb of the present invention may be cultivated in vitro, in situ or in vivo. Production of high titers of mAbs in vivo or in situ makes this the presently preferred method of production.

Chimeric antibodies are molecules different portions of which are derived from different animal species, such as those having variable region derived from a murine mAb and a human immunoglobulin constant region, which are primarily used to reduce immunogenicity in application and to increase yields in production, for example, where murine mAbs have higher yields from hybridomas but higher 0:3; immunogenicity in humans, such that human/murine chimeric mAbs are used. Chimeric antibodies and methods for their production are known in the art (Cabilly _et al., *Proc. Natl. Acad. Sci. USA* 81:3273–3277 (1984); European Patent Application 125023 (published Nov. 14, 1984); Neuberger et al., *Nature* 314:268–270 (1985); Taniguchi et al, European Patent Application 171496 ((1985); Morrison et al., European Patent Application 173494 (1986); Neuberger et al, PCT Application WO 86/01533, (1986); Kudo et al., European Patent Application 184187 (1986); Morrison et al., European Patent Application 173494 (1986); Robinson et al., PCT Publication PCT/US86/02269 (1987); Liu et al, Proc. Nall. Acad. Sci. USA 84:3439–3443 (1987); Sun et al., *Proc. Natl. Acad. Sci. USA* 84:214–218 (1987); Better et al., *Science* 240:1041–1043 (1988); and Harlow and Lane, ANTIBODIES: A LABORATORY MAUAL Cold Spring Harbor Laboratory (1988)). These references are entirely incorporated herein by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an "immunogen" to induce an immune response in yet another animal, producing a so-called anti-anti-Id antibody. The anti-anti-Id may be epitopically identical to the original mnAb which induced the anti-Id. Thus, by using antibodies to the idiotypic determinants of a mAb, it is possible to identify other clones expressing antibodies of identical specificity. The anti-Id mAbs thus have their own idiotypic epitopes, or "idiotopes" structurally similar to the epitope being evaluated, such as GRB protein-α.

The term "antibody" is also meant to include both intact immunoglobulin molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316–325 (1983)). It will be appreciated that Fab and F(ab') and other fragments of the antibodies useful in the present invention may be used for the detection and quantitation of a TIF2 according to the methods disclosed herein for intact antibody molecules. Such fragments are typically produced by proteolytic cleavage, using enzymes such as papain (to produce Fab fragments) or pepsin (to produce F(ab')$_2$ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that anti-body. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one, or more than one epitope. The specific reaction referred to above is meant to indicate that the antigen will react, in a highly selective manner, with its corresponding antibody and not with the multitude of other antibodies which may be evoked by other antigens.

The antibodies, or fragments of antibodies, useful in the present invention may be used to quantitatively or qualitatively detect a TIF2 protein, polypeptide, or fragment, in a sample or to detect presence of cells which express a TIF2 of the present invention. This can be accomplished by immunofluorescence techniques employing a fluorescently labeled antibody (see below) coupled with light microscopic, flow cytometric, or fluorometric detection.

The antibodies (of fragments thereof) useful in the present invention may be employed histologically, as in immunofluorescence or immunoelectron microscopy, for in situ detection of a TIF2 protein, polypeptide, or fragment, of the present invention. In situ detection may be accomplished by removing a histological specimen form a patient, and providing a labeled antibody of the present invention to such a specimen. The antibody (or fragment) is preferably provided by applying or by overlaying the labeled antibody (or fragment) to a biological sample. Through the use of such a procedure, it is possible to determine not only the presence of a TIF2 protein, polypeptide, or fragment, but also its distribution on the examined tissue. Using the present invention, those of ordinary skill will readily perceive that any of wide variety of histological methods (such as staining procedures) can be modified in order to achieve such in situ detection.

Such assays for a TIF2 protein, polypeptide, or fragment, of the present invention typically comprises incubating a biological sample, such as a biological fluid, a tissue extract, freshly harvested cells such as lymphocytes or leukocytes, or cells which have been incubated in tissue culture, in the presence of a detectably labeled antibody capable of identifying a TIF2 protein, polypeptide, or fragment, and detecting the antibody by any of a number of techniques well-known in the art.

The biological sample may be treated with a solid phase support or carrier such as nitrocellulose, or other solid support or carrier which is capable of immobilizing cells, cell particles or soluble proteins. The support or carrier may then be washed with suitable buffers followed by treatment with a detectably labeled TIF2-specific antibody. The solid phase support or carrier may then be washed with the buffer a second time to remove unbound antibody. The amount of bound label on said solid support or carrier may then be detected by conventional means.

By "solid phase support", "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, or cylindrical, as in the inside surface of a test tube, or the external surface of a rod. Alternatively, the surface may be flat such as a sheet, test strip, etc. Preferred supports or carriers include polystyrene beads. Those skilled in the art will know many other suitable carriers for binding antibody or antigen, or will be able to ascertain the same by use of routine experimentation.

The binding activity of a given lot of anti-TIF2 antibody may be determined according to well known methods. Those skilled in the art will be able to determine operative and optimal assay conditions for each determination by employing routine experimentation. Other such steps as washing, stirring, shaking, filtering and the like may be added to the assays as is customary or necessary for the particular situation.

One of the ways in which a TIF2-specific antibody can be detectably labeled is by linking the same to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactivity labeling the antibodies or antibody fragments, it is possible to detect R-PTPase through the use of a radioimmunoassay (RIA). A good description of RIA maybe found in Laboratory Techniques and Bio chemistry in Molecular Biology, by Work, T. S. et al., North Holland Publishing Company, NY (1978) with particular reference to the chapter entitled "An Introduction to Radioimmune Assay and Related Techniques" by Chard, T., incorporated by reference herein. The radioactive isotope can be detected by such means as the use of a $\gamma$ counter or a scintillation counter or by autoradiography.

It is also possible to label an anti-TIF2 antibody with a fluorescent compound. When the fluorescently labeled antibody is exposed to light of the proper wave length, its presence can be then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$EU, or others of the lanthanide series. These metals can be attached to the antibody using such metal chelating groups as diethylenetriamine pentaacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An antibody molecule of the present invention may be adapted for utilization in a immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen form the sample by formation of a binary solid phase antibody-antigen complex. After a suitable incubation period, the solid support or carrier is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support or carrier through the unlabeled antibody, the solid support or carrier is washed a second time to remove the unreacted labeled antibody.

In another type of "sandwich" assay, which may also be useful with the antigens of the present invention, the so-called "simultaneous" and "reverse" assays are used. A "simultaneous" and "reverse" assays are used. A simultaneous assay involves a single incubation step as the antibody bound to the solid support or carrier and labeled antibody are both added to the sample being tested at the same time. After the incubation is completed, the solid support or carrier is washed to remove the residue of fluid sample and uncomplexed labeled antibody. The presence of labeled antibody associated with the solid support or carrier is then determined as it would be in a conventional "forward" sandwich assay.

In the "reverse" assay, stepwise addition first of a solution of labeled antibody to the fluid sample followed by the addition of unlabeled antibody bound to a solid support or carrier after a suitable incubation period is utilized. After a second incubation, the solid phase is washed in conventional fashion to free it of the residue of the sample being tested and the solution of unreacted labeled antibody. The determination of labeled antibody associated with a solid support or carrier is then determined as in the "simultaneous" and "forward" assays.

Having generally described the invention, the same will be more readily understood by reference to the following examples, which are provided by way of illustration and are not intended as limiting.

EXAMPLE 1

TIF2 Cloning and Expression

In keeping with previous reports (Halachmi, S. et al., Science 264:1455–1458 (1994); Cavaillès, V. et al., Proc. Natl. Acad. Sci. USA 91:10009–10013 (1994); Kurokawa, R. et al, Nature 377:451–454 (1995)), we observed agonist-dependent binding in vitro of a 160-kDa protein from $^{35}$S-labelled whole cell extracts (HeLa, Cos-1, P19.6, MCF-7) to the glutathione-S-transferase (GST)-tagged LBDs of retinoic acid (RAR) and estrogen (ER) receptors (FIG. 2a). One cDNA clone, identified by screening 340,000 clones of a human placenta cDNA expression library with an estradiol (E2)-bound $^{32}$P-labelled ER(DEF) probe, encoded a protein fragment (TIF2.1) that interacted on Far-Western blots with three different $^{32}$P-labelled NR LBDs (ER, RAR, RXR) in an agonist-dependent manner (not shown), and could therefore correspond to the above 160-kDa protein. The TIF2 coding sequence (FIG. 3a), preceded by in-frame stop codons 5' of the initiator AUG, was obtained upon rescreening with a TIF2.1 cDNA probe. Human TIF2 cDNA encodes a 159,160 Da protein (1,464 amino acids), which includes N-terrinal putative nuclear localization signals (NLSs), one Gln- and three Ser/Thr-rich regions, and two charged clusters (FIG. 3). Some regions of TIF2 show significant sequence similarities with the recently described (Onate, S. A. et al., Science 270:1354–1357 (1995)) steroid receptor coactivator SRC-1 (FIG. 3). TIF2 appears to be widely expressed, since the corresponding transcript was found in several human tissues, albeit at a much lower level in kidney (FIG. 2c and not shown).

Immunodepletion studies strongly support that TIF2 is the 160-kDa protein species which interacts in an agonist-dependent manner with NR LBDs (see above and Halachmi, S. et al., Science 264:1455–1458 (1994); Cavaillès, V. et al., Proc. Natl. Acad. Sci. USA 91:10009–10013 (1994); and Kurokawa, R. et al, Nature 377:451–454 (1995)). Western blotting with a rabbit antiserum (pα-TIF2), raised against bacterially expressed TIF2.1, revealed predominantly a 160-kDa HeLa cell protein that interacted with agonist-bound GST-ER(DEF) (FIG. 2b, lanes 1 and 2; see also legend to FIG. 2b). Immunodepletion with a mouse monoclonal TIF2 antibody (ma-TIF2) prior to affinity purification resulted in a specific decrease of TIF2, but not TIF1 (Le Douanin, B. et al, EMBO J. 14:2020–2033 (1995)) amounts, retained on E2-bound GST-ER(DEF) (FIG. 2b, compare lanes 2 with 4 and 6 with 8). Importantly, the subsequent Far-Western analysis with an E2-bound $^{32}$P-GST-ER(DEF) probe revealed the 160-kDa species only in control, but not TIF2-immunodepleted extracts (FIG. 2b, compare lanes 10 and 12).

Figures 4A, 4B, 4C:
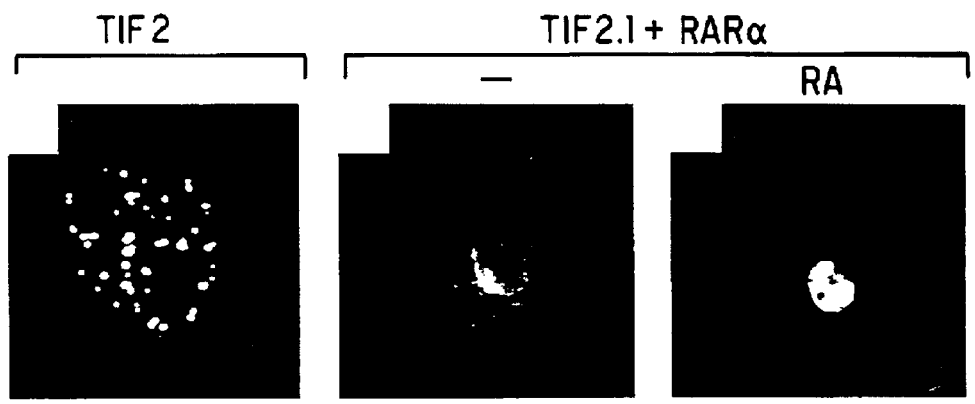
Figures 4D, 4E, 4F:
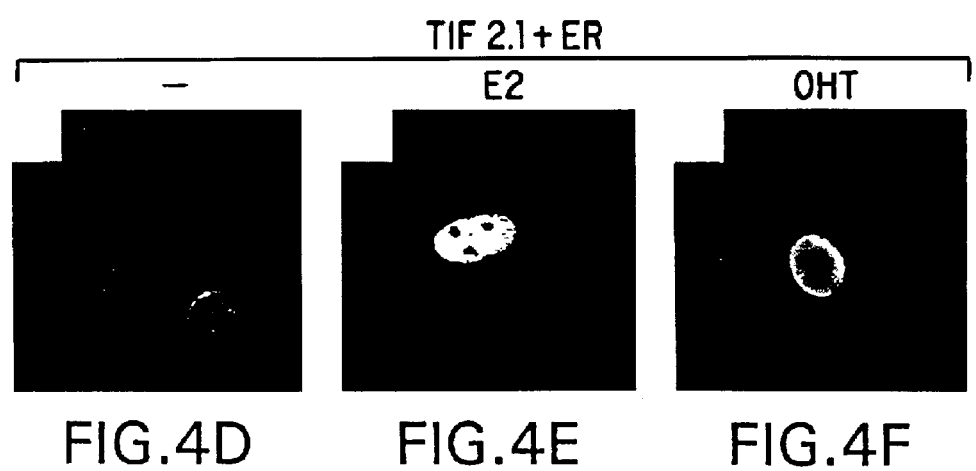
Figures 4G, 4H, 4I:
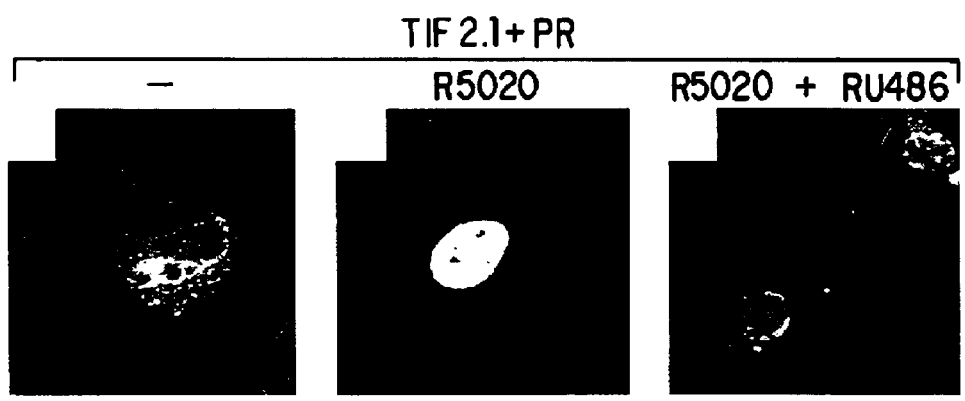

Transiently expressed full-length TIF2 was nuclear and mainly associated with discrete bodies (FIG. 4a). Since the overexpressed TIF2.1 fragment was essentially cytoplasmic (supporting the above assignment of a N-terminal TIF2 NLS), the interaction of TIF2.1 with NRs could be studied in mammalian cells using nuclear cotranslocation assays. In the absence of ligand, TIF2.1 remained cytoplasmic and NRs were nuclear (for RARα, ER and PR, see FIGS. 4b, d, g). Agonist exposure, however, resulted in all three cases in nuclear colocalization of TIF2.1 and NR, indicating NR-TIF2 interaction in vivo (FIGS. 4c, e, h). Agonist-dependent interaction of TIF2.1 with NRs was observed for all other receptors analyzed (RXR, TR, VDR, GR and AR; not shown). Interestingly, no interaction was detected between ER and TIF2.1 in presence of the ER AF-2 antagonist hydroxytamoxifen (OHMI) (FIG. 4f), and the PR AF-2 antagonist RU 486 reversed the R5020-induced PR-TIF2.1 interaction (FIG. 4i).

Figure 4K:
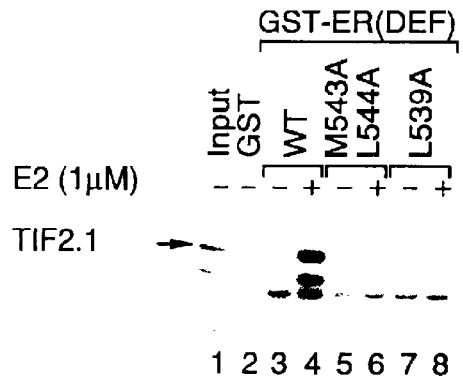
Figure 4L:
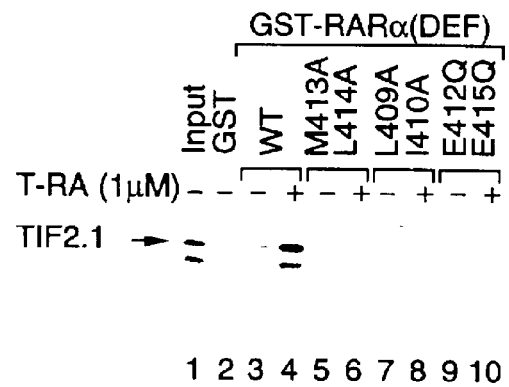
Figure 4M:
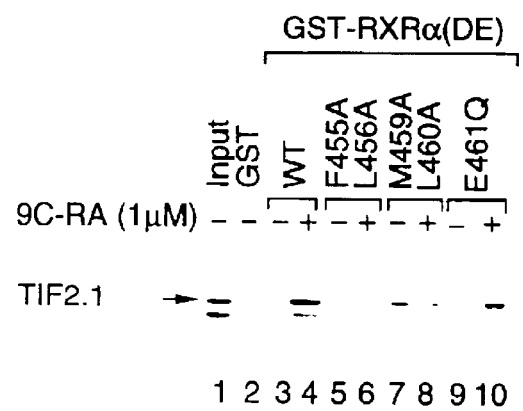
Figure 4N:
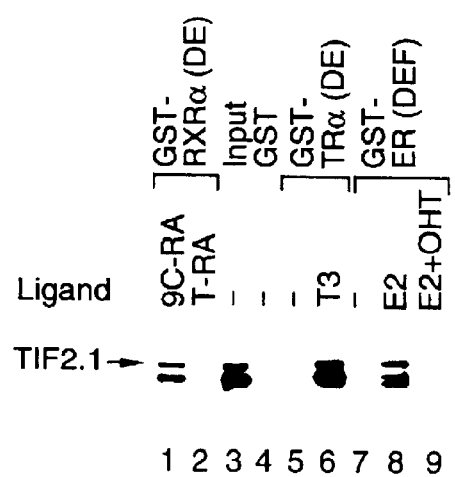

In agreement with the Far-Western blot experiments NRs and TIF2 directly interacted, as purified TIF2.1 protein bound in vitro in the presence of an agonist to GST-ER (DEF), GST-RARα(DEF), GST-RXRα(DE) and GST-TR (DE) (FIG. 4k, l, m, lanes 3 and 4; FIG. 4n, lanes 5 and 6). As expected, TIF2 binding to GST-RXRα(DE) occurred with 9cis-RA (9C-RA) but not all -trans-RA (T-RA) (FIG. 4n, lanes 1 and 2), and OHT prevented E2-dependent binding of TIF2 to GST-ER(DEF) (FIG. 4n, lanes 7–9). The integrity of the conserved core of the ER, RARα and RXRα AF-2 activating domains (AF-2 AD) which was shown to be critical for AF-2 activity (Le Douarin, B. et al, EMBO J 14:2020–2033 (1995); Danielian, P. S. et at., EMBO J. 11:1025–1033 (1992); Durand, B. et al., EMBO J. 13:5370–5382 (1994); and Gronemeyer, H. and Laudet, V., Protein Profile 2:1173–1308 (1995), and therein), was required for TIF2 interaction in vitro. Most AF-2 AD core mutants which have lost AF-2 activity (ER, FIG. 4k, lanes 5–8; RARα, FIG. 4l, lanes 5–10; RXRα, FIG. 4m, lanes 5–8) did not detectably, or only weakly, associate with TIF2, whereas the GST-LBD fusion of the RXRα mutant E461Q, whose AF-2 is only partially impaired (Le Douarin, B. et al., EMBO J. 14:2020–2033 (1995)), still exhibited a significant RA-dependent interaction with TIF2.1 in vitro (FIG. 4m, lanes 9 and 10). No significant interaction of TIF2.1 was observed with either GST-VP16 (acidic activation domain), GST-TBP, GST-TFIIB, or a series of GST-TAFs (hTAF$_n$18, hTAF$_n$20, hTAF$_n$28and hTAF$_n$55; see Jacq, X. et al., Cell 79:107–117 (1994); Mengus, G. et al., EMBO J. 14:1520–1531 (1995)) (not shown).

Figure 5A:
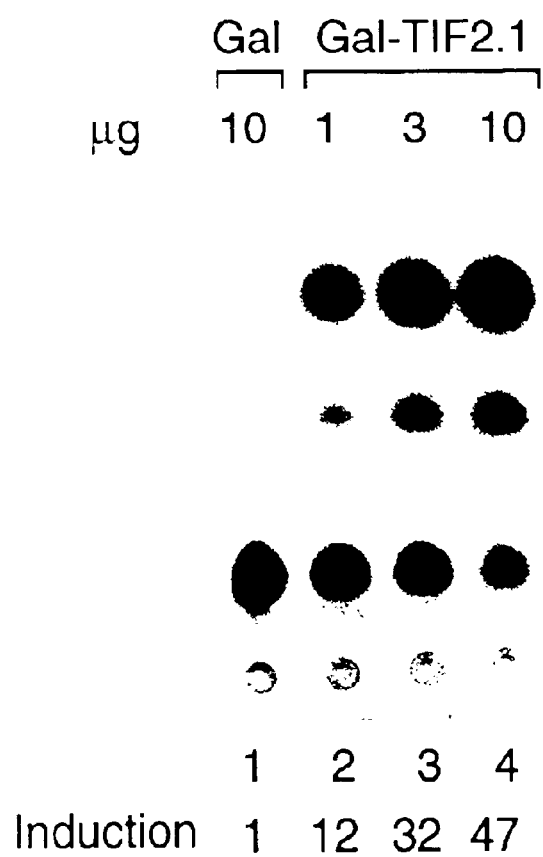
Figure 5B:
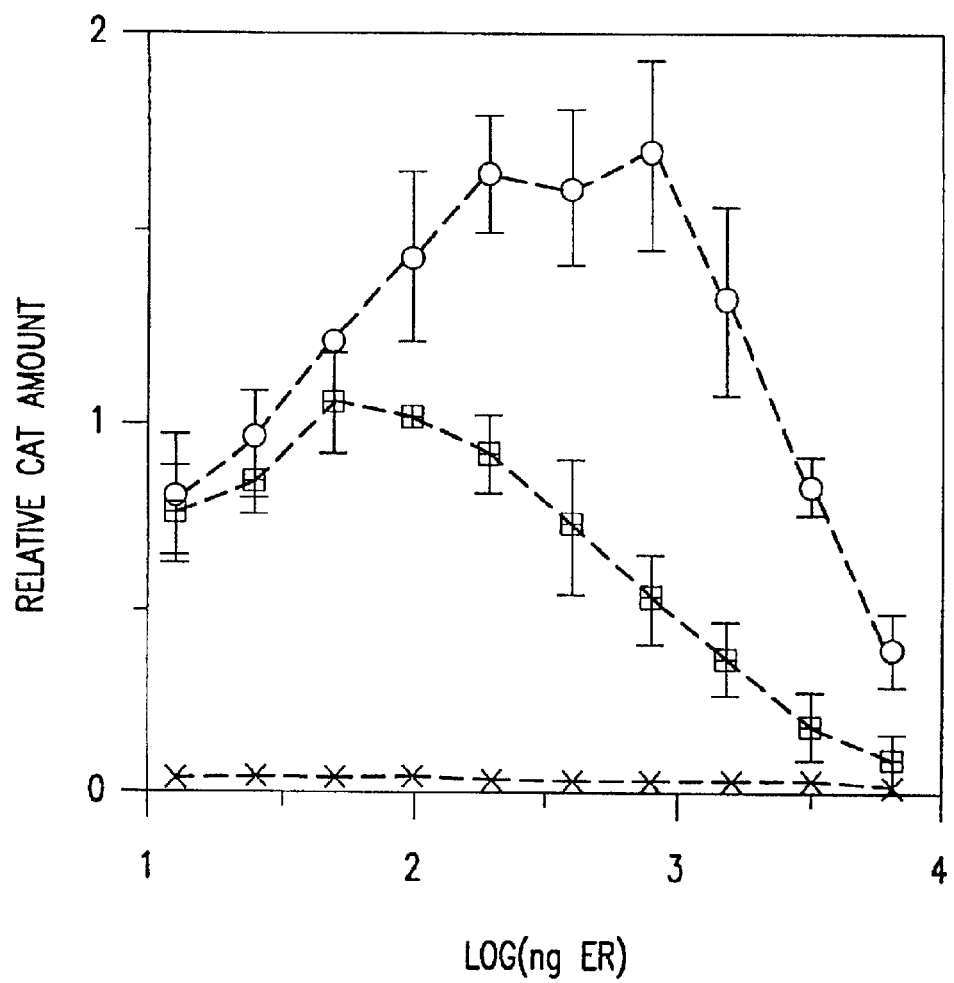

Conceptually, a TIF capable of mediating the transcriptional activity of a cognate AF to the transcription machinery, could itself be an activator when fused to a heterologous DNA-binding domain. Interestingly, in transiently transfected HeLa cells, TIF2.1 fused to the GAL4 DNA-binding domain strongly transactivated a GALA reporter (FIG. 5a). Thus, TIF2 may correspond to one of the hypothetical limiting factor(s) previously proposed to be involved in NR transcriptional interference/squelching (Meyer, M.-E. et al., Cell 57:433–442 (1989); Bocquel, M.-T. et al., Nucl. Acids Res. 17:2581–2595 (1989); Tasset, D. et al., Cell 62:1177–1187 (1990)). Supporting this possibility, "anti-squelching" experiments showed that expression of TIF2.1 in ER-transfected cells could, at least partially, reverse the transcriptional autointerference (Bocquel, M.-T. et al., Nucl. Acids Res. 17:2581–2595 (1989)) generated by expressing increased amounts of ER (FIG. 5b; note the marked shift of the bell-shaped activation curve to higher ER concentrations in the presence of 77F2.1). At high ER expression levels, the TIF2.1-stimulated transactivation decreased, possibly due to squelching of other putative mediators (Jacq, X. et al., Cell 79:107–117 (1994); Lee, J. W. et al., Nature 374:91–94 (1995); Le Douarin, B. et al., EMBO J. 14:2020–2033 (1995), vom Baur, E. et al., EMBO J. 15:110–124 (1996); Lee, J. W. et al., Endocrinology 9:243–254 (1995); Cavailles, V. et al., EMBO J. 14:3741–3751 (1995); Onate, S. A et al, Science 270:1354–1357 (1995)) and/or transcriptional factors.

Figure 5C:
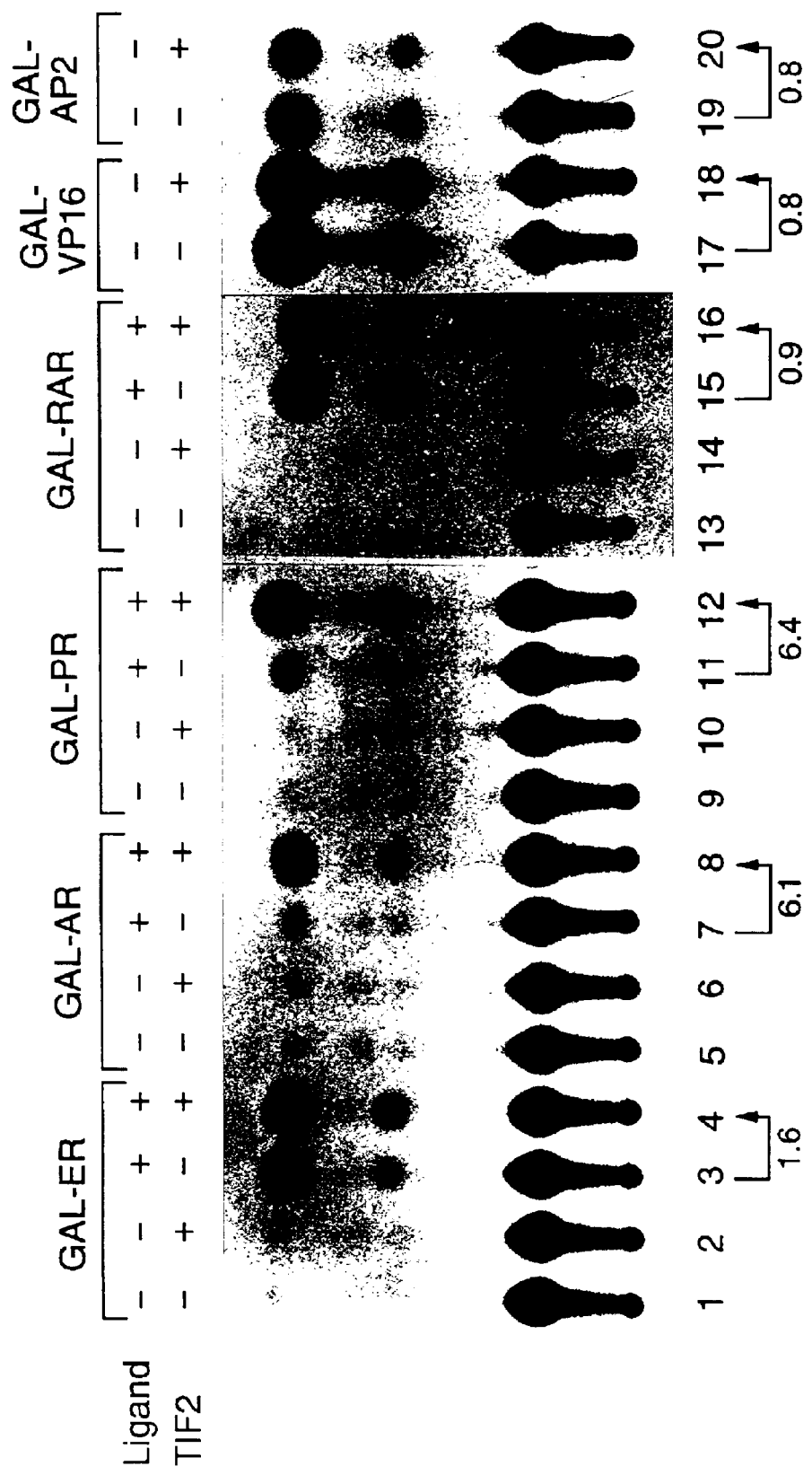
Figure 5D:
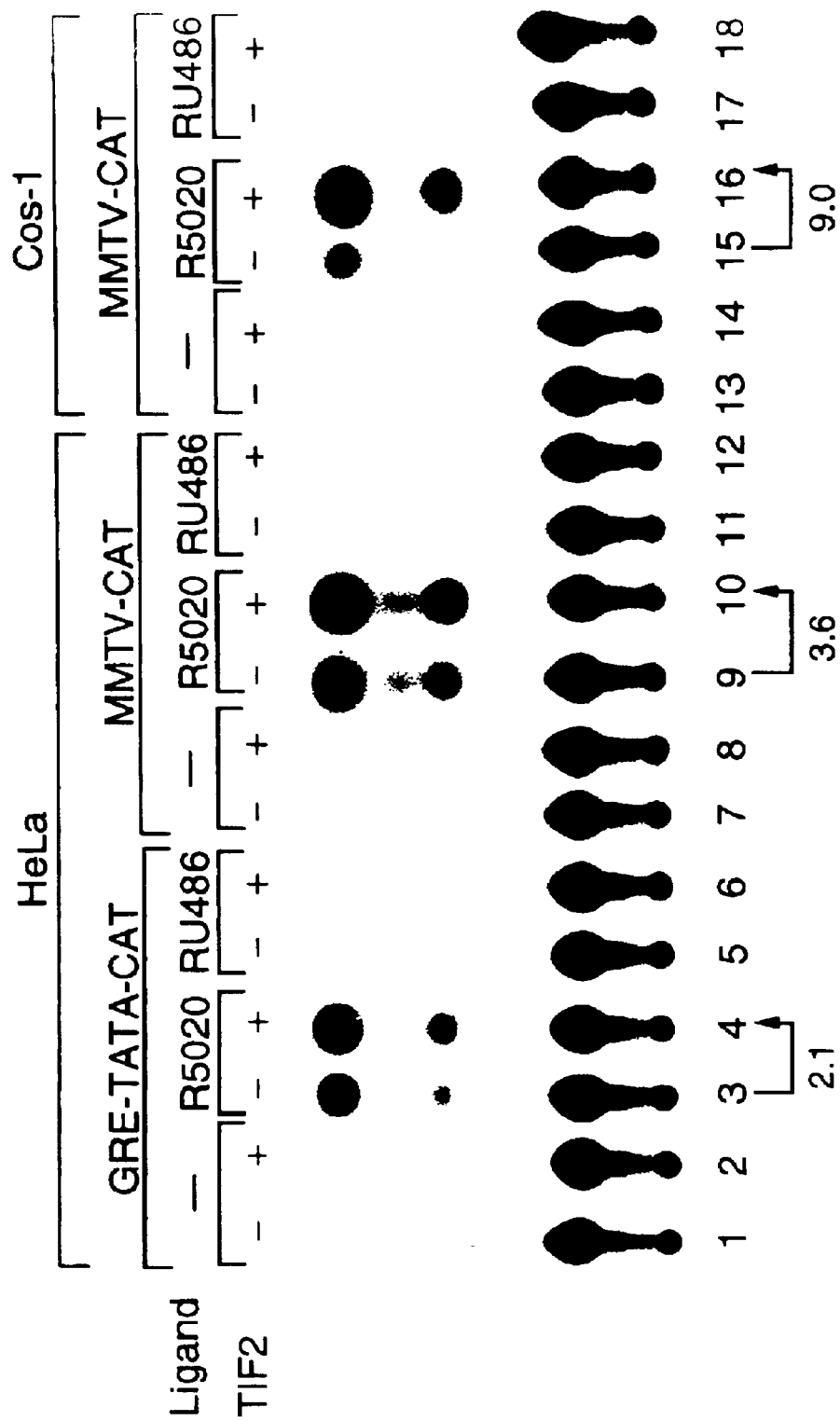
Figure 5E:
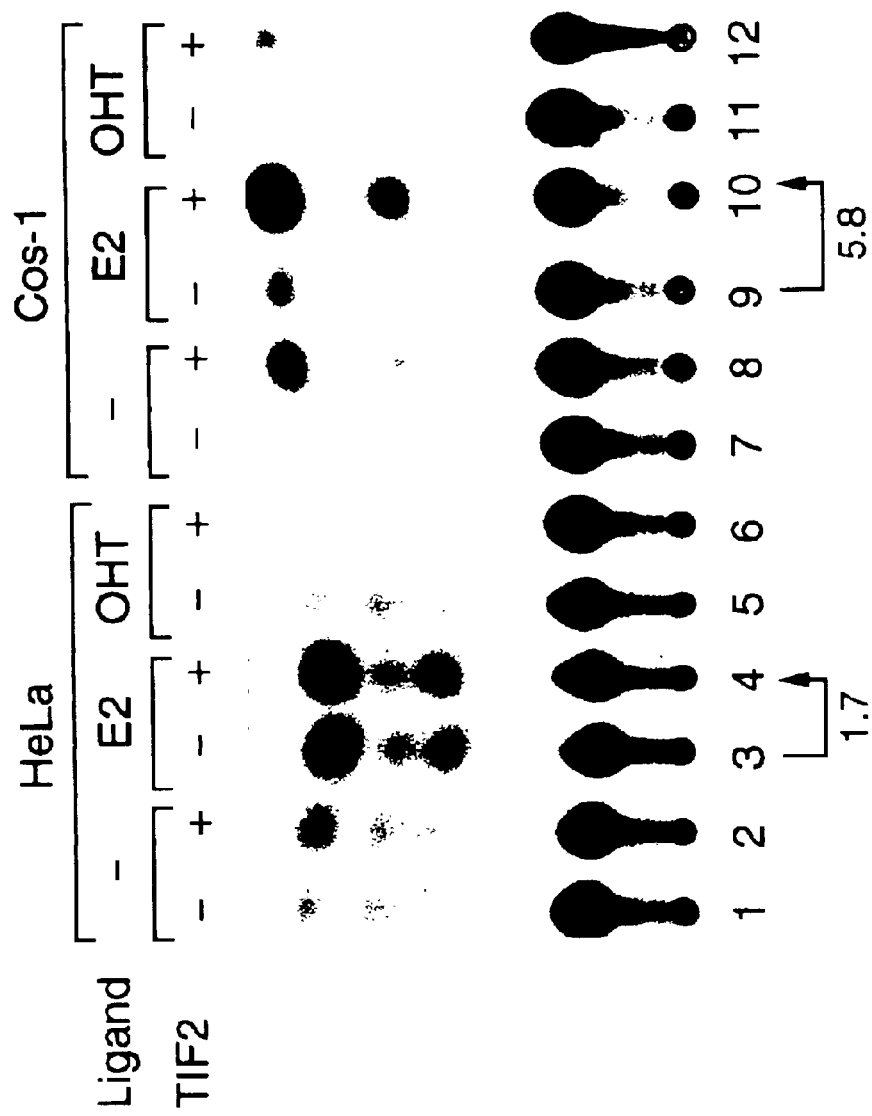

As expected, coexpression of TIF2.1 with antagonist-bound NR did not lead to any stimulation of the transactivation brought about by AF-1 in the presence of pure AF-2 antagonists (Berry, M. et al., EMBO J. 9:2811–2818 (1990); Meyer, M. E. et al., EMBO J. 9:3923–3932 (1990)), further supporting that TIF2 is AF-2-specific (FIGS. 5b and 5e for ER, OHT; FIG. 5d for PR, RU486). TIF2 expression also increased AF-2/agonist-mediated transactivation by the androgen (AR) and progesterone (PR) receptors, but not transactivation by GAL-VP16 and GAL-AP2 (FIG. 5c). Under siilar conditions, transactivation by GALRAR, GAL-RXR, GAL-VDR, GALTR and GAL-GR were unaffected by TIF2 (FIG. 5c, and not shown), suggesting that for these NRs either TIF2 is not critically involved in mediating their AF-2 activities or endogenous TIF2 amounts are sufficient to optimally support transactivation, for instance, because TIF2 has a higher affinity for these receptors. TIF2-stimulation is to some extent affected by the promoter environment of the responsive gene, as the TIF2 effect on PR/5020-induced transactivation was greater for a complex (MMTV) than for a minimal (GRE-TATA) promoter, although the latter was also reproducibly stimulated (FIG. 5d). As expected from the distinct levels of TIF2 transcripts in different tissues (FIG. 2c), the effect of TIF2 was cell type-dependent, since TIF2 had a much stronger effect on PR- and ER-induced transactivations in Cos-1 than in HeLa cells (FIGS. 5d, e).

Squelching (Meyer, M-E. et al., Cell 57:433442 (1989); Bocquel, M.-T. et al., Nucl. Acids Res. 17:2581–2595 (1989); Tasset, D. et al., Cell 62:1177–1187 (1990)) and structural studies (Bourguet, M. et al, Nature 375:377–382 (1995); Benaud, J.-P. et al., Nature 378:681–689 (1995); Wagner, R. L. et al., Nature 378:690–697 (1995); Wurtz, J.-M. et al, Nature Struct. Biol. 3:87–94 (1996)) have supported a model in which binding of the ligand to the LBD of NRs results in conformational changes generating the surface(s) required for interaction with transcriptional intermediary factors (TEFs/mediators) which transduce the AF-2 activity to the transcription machinery. Conceptually such mediators should exhibit the following properties: (i) they should bind to agonist-, but not antagonist-bound NR LBDs, (ii) their binding should be prevented by mutations abolishing AF-2 activity, (iii) they should collectively exhibit a transactivation function(s), (Iv) their expression should relieve AF-2 autosquelching, and (v) their overexpression should stimulate the activity of AF-2, whenever they are present in limiting amounts. The present study is the first report of a bonafide mediator of NR AF-2s which exhibits all these properties.

EXAMPLE 2

Production of TIF-2 Antibodies

The following TIF2 antibodies were made using known techniques, unless otherwise specified below. See, e.g., Ausubel et al, eds., CURRENT PROTOCOLS IN MOLCULAR BIOLOGY, Greene Publishing Assoc. and Wiley Interscience, N.Y., (1987–1996); Harlow and Lane ANTIBODIES: A LABORATORY MANUAL Cold Spring Harbor Laboratory (1988); and Colligan et al., eds., Current Protocols in Immunology, Greene Publishing Assoc. and Wiley Interscience, N.Y., (1992–1996), the contents of which references are incoporated entirely herein by reference.

Polyclonal Andbodies. The TIF2.1 coding sequence (amino acids 624–1287) was cloned into pETI 5b and the resulting plasmid transformed into the E. coli strain BL21 (DE3). After overexpression of the $(His)_6$-TIF2.1 protein the bacteria were lysed and the protein purified from the crude extract via affinity chromatography on a HiTrap chelating column (Pharmacia) as described (see Bourguet et al., Prot. Expr. Purif 6:604–608 (1995) for technical details). Aliquots of the purified protein (50 μg) in emulsion (Freund's Adjuvant) were injected (only once) into a New Zealand rabbit using a multisite intradermal injection protocol. Antisera obtained from serial bleeds revealed a single band of about 160 kDa on Western blots of extracts from Cos-1 cells transformed with a full length TIF2 expression vector.

Monoclonal Antibodies. A 20mer amino-acid peptide of TIF2 (with an added C-terminal cysteine) was selected on the basis of its potential immunogenic characteristics in terms of hydrophilicity, flexibility, surface probability and the 'antigenic index' according to software programmes Plot and Peptidestructure from the GCG package.

The chosen peptide corresponds to the N terminal fragment encoded by the TIF2 partial cDNA initially isolated (which encodes amino acids 624 to 1287) and corresponds to amino acids 624 to 643 of the total protein (SEQ ID NO:2):

```
    ERADGQSRLHDSKGQTKLLQ(C) (SEQ ID NO:4)
    624                 643
```

The peptide was coupled to ovalbumin via the additional cysteine using the MBS heterobifunctional crosslinker. Injections were performed in BALB/c mice intraperitonally and intravenously.

Spleen cells from the immunized mice were fuised to the Sp2/0 μg14 myeloma. Growing hybridomas were first screened by ELISA using the recombinant TIF2.1 protein and the free peptide. Positive cultures were then tested by immunocytofluorescence on Cos cells transfected with TIF2.1 (in the pSG5 vector) as well as by western blot using the transfected Cos cell extracts and HeLa nuclear extract. The positive cultures were also tested for their ability to immunoprecipitate the TIF2.1 protein from Cos transfected cells.

Cultures were cloned twice on soft agar. 0.5 hybridomas have been established, 4 secreting $IgG_1$, κ and 1 $IgG_{2a}$, κ antibodies, as shown in the Table:

| Hybridoma | ELISA | Immuno fluoresc. (Cos) | Western blot. (Cos) | Immuno precip. (Cos) |
|---|---|---|---|---|
| 1Ti-1B6 ($IgG_1$, κ) | + | + | + | + |
| 1Ti-1C9 ($IgG_1$, κ) | + | + | + | − |
| 1Ti-1D8 ($IgG_1$, κ) | + | + | ++ | + |
| 1Ti-1D12 ($IgG_1$, κ) | + | + | ++ | + |
| 1Ti-1G3 ($IgG_{2a}$, κ) | + | + | ++ | + |

EXAMPLE 3

Idendficaton of TIF2 NID

All recombinant DNA work was performed according to standard procedures (Ausubel, F. M. et al., *Current Protocols in Molecular Biology*, John Wiley & Sons, New York (1993)). GST-fiisions of nuclear receptors were expressed from the following previously described plasmids: GST (pGEX2T; Pharmacia), GST-ER (pGEX2T-hERα(DEF), also called pGEX2THE14G, amino acids 282–595), GST-RXR (pGEX2T-mRXRα(DE), amino acids 205467), and GST-RAR (pGEX2T-hRARα(DEF), amino acids 153–462) (all LeDouarin, B. et al., *EMBO J.* 14:2020–2033 (1995a)).

To further delineate the TIF2 NR interaction domain (NID), we studied the interaction between a series of TIF2 deletion mutants and the ER or RARα LBDs, using GST-fusion protein-based in vitro assays. In both cases, an NWD was mapped to the central region of TIF2 (amino acids 624–869 in mutant TIF2.5; see FIGS. 7a and b). No additional NWD could be identified in the N- or C-termini of TIF2 (FIGS. 7a and b; mutants TIF2.0, TIF2.2 and TIF2.7). Note that, in contrast, SRC-1, a paralogue of TIF2, apparently harbours two distinct non-contiguous NIDs located in the central and C-terminal regions (Onate, S. A. et al., *Science* 270:1354–1357 (1995), Yao, T. P. et al., Proc. Natl. Acad. Sci. USA 93:10626–10631 (1996); Zhu, Y. et al., *Gene Epression* 6:185–195 (1996)).

Figure 8A:
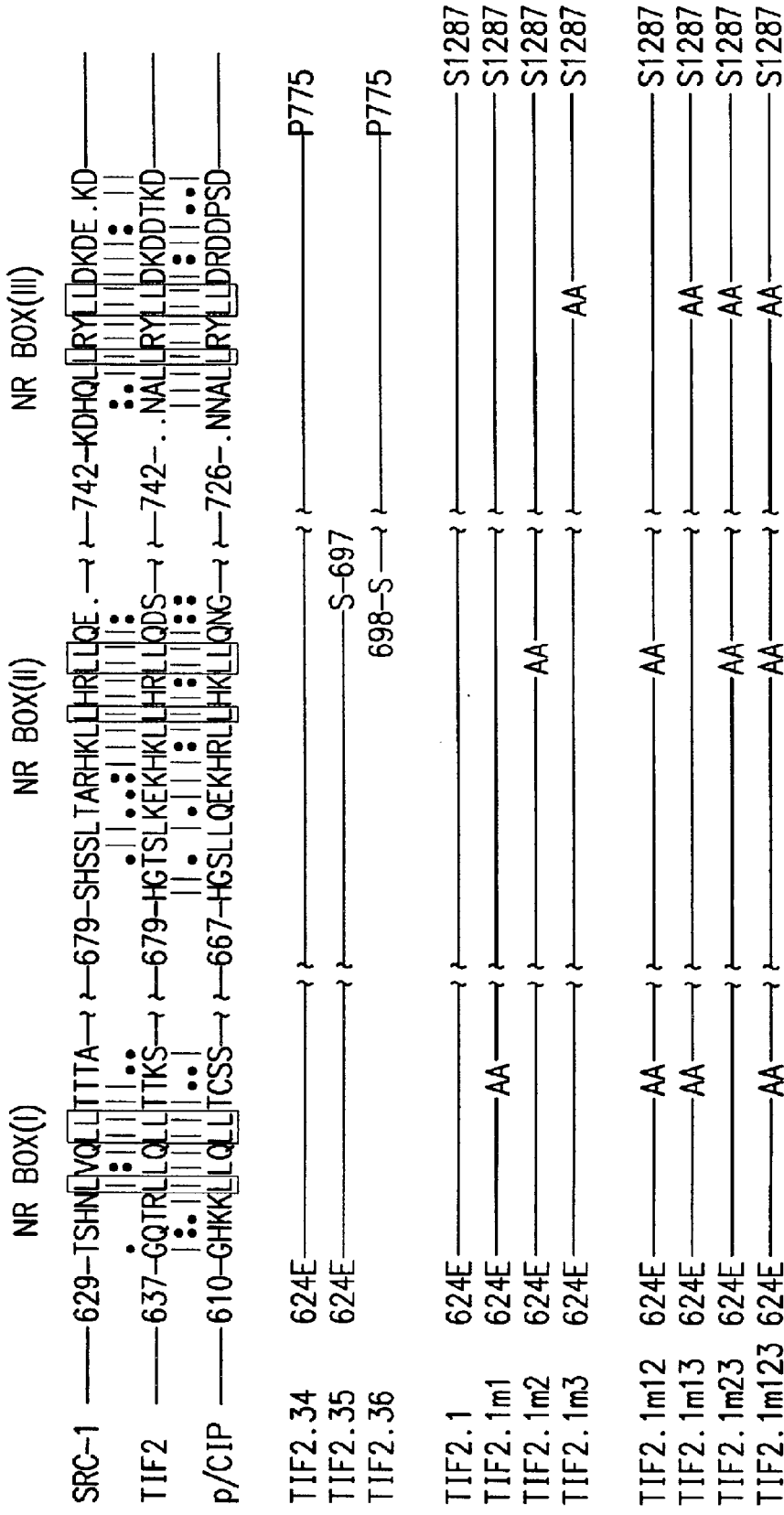
Figure 8C:
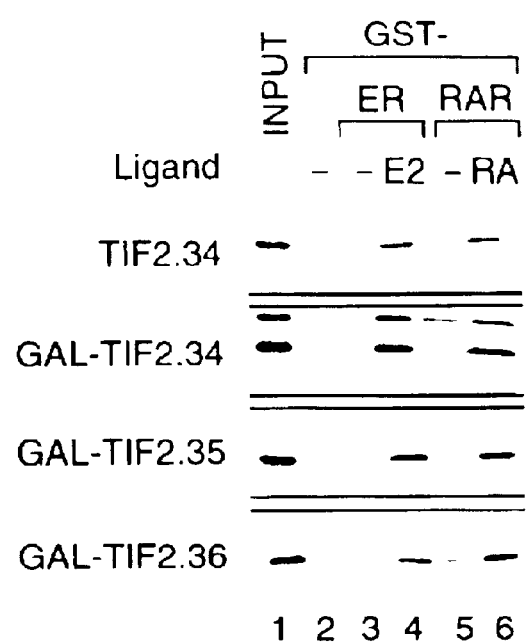

To further narrow down the TIF2 NID, TIF2.5 was C-termiinally truncated to Pro775, yielding TIF2.34 which also interacted with ER and RARα LBDs in a ligand-dependent manner (FIGS. 8a and c). Upon further truncation to Ser697, the resulting mutant still interacted with both ER and RARα LBDs but, surprisingly, a ligand-dependent interaction was also found with TIF2.36 (FIGS. 8a and c), thus indicating that the TIF2 NID is composed of at least two autonomous NO-interacting modules.

An alignment of the TIF2 NID amino acid sequence present in TIF2.34 with the corresponding region of SRC-1 (Onate, S. A. et al., *Science* 270:1354–1357 (1995)) revealed three highly conserved regions (FIG. 8a). Interestingly, all three contain the motif LxxLL (SEQ ID NO:12)(FIG. 8b), originally identified in the so-called "nuclear receptor box" (NR box) of TIF1α as the LxxLLL (SEQ ID NO:13) motif, which was also present in RIP140 (Cavaillès, V. et al., *EMBO J.* 14:3741–3751 (1995)) and TRIP3 (Lee, J. W. et al.,(1995)) (see LeDouarin, B. et al., *EMBO J* 15:6701–6715 (1996) and FIG. 8b). Importantly, 10-amino-acid sequences comprising the TIF1α or RP140 NR boxes were sufficient for functional interaction with RXR in a ligand- and AF-2 AD-integrity-dependent manner, and mutation of the leucines at position 4 and 5 (LL→AA) of the TIF1α LxxLLL (SEQ ID NO:13) motif abrogated TIFα-RXR interaction (LeDouarin, B. et al., *EMBO J.* 15:6701–6715 (1996)). The functionality of the RIP 140 NR box was recently confirmed (Heery, D. M. et al., *Nature* 387:733–736 (1997)).

Figure 8D:
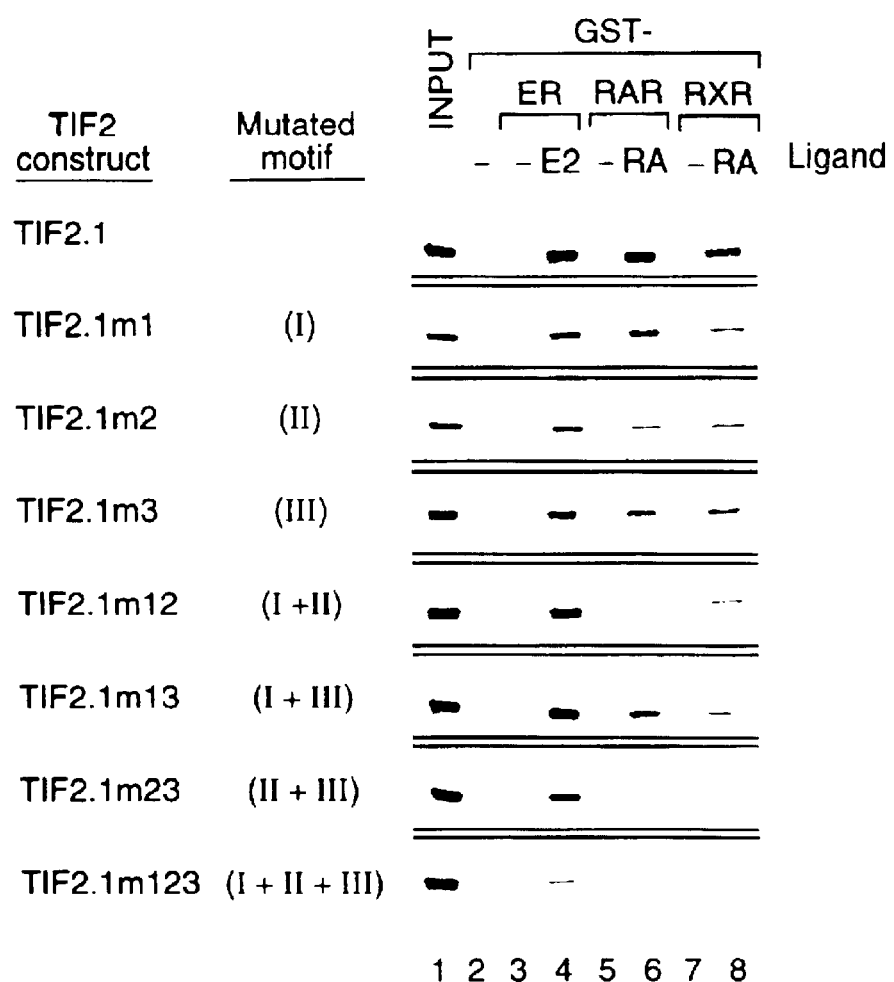
Figure 8E:
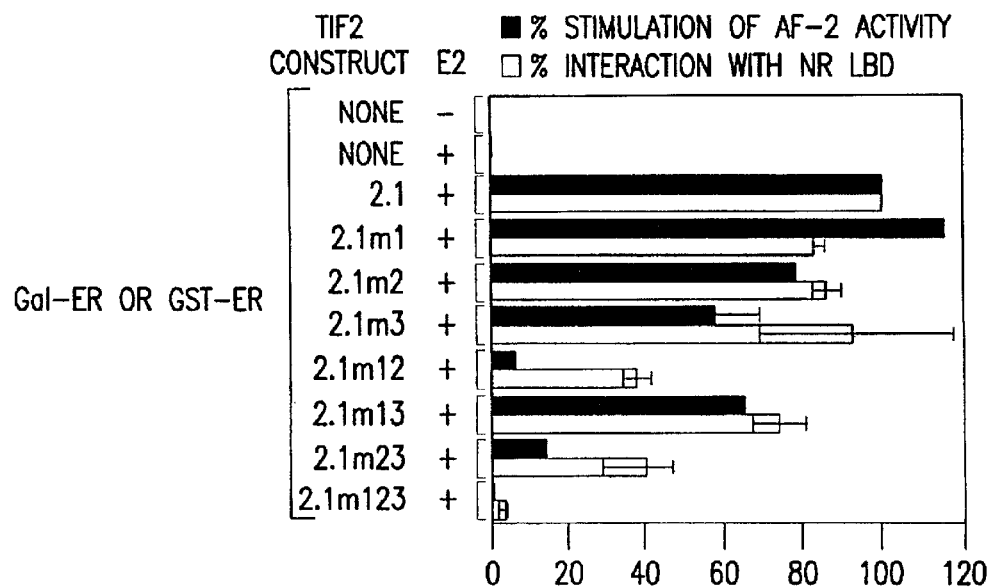
Figure 8F:
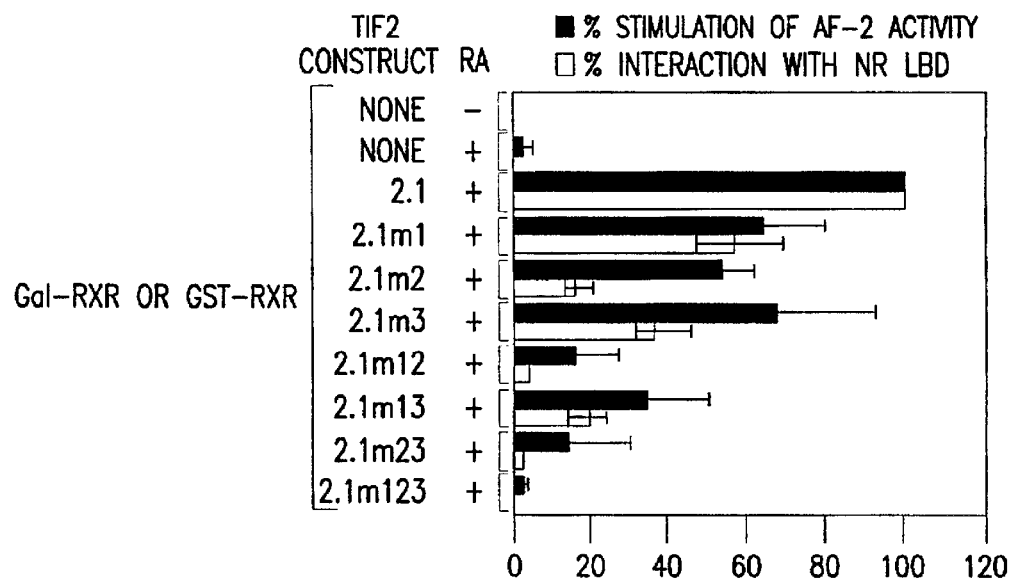

To investigate the functional significance of these three motifs in the TIF2 NID, the above LL→AA mutation was introduced in TIF2.1, either into each motif alone or in all possible combinations of the three motifs (TIF2.1 ml to m123 in FIG. 8a, numbers following "m" refer to the mutated motifs). Mutation of all three MR boxes was required to abrogate both the binding to ER, RARα and RXRα (FIG. 8d, quantitation in FIG. 5e, white bars) and TIF2-dependent stimulation of ligand-induced transactivation by ER and RXRα AF-2s (FIG. 8e, black bars, and data not shown; in the case of RARα AF-2 the stimulation was weak and was not quantified). TIF2.1 constructs in which two NR box motifs were mutated still exhibited ER binding and stimulation of AF-2 activity, in particular when the NR box motif II was intact, suggesting that the three NR box-containing modules are at least in part, functionally redundant (FIGS. 8d and e; TIF2.1 m12, m13, and m23). This redundancy was obvious when only one NR box motif was mutated; in contrast to TIF1α, which contains only one NR box (LeDouarin, B. et al., *EMBO J.* 15:6701–6715 (1996)), mutation of a single TIF2 NR box did not abrogate ER binding and stimulation of ER AF-2 activity. All three mutants (TIF2.1 m1 to m3) bound to ER and stimulated estradiol-dependent transactivation by the ER with similar efficiency as TIF2.1 itself (FIGS. 8d and e). In the case of RARα and RXRα the mutations had, in general, a more deleterious effect on receptor LBD binding and stimulation of AF-2 activity than in the case of ER (FIGS. 5d and e). This may possibly reflect a weaker interaction between TIF2 and either RARα or RXRα than with ER. However, in spite of exhibiting in general a lower activity, the patterns of NR binding and stimulation of AF-2 activity of the NR box mutants were similar for ER and RARα and RXRα, as mutation of motif II was always more detrimental in double mutants than mutation of motifs I and III (see FIG. 8e).

Importantly, for both ER and RXRα there was a good correlation between the effect of any of the various mutations on TIF2.1-receptor binding in vitro and TIF2.1-mediated stimulation of AF-2 activity (FIG. 8e), supporting a mechanism whereby the stimulation of AF-2 activity by TIF2 involves TIF2-NO interaction through NR holo-LBD-TIF2 NR box interface(s).

Our present structure-function analysis reveals that TIF2 contains a single nuclear receptor-interaction domain (ND). Note in contrast to the other TIF2 family member, SRC-1, which was reported to contain two NIDs (Oñate, S. A et al., Science 270:1354–1357 (1995); Yao, T. P. et al., Proc. Natl. Acad. Sci. USA 93:10626–10631 (1996); Zhu, Y. et al., Gene Expression 6:185–195 (1996)). Note, however, that one of the two SRC-1 NID is most probably homologous to the TIF2 ND characterized here (see FIG. 8a). The TIF-2 NID is composed of three modules, and each can bind independently in a ligand-dependent manner to the NRs tested in this study. Interestingly, these modules contain the NR box motif LxxLL (SEQ ID NO:12), which was originally recorded (as the motif LxxLL (SEQ ID NO:13), FIG. Bb) within a 10 amino acid NR binding module of TIF1α which was found to be conserved in the NID of RIP140 and also present in TRIP3 (LeDouarin, B. et al., EMBO J. 15:6701–6715 (1996) and refs therein). Moreover, the TIF1α and RIP140 modules were shown to functionally interact with NRs (LeDouarin, B. et al, EMBO J. 15:670116715 (1996)). The implication of NR box motifs in NO-coactivator binding and their presence in a number of different coactivators was pointed out in recent reports (Heery, D. M. et al., Nature 387:733–736 (1997); Torchia, J. et al., Nature 387:677–684 (1987); LeDouarin, B. et al., EMBO J. 15:6701–6715 (1996)). Note that all three TIF2 NR box motifs described here are conserved in the recently discovered TIF2 paralogue p/CIP (Torchia, J. et al., Nature 387:677–684 (1987)). In contrast to TIF1α, for which mutation of leucines at positions 4 and 5 to alanine of its single NR box motif (LL→AA) abrogates NR binding, mutation of all three motifs are required in the TIF2 NID to abrogate NR binding, indicating that each of these motifs can contribute to a TIF2 surface that interacts with a cognate surface of NR holo-LBDs. That the NR boxes of TIF2 exhibit functional redundancy is supported by the observation that the LL→AA mutation in any of the three TIF2 NID motifs apparently did not (in the case of the ER) or only weakly (in the case of RARα, RXRα) reduce the efficiency of NR interaction. Moreover, in the TIF2.1 environment, any single intact NR box motif on its own (i.e., when the two other motifs were mutated) was sufficient for interaction with the holo-ER LBD, although only motif II on its own could bring about a nearly wild-type NR binding efficiency. In contrast, for RARα and RXRα interaction, mutants with single intact NR boxes were 5 (box II) to 20 (box I or III) times less efficient than the wild-type TIF2 containing the three NR boxes. Crystallography studies will be necessary to distinguish between two possible models, in which the three NR box motifs (i) contribute to the formation of a tripartite NID surface that specifically recognizes a cognate holo-NO LBD surface, or (ii) belongs to independent surfaces which each can interact, albeit with different efficiencies, with the same holo-NO surface. Note, however, that the second model could allow TIF2 to interact cooperatively with both partners of NR homo- or heterodimers, thus rendering transactivation by NRs sensitive to small variations in TIF2 levels. Note also that, for both ER and RXRα, the effects of NR box mutations on NR binding and stimulation of TIF-2 activity were correlated, further supporting the conclusion that the transcriptional effect of TIF2 involves the formation of a NR box-NO LBD interaction interface.

The motif LxxLL (SEQ ID NO:12) has been found in a number of other NR coactivators (see above), thus suggesting some similarity in the mode of NO-coactivator interactions. However, this does not exclude NO-specific modulation of these interactions, as the NR box surrounding sequences are highly variable. In this respect, note also that TIF2 NR boxes II and III are predicted to form α-helices, while NR box I is predicted to fold into a β-sheet structure (structure predictions according to SOPMA; Geourion and Deleage, 1994).

EXAMPLE 4

Identification of the AD1 and AD2 Activation Domains of TIF2

Figure 7A:
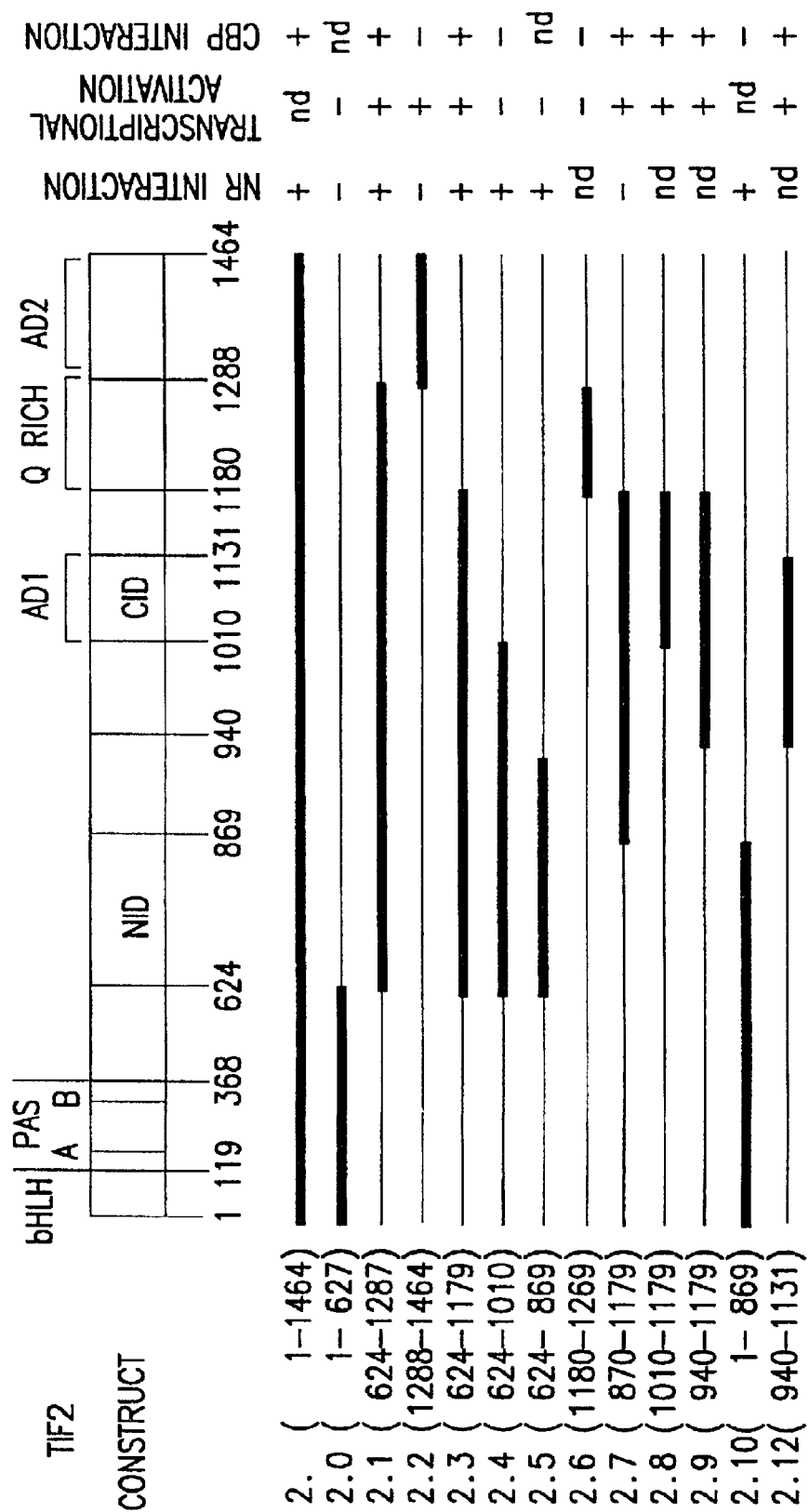
Figure 7B:
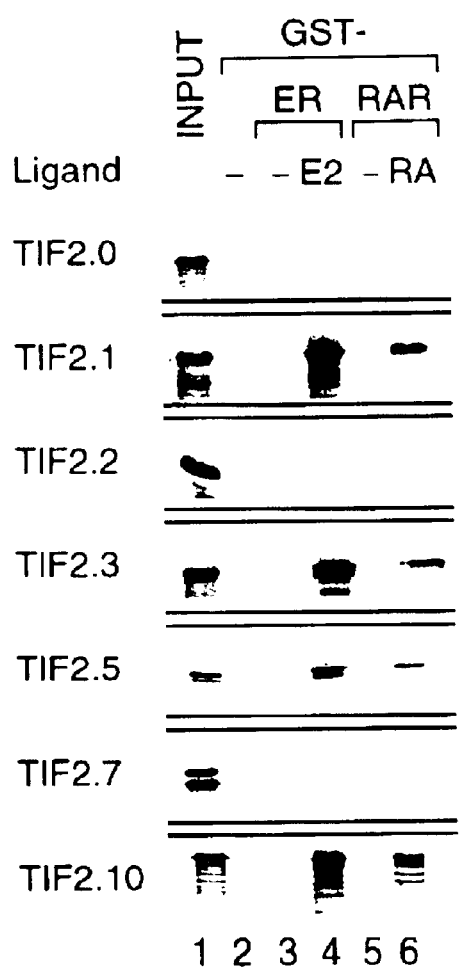

Transient transfection assays with a GAL4 reporter plasmid and chimeras containing various TIF2 fragments linked to the GAL4 DNA binding domain (DBD) demonstrated the presence of two autonomous transcriptional activation domains in the C-terminal 460 amino acids of TIF2, termed AD1 and AD2 (delineated by mutants TEF2.8, TIF2.12 and TIF2.2 in FIGS. 7a and c). Transient transfections of HeLa and Cos-1 cells were performed as described (Gronemeyer et al., (1987); Bocquel, M. T. et al., Nucl. Acids Res. 17:2581–2595 (1989)).

The N-terminal AD1 (amino acids 1010–1131), which is present in TIF2.1, showed a stronger activity than the C-terminal AD2 (amino acids 1288–1464) (compare TIF2.8 and TIF2.12 with TIF2.2 in FIGS. 7a and c). Note, however, that the weaker activity of AD2 (relative to AD1) could be due to a lower expression level of the GAL-TIF2.2 fusion protein (compare with GAL-TIF2.8 and GAL-TIF2.12 in FIG. 7c). Both TIF2 activation functions were active in Cos-1 and HeLa cells (FIG. 7c). Notably, the minimal AD1 (TIF2.8) and AD2 (TIF2.2) constructs exhibited some cell-specific activities, as GALTIF2.8 was more active in HeLa than in Cos cells, whereas the opposite was observed for GAL-TIF2.2 (FIG. 7c). Interestingly, the glutamine-rich region of TEF2 could neither activate transcription on its own when fused to the GAL4 DBD (FIGS. 7a and c; mutant TIF2.6), nor was it required for transcriptional activation by AD1 or AD2. No activation function could be detected in the N-termiinal part of TIF2 (see FIGS. 7a and c; mutant TIF2.0).

We conclude from these data that the nuclear receptor interacting domain (NID) and the two transcriptional activation functions of TIF2 correspond to distinct modular domains, since TIF2.5 can bind to NRs, but cannot activate transcription, whereas TIF2.2 and TIF2.8 cannot bind NRs but are able to activate transcription (FIG. 7a).

EXAMPLE 5

Characterization of the TIF2 AD1 and AD2 Activation Domains

Figure 7D:
Figure 7E:
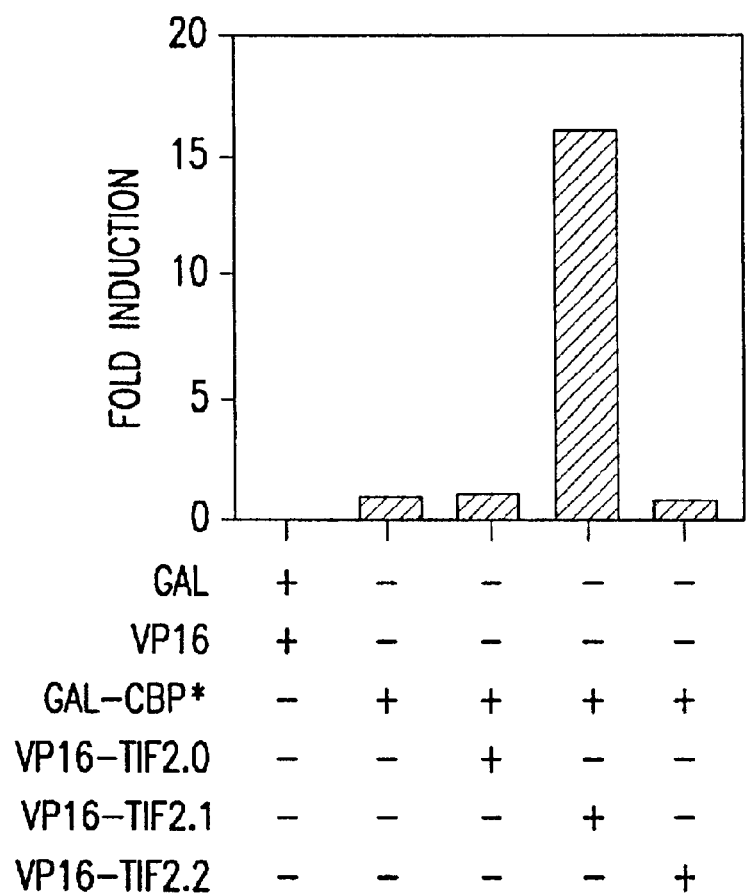

Recently CBP and p300, originally identified as coactivators of the transcription factor CREB, were shown to act as general integrators of multiple signaling pathways, including activation via agonist-bound RARα and TR (for reviews and refs see Eckner, R., Biol. Chem. 377:685–688 (1996); Janknecht & Hunter,(1996); Glass, C. K. et al., Current Opin. Cell Biol. 9:222–232 (1997); Shikama, N. et al., Trends in Cell Biol. 7:230–236 (1997)). Furthermore, it was reported that SRC-1, which belongs to the same gene family as TIF2, interacts with CBP and p300 (Kamei, Y. et al., *Cell* 85:403–414 (1996); Yao, T. P. et al., *Proc. Natl. Acad. Sci. USA* 93:10626–10631 (1996); Hanstein, B., et al., *Proc. Natl. Acad Sci USA* 93:11540–11545 (1996)). Using GST-fusion protein-based interaction and animal cell-based two hybrid assays, we therefore analyzed whether TIF2 could also interact with CBP. In the two hybrid system only the central TTF2.1 fragment, but not the N-terminal TIF2.0 or the C-terminal TIF2.2 fragments (FIG. 7a), scored positive for interaction with GAL-CBP (containing amino acids 1872–2165 of CBP, which encompass the SRC-1 interacting domain of CBP; FIG. 7e). A GST-CBP fusion protein was expressed in *E. coli* and used for puU-down assays with in vitro translated TIF2 polypeptides (FIG. 7d). TIF2 did interact with CBP and, interestingly, the CBP-interacting domain (CID) apparently overlapped the AD1 activation domain of TIF2 (compare FIGS. 7a, c and d; mutants TIF2.8 and TIF2.12). The interaction of TIF2 with CBP was direct, as a purified *E. coli*-expressed TIF2.1 protein also interacted with GST-CBP (data not shown). Only this region of TIF2 interacted sign ficantly with the GST CBP fusion protein, thus suggesting that the TIF2 AD1 activity may originate from the recruitment of CBP. Purger N-terminal regions (FIGS. 7a and d; mutants TIF2.10 and TIF2.4) or the C-terminal AD2 activation domain (FIGS. 7a and d; mutant TIF2.2) did not show any binding to GST-CBP. Note that TIF2.2 also did not interact win fuli-length CBP (data not shown), suggesting that the activity of TIF2 AD is mediated by (a) factor(s) distinct from CBP.

Figure 9A:
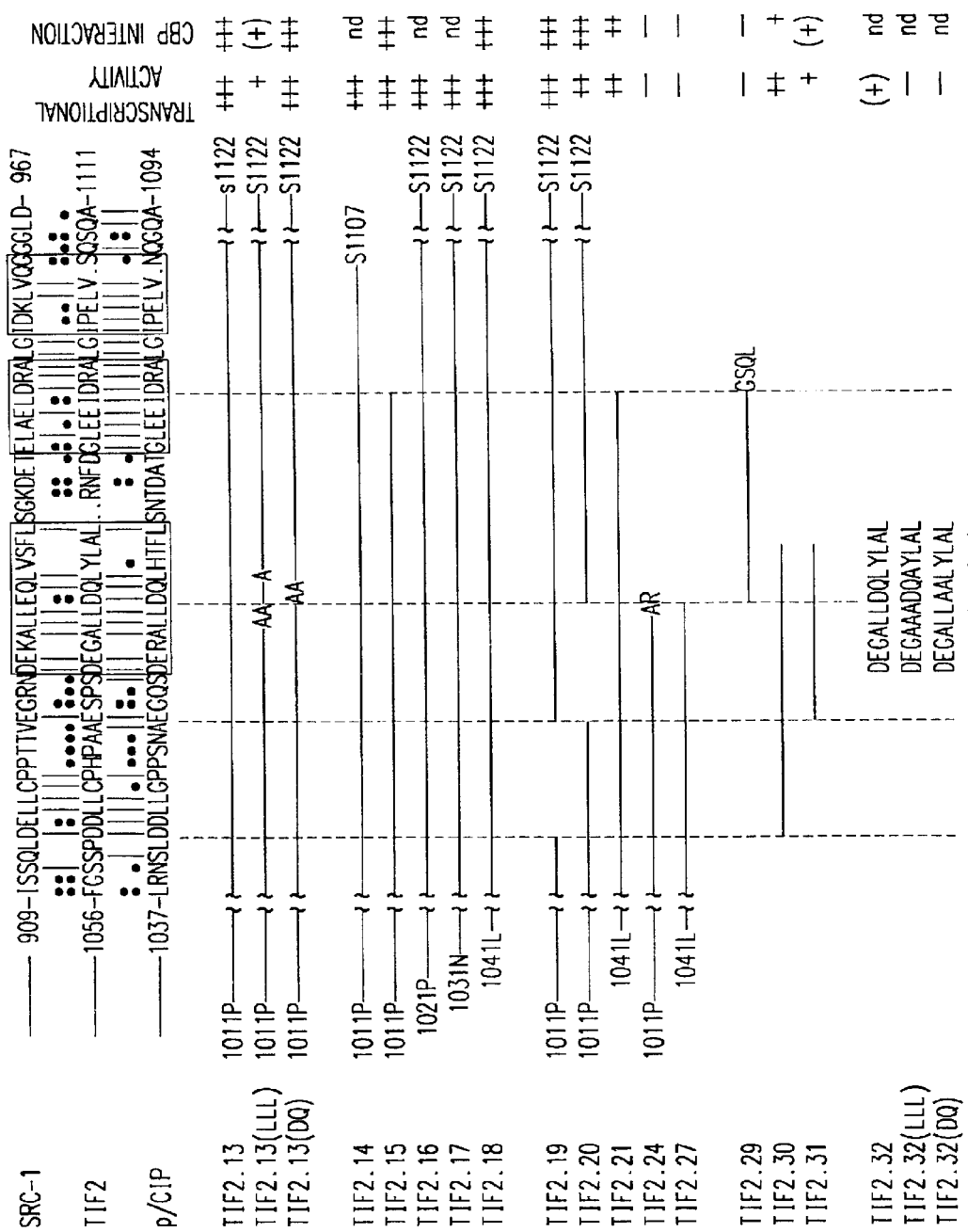
Figure 9C:
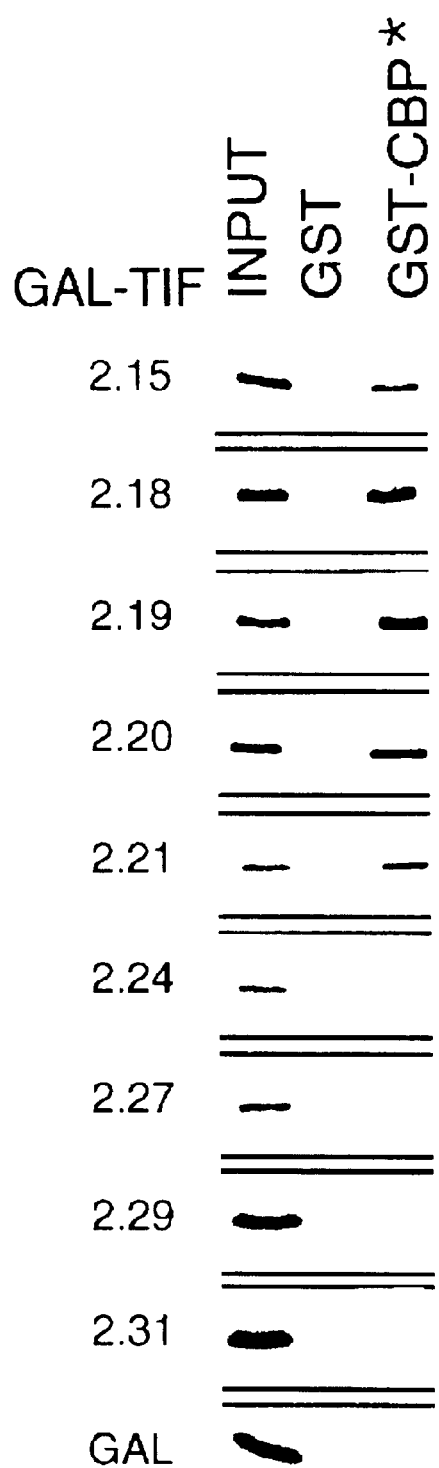
Figure 10B:
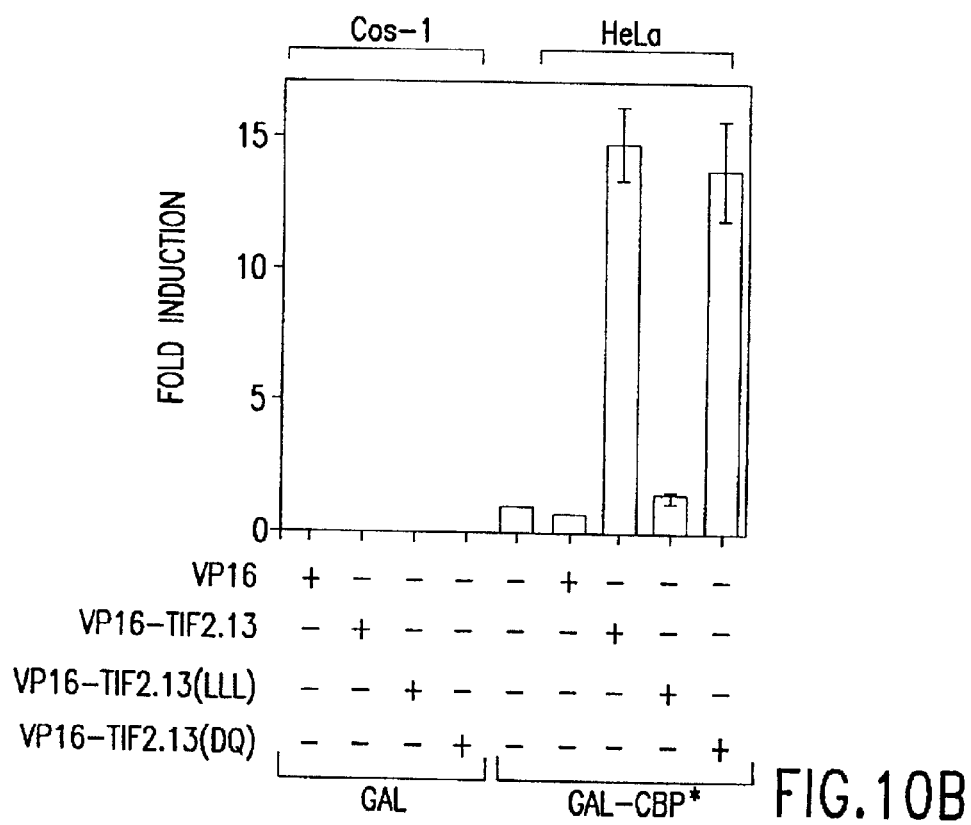
Figure 10C:

To investigate whether the CID of TIF2 could be separated from the AD1 activation domain, the ability of a series of GAL-TIF2 truncation mutants to activate a GAL4-reporter was compared with their ability to interact with the GST-CBP protein in vitro (FIG. 9). TIF2.13 (which encompasses $Pro_{1011}$ to $Ser_{1122}$ exhibited a potent transcriptional activity, comparable to that of larger TIF2 fragments (compare FIGS. 7 and 9). Removal of 26 C-terminal (TIF2.15) or 20 N-terminal (TIF2.18) amino acid residues reduced transcriptional activity only weakly (FIGS. 9a and b). Note that TIF2.13 also interacted with CBP in vivo, as shown by using a two hybrid assay in transfected mammalian cells (FIG. 10b).

While the internal deletion of residues $Asp_{1061}$ to $Ala_{1070}$ (TIF2.19) had only a minor effect on the ability of TIF2.13 to transactivate, deletion of the $Glu_{1071}$ to $Leu_{1080}$ segment (mutant TIF2.20) significantly reduced TIF2 AD1 transcriptional activity. Notably, these residues belong to a sequence predicted to fold into an amphipathic α-helical structure which is highly conserved between TIF2 and SRC-1 (FIG. 9a). The involvement of this region in transactivation was confirmed by analysis of mutants TIF2.21 to TIF2.32 (FIGS. 9a and b). All constructs containing the TIF2 wild-type sequence from $Asp_{1075}$ to $Leu_{1087}$ stimulated transcription, whereas even a deletion of only some of these residues significantly reduced transcriptional activation. However, on its own this α-helical peptide transactivated very poorly, and had to be incorporated into additional upstream and/or downstream TIF2 sequences to generate significant transcriptional activity (FIGS. 9a and b; compare mutants TIF2.13, TIF2.21 and TIF2.32). Importantly, in all cases ADD activity coincided with CBP interaction, since transcriptionally inactive constructs did not interact with CBP (TIF2.24, TIF2.27 and TIF2.29 in FIGS. 9a–c), while transcriptionally active mutants also bound CBP. Moreover, the strength of the in vitro interaction with GST-CBP apparently correlated with transactivation efficiency (FIGS. 9a–c; e.g., compare TIF2.21 and TIF2.31).

To investigate whether the integrity of the putative amphipathic α-helical region is required for both AD1 transcriptional activity and interaction with CBP, we introduced point mutations into TIF2.13; the three conserved hydrophobic Leu or the hydrophilic Asp-Glu residues were converted to alanines [FIG. 9a; TIF2.13(LLL) and TIF2.13(DQ)]. Interestingly, mutation of the three leucine residues almost completely abolished AD1 activity, whereas mutation of the Asp-Glu sequence had very little, if any effect (FIG. 10a). Again, AD1 activity and interaction with CBP in vitro FIG. 10c), as well as in vivo (FIG. 10b), were strictly correlated, since GAL-TIF2.13(DQ), which transactivated as efficiently as wild type GAL-TIF2.13, interacted strongly with CBP, whereas the transcriptionally inactive GAL-TIF2.13(LLL) interacted very weakly with CBP. Together these results indicate that (i) CBP mediates the AD1 activity of TIF2, (ii) a putative amphipathic α-helix motif located within the AD1 domain is critically involved in, but not sufficient for, efficient CBP binding/transactivation and (ii) the amphiphilicity of this motif is not required for AD1 activity and CBP binding.

The two TIF2 activation functions AD1 and AD2 apparently operate through different transcriptional activation cascades. While the TIF2 AD1 activation domain could not be separated by mutational analysis from the TIF2 domain which interacts in vitro and in vivo with a region of the CBP surface which also mediates SRC-1 binding (Kamei, Y. et al., *Cell* 85:403–414 (1996)), neither this region, nor full length CBP, interacted with TIF2 AD2. That the two TIF2 activation functions may operate through distinct pathways is also suggested by the differential cell specificity of the minimal fragments exhibiting AD1 activity (e.g., TIF2.8, TIF2.7, TIF2.9, TIF2.12) and AD2 activity (TIF2.2). While TEF2.2 is more active in Cos-1 than in HeLa cells, all of the minimal fragments containing AD1 are more active in HeLa cells. Along the same lines, removal in TIF2.3 of sequences N-terminal of TIF2.8 resulted in a 10-fold and 2-fold increased transactivation in Hela and Cos-1 cells, respectively, and removal in TEF2.1 of sequences C-terminal of TIF2.3 gave a 9-fold and 3-fold higher transactivation in Hela and Cos-1 cells, respectively. This suggests that the deleted sequences could C) exert either intra- or intermolecular repression on TIF2 AD1 activity/CBP interaction. In addition, the coactivator activity of TIF2 may be cell-specifically modulated by the differential efficiency of its two ADs and factors interacting with the sequences N- and C-terminally of the AD1 activation function.

It is worth noting that the core of AD1 (TEF2.32) on its own is a very poor transactivator and CBP binder, and requires additional surrounding sequences to generate a fully active (i.e., efficient CPB binding) surface. However, mutational analysis of the AD1 core in the context of a strong activator fragment (TEF2.13) reveals the critical importance for transactivation and CBP binding in vivo and in vitro of three leucine residues (FIG. 10). These leucines belong to a conserved LLxxLoxxL (SEQ ID NO:14) motif in all three members of the TIF2 coactivator family (FIG. 9a; Torchia, J. et al, *Nature* 387:677684 (1987)) which is distinct from the LxxLL (SEQ ID NO:12) NR box motif Notably, although these leucines are embedded in a predicted amphipathic α-helix, the amphiphilicity is not required for function, since a mutation of the hydrophilic residues (compare TIF2.13 with TIF2.13 (DQ)) does not affect transactivation/CBP binding.

TIF2 can apparently fulfill at least two mediator functions, (i) as a "bridging factor" between the AF-2 function of nuclear receptors and CBP via its AD1 activation domain and (ii) as a transcriptional mediator through as yet unknown CBP binding-independent route(s) via its AD2 function. Presently, we have no evidence that TIF2 could possess an intrinsic enzymatic activity; none of the bacterially-expressed purified TIF2 fragments, in particular TIF2.1 which was shown to be fully competent in NR and CBP interactions in vitro, exhibited any histone acetylase activity under conditions where bacterially-expressed purified yeast GCN5 was highly active (our unpublished results).

EXAMPLE 6

TIF2 Enhancement of NR AF-2 Activity

The observation that animal transcriptional activators, such as the human ER (Metzger, D. et al., Nature 334:31–36 (1988)), are also active in the yeast Saccharomyces cerevisiae demonstrated that the basic principles of transcriptional enhancement have been conserved from yeast to man. We therefore investigated whether TIF2 could enhance transcriptional activation by various NR constructs expressed in S. cerevisiae. Both, NRs and TIF2.1 were expressed from multicopy plasmids in the yeast strain PL3 (a), which contains a URA3 reporter gene under the control of three estrogen response elements ((ERE)$_3$-URA3; Pierrat, B. et al., Gene 119:237–245 (1992)).

In yeast, the hERa constructs were expressed from the following YEp90-based plasmids: HEGO (hERα, YEp90-HEGO, amino acids 1–595), HE15 (YEp90-HE15, amino acids 1–282), and HEG19 (YEp90-HEG19, amino acids 179–595) (all Pierrat, B. et al., Gene 119:237–245 (1992)), HE179-338 (YEp90-HE179-338; Pierrat, B. et al., Gene 143:193–200 (1994)). From the yeast multicopy plasmid pBLI (LeDouarin, B. et al., Nucleic Acids Res. 23:876–878 (1995b)), which codes for ER(F)-epitope-tagged ER(C)-fusions, the following plasmids were expressed: ER(C)-RAR(DEF) (pBL1-hRARα(DEF), amino acids 154–462) and ER(C)-RXR(DE) (pBL1-mRXRα(DE), amino acids 205–467) (both vom Baur, E. et al., EMBO J. 15:110–124 (1996)). TIF2 was expressed in yeast from the multicopy plasmid pAS3 (gift from B.LeDouann), which is a derivative of YEp90 containing the LEM2 marker. Yeast PL3(a) (Pierrat, B. et al, Gene 119:237–245 (1992)) transformants were grown exponentially in the presence or absence of ligand for about five generations in selective medium containing uracil. Yeast extracts were prepared and assayed for OMP decase activity as described previously (Pierrat, B. et al., Gene 119:237–245 (1992)).

As expected from previous studies (Metzger, Nucl. Acids Res. (1992); Pierrat, B. et al, Gene 119:237–245 (1992); Pierrat, B. et al., Gene 143:193–200 wilL (1994)) the full length ER (HEGO) induced orotidine 5'-monophosphate decarboxylase (OMP Decase) activity in a ligand-dependent manner (FIG. 11, lanes 1 and 3). Interestingly, the transcriptional activity of ER was further enhanced by coexpression of the TIF2.1 fragment (FIG. 11, compare lanes 3 and 4). In the absence of hormone, TIF2.1 had no significant effect on ER-induced transcriptional activation (FIG. 11, compare lanes 1 and 2). Essentially the same results were observed for HBEG 9 which is devoid of the N-terminal region A/B, indicating that TIF2 exerts its effect on the ligand-dependent ER AF-2 (FIG. 11, lanes 5–8). In contrast, neither the AF-1 activity of HE15, (which encompasses the ER regions A, B and C; Kumar & Chambon, Cell 55:145–156 (1988)), nor the AF-2a activity of the HE179-338 construct (Pierrat, B. et al., Gene 143:193–200 (1994)) were stimulated by coexpressing TIF2.1 (FIG. 11, lanes 9–12). This is in agreement with the results obtained in mammalian cells, and with the observation that an intact LBD is required for TIF2.1 to interact with the ER (Voegel, J. J. et al., EMBO J. 15:3667–3675 (1996)).

TIF2.1 also stimulated the AF-2 activity of the liganded RXRα(DEF) region in yeast (FIG. 11, compare lanes 19 and 20). This enhancement was ligand-dependent; no activation via the RXRα(DEF) region was observed when the ER(C) RXRα(DEF) chimera was coexpressed with TIF2.1 in the absence of ligand (FIG. 11, compare lanes 18 and 20). Again these observations parallel those made in HeLa and Cos-1 cells (see FIG. 12c).

Surprisingly, even in the absence of ligand, and in contrast with the observations made with ER and RXRα, TIF2.1 very efficiently enhanced transactivation by the RARα LBD (FIG. 11, lanes 13 and 14). The addition of retinoic acid further increased this transcriptional activation (FIG. 11, lanes 14 and 16). Note that, as previously reported (Heery, D. M. et al., Nature 387:733–736 (1997)), both RARα and RXRα AF-2 on their own poorly activated transcription from the URA3 reporter.

The enhancement of AF-2 activity which was particularly strong in yeast cells, has also been recently observed for GRIP 1, the mouse homologue of TIF2 (Hong, H. et al., Mol. Cell. Biol. 17:2735–2744 (1997)). These observations suggest that yeast cells contain coactivators which only poorly mimic the action of the mammalian NR coactivators. As yeast cells apparently do not contain a CBP homologue, it will be interesting to investigate which yeast factor mediates the activity of TIF2. Note in this respect that GAL-TIF2.1 is a strong transactivator in yeast (our unpublished results).

Interestingly, the expression of TIF2 in yeast led to a marked stimulation of transactivation by the unliganded ER(C)-RARα(DEF), which was not observed with ER or RXRα unliganded LBDs. Structural studies have revealed that binding of the ligand results in a conformational change of the LBD, which generates the surface(s) for coactivator binding (Renaud, J. P. et al., Nature 378:681689 (1995)). Our present result, therefore, suggests that a high level of coactivators might in the absence of ligand drive the LBD of some receptors into a holo-LBD-like conformation, thus giving rise to ligand-independent transcriptional activity. By analogy, one could speculate that high levels of corepressors could "lock" NR LBDs in the apo-LBD conformation. It would therefore be interesting to investigate whether levels of coregulators might lead to constitutive activity (even in the presence of antagonists) or conversely to lack of inducibility of nuclear receptors in some pathological states.

EXAMPLE 7

TIF2 NID Inhibition of NR AF-2 Activity

Figures 12A, 12B:
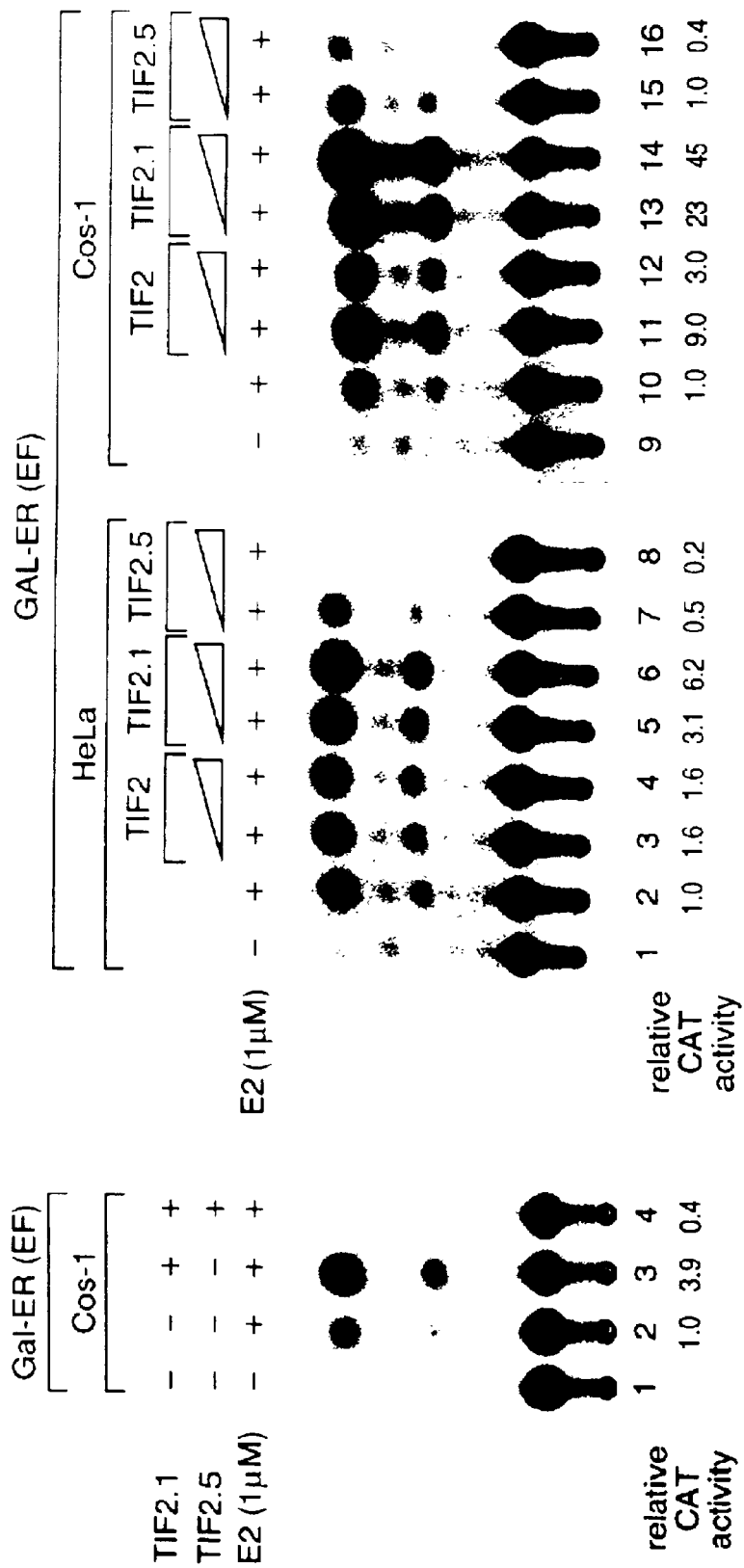

Overexpression of the TIF2.1 fragment, which contains both the NM and AD1 activation function, stimulates the ER AF-2. activity of the ER LBD transiently in Cos-1 cells (FIG. 12a, lanes 2 and 3; Voegel, JJ. et al., EMBO J. 15:3667–3675 (1996)). That this stimulation was due to a direct interaction between the ER LBD and the ND of TIf2, was strongly suggested by the observation that overexpression of the TIF2.5 mutant which contains the isolated NID, but lacks AD1 (see FIG. 7a) prevented the stimulatory effect of TIF2.1 (FIG. 12a, compare lanes 3 and 4). Note that in the absence of TIF2.1, TIF2.5 overexpression also decreased the transactivation by the ER AF-2 which was presumably mediated through Cos-1 endogenous coactivators (FIG. 12a, compare lane 4 with lane 2), thus suggesting that these Cos-1 mediators either correspond to endogenous TIF2s, or interact with the ER holo-LBD through surfaces which are identical to, or in direct vicinity of, the TIF2 ND) interaction surface.

Figure 12C:
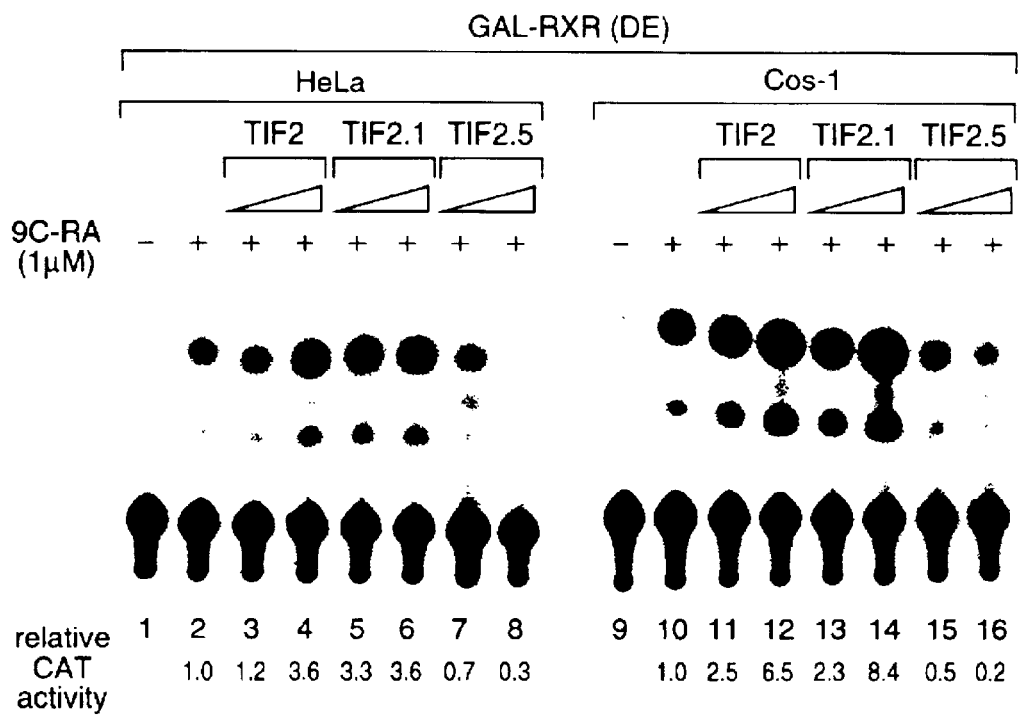
Figure 12D:
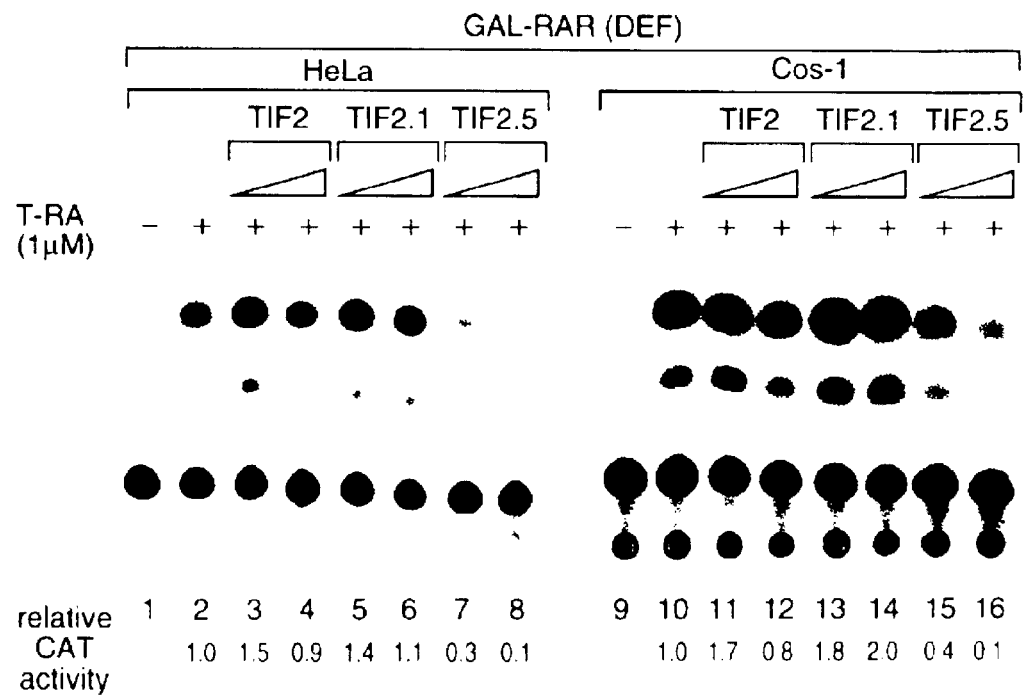

We previously reported an agonist-dependent interaction of TIF2 with RAR and RXR LBDs, which was dependent on the integrity of the NR AF-2 AD core, but failed to observe a stimulatory effect of TIF2 on the transcription activation of a $(17m)_5$-Globin-promoter-CAT reporter by GAL-RAR LBD or GAL-RXR LBD fusion proteins (Voegel, J. J. et al., EMBO J. 15:3667–3675 (1996)). Since this failure was likely to be due to the presence of sufficient amounts of endogenous mediators for achieving maximal transactivation from this reporter gene, we modified the transfection conditions and used a reporter construct bearing a minimal promoter. A clear TIF2 and TIF2.1 stimulatory activity for RXRα AF2 was observed in HeLa and Cos-1 cells when using the $(17m)_5$-TATA-CAT reporter (FIG. 12c, compare lanes 3–6 and 11–14). This stimulatory effect was less marked with RARα AF-2 and could be observed reproducibly only with the TIF2.1 fragment in Cos-1 cells (FIG. 12d, compare lane 10 with lanes 13 and 14; note that TIF2.1 is expressed at >10 fold higher levels than TIF2; data not shown). The reporter plasmids $(17m)_5$-TATA-CAT (May, M. et al., EMBO J. 15:3093–3104 (1996)) and 17M5-G/CAT $((17m)_5$-β-globin-CAT; Durand, B. et al., EMBO J. 13:5370–5382 (1994)) each contain five copies of the GAL4 response element in front of a simple TATA motif or of the β-globin promoter, respectively, upstream from the CAT reporter gene.

Assuming that TIF2 or coactivators recognizing the TIF2 interacting surface on NR LBDs, generally mediate the AF-2 function of NRs, the NID containing TIF2.5 should exert its dominant negative activity not only on ER, but also on other NRs, independently of the cellular context. We therefore analyzed the effect of TIF2.5 on the AF-2 activity of ER, RXRα and RARα in HeLa and in Cos-1 cells (FIGS. 12b–d). In all cases, TIF2.5 expression led to a dose-dependent inhibition of the NR AF-2 activity, indicating that the endogenously present mediators were competed out by the isolated overexpressed TIF2 NID, and strongly suggesting that TIF2 or transcriptional intermediary factors recognizing the same or overlapping surfaces mediate NR AF-2 activity in these transfected cells (FIGS. 12b–d, compare lane 2 with lanes 7 and 8, lane 10 with lanes 15 and 16).

It is important to stress that our present data demonstrate that TIF2 interacts with NRs through a surface (NID) that is critical for NR AF-2 activity, as expression of TIF2.5 which encompasses the NID blocked the ligand-induced activity of all tested NR AF-2s. This observation which clearly establishes that, at least in transfected cells, TIF2 or other coactivators which interact with an overlapping, if not identical, holo-LBD surface, are essential to mediate the NR AF-2 activation function. This is in keeping with the presence of three NR box motifs in the TIF2 NID, and of at least one conserved LxxLL (SEQ ID NO:12) NR box motif in all coactivators described to date.

It will be apparent to those skilled in the art that various modifications and variations can be made in the methods of the present invention without departing from the spirit and scope of the invention. Thus, it is intended that the present invention cover all modifications and variations of this invention provided they come within the scope of the appended claims and their equivalents.

The disclosures of all patents, patent applications, and publications referred to above are hereby entirely and expressly incorporated herein by reference.

What is claimed is:

1. An isolated polypeptide having a TIF2 protein activity comprising an amino acid sequence selected from the group consisting of:
   (a) amino acids 1 to 1464 of SEQ ID NO:2;
   (b) the complete amino acid sequence as encoded by the cDNA contained in ATCC Deposit No. 97612,
   (c) amino acids 624 to 869 of SEQ ID NO:2;
   (d) amino acids 624 to 1131 of SEQ ID NO:2;
   (e) amino acids 1010 to 1131 of SEQ ID NO:2;
   (f) amino acids 1288 to 1464 of SEQ ID NO:2;
   (g) amino acids 624 to 1287 of SEQ ID NO:2;
   (h) amino acids 624 to 1179 of SEQ ID NO:2;
   (i) amino acids 624 to 1010 of SEQ ID NO:2;
   (j) amino acids 1180 to 1269 of SEQ ID NO:2;
   (k) amino acids 870 to 1179 of SEQ ID NO:2;
   (l) amino acids 1010 to 1179 of SEQ ID NO:2;
   (m) amino acids 940 to 1179 of SEQ ID NO:2;
   (n) amino acids 940 to 1131 of SEQ ID NO:2; and
   (o) an amino acid sequence at least 90% identical to any of (a)–(n);
   wherein said TIF-2 activity is selected from a group consisting of: binding to a nuclear receptor and enhancing transcription.

2. The isolated polypeptide of claim 1, wherein said amino acid sequence is (a).

3. The isolated polypeptide of claim 1, wherein said amino acid sequence is (b).

4. The isolated polypeptide of claim 1, wherein said amino acid sequence is (c).

5. The isolated polypeptide of claim 1, wherein said amino acid sequence is (d).

6. The isolated polypeptide of claim 1, wherein said amino acid sequence is (e).

7. The isolated polypeptide of claim 1, wherein said amino acid sequence is (f).

8. The isolated polypeptide of claim 1, wherein said amino acid sequence is (g).

9. The isolated polypeptide of claim 1, wherein said amino acid sequence is (h).

10. The isolated polypeptide of claim 1, wherein said amino acid sequence is (i).

11. The isolated polypeptide of claim 1, wherein said amino acid sequence is (j).

12. The isolated polypeptide of claim 1, wherein said amino acid sequence is (k).

13. The isolated polypeptide of claim 1, wherein said amino acid sequence is (j).

14. The isolated polypeptide of claim 1, wherein said amino acid sequence is (m).

15. The isolated polypeptide of claim 1, wherein said amino acid sequence is (n).

16. The isolated polypeptide of claim 1, wherein said amino acid sequence is (o).

17. The isolated polypeptide of claim 16, wherein said amino acid sequence is at least 95% identical to any of (a)–(n).

18. The isolated polypeptide of claim 1, comprising an amino acid sequence at least 90% identical to amino acids 1 to 1464 of SEQ ID NO:2.

19. The isolated polypeptide of claim 1, comprising an amino acid sequence at least 90% identical to amino acids 624 to 869 of SEQ ID NO:2.

20. The isolated polypeptide of claim 1, comprising an amino acid sequence at least 90% identical to amino acids 1010 to 1131 of SEQ ID NO:2.

21. The isolated polypeptide of claim 1, comprising an amino acid sequence at least 90% identical to amino acids 1288 to 1464 of SEQ ID NO:2.

22. The isolated polypeptide of claim 1, which is produced by a recombinant host cell.

* * * * *